(12) United States Patent
Yokokawa et al.

(10) Patent No.: US 8,383,650 B2
(45) Date of Patent: Feb. 26, 2013

(54) ORGANIC COMPOUNDS

(75) Inventors: Fumiaki Yokokawa, Ibaraki (JP);
Takeru Ehara, Ibaraki (JP); Shimpei Kawakami, Ibaraki (JP); Osamu Irie, Ibaraki (JP); Masaki Suzuki, Ibaraki (JP); Yuko Hitomi, Ibaraki (JP); Atsushi Toyao, Ibaraki (JP)

(73) Assignee: Novartis AG, Basel (CH)

( * ) Notice: Subject to any disclaimer, the term of this patent is extended or adjusted under 35 U.S.C. 154(b) by 1254 days.

(21) Appl. No.: 12/146,073

(22) Filed: Jun. 25, 2008

(65) Prior Publication Data

US 2008/0319018 A1    Dec. 25, 2008

(30) Foreign Application Priority Data

Jun. 25, 2007  (EP) .................................... 07012412
Jun. 28, 2007  (EP) .................................... 07111290

(51) Int. Cl.
*C07D 401/12*   (2006.01)
*A61K 31/4545*  (2006.01)
*A61P 9/12*     (2006.01)
*A61P 9/04*     (2006.01)
*A61P 9/10*     (2006.01)
*A61P 13/12*    (2006.01)
*A61P 25/22*    (2006.01)
*A61P 25/28*    (2006.01)
*A61P 27/06*    (2006.01)

(52) U.S. Cl. ........ 514/318; 514/824; 514/866; 514/913; 514/929; 546/193

(58) Field of Classification Search .......................... None
See application file for complete search history.

(56) References Cited

U.S. PATENT DOCUMENTS

| | | | |
|---|---|---|---|
| 6,150,526 A | 11/2000 | Binggeli et al. | |
| 6,197,959 B1 | 3/2001 | Breu et al. | |
| 6,274,735 B1 | 8/2001 | Lohri et al. | |
| 6,376,672 B1 | 4/2002 | Breu et al. | |
| 2002/0087002 A1 | 7/2002 | Breu et al. | |
| 2004/0019137 A1 | 1/2004 | Hebrault | |
| 2004/0077551 A1 | 4/2004 | Campbell et al. | |
| 2004/0204455 A1 | 10/2004 | Cody et al. | |
| 2007/0167433 A1 | 7/2007 | Herold et al. | |
| 2008/0319018 A1 | 12/2008 | Yokokawa et al. | |

FOREIGN PATENT DOCUMENTS

| | | | |
|---|---|---|---|
| EP | 1 908 471 A1 | 4/2008 | |
| EP | 1908471 | 4/2008 | |
| WO | 93/12108 A1 | 6/1993 | |
| WO | 95/09858 A1 | 4/1995 | |
| WO | 97/09311 A1 | 3/1997 | |
| WO | 97/18813 A1 | 5/1997 | |
| WO | 99/09984 A1 | 3/1999 | |
| WO | 99/65867 A1 | 12/1999 | |
| WO | 00/26211 A1 | 5/2000 | |
| WO | 00/51607 A1 | 9/2000 | |
| WO | 00/51608 A1 | 9/2000 | |
| WO | 00/51610 A1 | 9/2000 | |
| WO | 00/63173 A1 | 10/2000 | |
| WO | 00/64873 A1 | 11/2000 | |
| WO | 00/64887 A1 | 11/2000 | |
| WO | 01/70673 A2 | 9/2001 | |
| WO | 02/06387 A2 | 1/2002 | |
| WO | 02/34716 A2 | 5/2002 | |
| WO | 02/076440 A2 | 10/2002 | |
| WO | 02/088101 A2 | 11/2002 | |
| WO | 03/024899 A2 | 3/2003 | |
| WO | 03/031443 A1 | 4/2003 | |
| WO | 03/032962 A2 | 4/2003 | |
| WO | 03/093267 A1 | 11/2003 | |
| WO | 2004/004665 A2 | 1/2004 | |
| WO | 2004/089903 A1 | 10/2004 | |
| WO | 2004/089915 A1 | 10/2004 | |
| WO | 2004/096116 A2 | 11/2004 | |

(Continued)

OTHER PUBLICATIONS

Park J-S, et al: "An efficient synthesis of 3(S)-aminopiperidine-5(R)-carboxylic acid as a cyclic beta, gamma'-diamino acid" Tetrahedon Letters, Elsevier, Amsterdam, NL, vol. 44, No. 8, Feb. 17, 2003. pp. 1611-1614. Cited in the application table 1.

Danieli, Bruno, et al: "An expeditious synthesis of dimethyl 1-benzyl-cis-piperidine-3,5-dicarboxylate" Synthetic Communications, 27(1), 1997, pp. 69-77. Scheme 1.

Specker, et. al.: "An Old Target Revisited: Two New Privileged Skeletons and an Unexpected Binding Mode for HIV-Protease Inhibitors" Angew. Chem. Int. Ed. (2005), 44(20); 3140-44.

Fevig, et. al., "Design and Synthesis of Ring-constrained Boropeptide Thrombin Inhibitors", Bioorg. Med. Chem. Lett. (1996), 6(3): 295-300.

Thomas et. al., Bioorg. Med. Chem. Lett. (1998), 8: 2885-2890.

(Continued)

*Primary Examiner* — Joseph K. McKane
*Assistant Examiner* — Alicia L Otton
(74) *Attorney, Agent, or Firm* — Sophie Binet Cross

(57) ABSTRACT

The present invention relates to a compound of the formula I

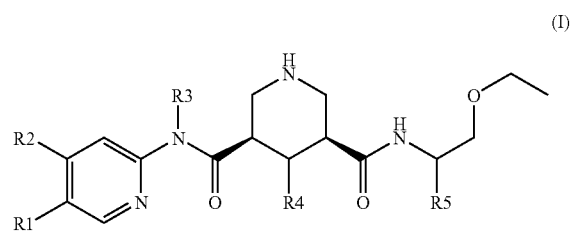

(I)

wherein R1, R2, R3, R4 and R5 are as defined in the specification, for use in the diagnostic and therapeutic treatment of a warm-blooded animal, especially for the treatment of a disease (=disorder) that depends on activity of renin; the use of a compound of that class for the preparation of a pharmaceutical formulation for the treatment of a disease that depends on activity of renin; the use of a compound of that class in the treatment of a disease that depends on activity of renin; pharmaceutical formulations a compound of that class; a method of treatment comprising administering a compound of that class and a method for its manufacture.

6 Claims, No Drawings

FOREIGN PATENT DOCUMENTS

| | | |
|---|---|---|
| WO | 2004/096366 A1 | 11/2004 |
| WO | 2004/096769 A1 | 11/2004 |
| WO | 2004/096799 A1 | 11/2004 |
| WO | 2004/096803 A1 | 11/2004 |
| WO | 2004/096804 A1 | 11/2004 |
| WO | 2005/040120 A1 | 5/2005 |
| WO | 2005/051895 A1 | 6/2005 |
| WO | 2005/051911 A1 | 6/2005 |
| WO | 2005/061457 A1 | 7/2005 |
| WO | 2005/070870 A2 | 8/2005 |
| WO | 2005/070871 A2 | 8/2005 |
| WO | 2005/070877 A1 | 8/2005 |
| WO | 2005/090304 A1 | 9/2005 |
| WO | 2005/090305 A1 | 9/2005 |
| WO | 2006/005741 A2 | 1/2006 |
| WO | 2006/061426 A1 | 6/2006 |
| WO | 2006/066896 A2 | 6/2006 |
| WO | 2006/069788 A1 | 7/2006 |
| WO | 2006/074924 A1 | 7/2006 |
| WO | 2006/094763 A1 | 9/2006 |
| WO | 2006/095020 A1 | 9/2006 |
| WO | 2006/100036 A1 | 9/2006 |
| WO | 2006/103273 A1 | 10/2006 |
| WO | 2006/103275 A1 | 10/2006 |
| WO | 2006/117183 A1 | 11/2006 |
| WO | 2006/125621 A1 | 11/2006 |
| WO | 2006/128659 A2 | 12/2006 |
| WO | 2007/006534 A2 | 1/2007 |
| WO | 2007/031557 A2 | 3/2007 |
| WO | 2007/031558 A1 | 3/2007 |
| WO | 2007/059323 A2 | 5/2007 |
| WO | 2007/077005 A1 | 7/2007 |
| WO | 2007/085651 | 8/2007 |
| WO | 2007/085651 A1 | 8/2007 |
| WO | 2007/141318 | 12/2007 |
| WO | 2007/141318 A1 | 12/2007 |
| WO | 2007/144128 | 12/2007 |
| WO | 2007/144128 A1 | 12/2007 |
| WO | 2007/144129 | 12/2007 |
| WO | 2007/144129 A2 | 12/2007 |
| WO | 2008/031811 | 3/2008 |
| WO | 2008/031811 A1 | 3/2008 |
| WO | 2008/055939 | 5/2008 |
| WO | 2008/055939 A2 | 5/2008 |
| WO | 2008/113835 | 9/2008 |
| WO | 2008/113835 A9 | 9/2008 |

OTHER PUBLICATIONS

Busch et. al., "Synthesis and antimicrobial evaluation of a series of 7-[3-amino (or aminomethyl)-4-aryl (or cyclopropyl)-1-pyrolidinyl]-4-quinolone and -1,8-naphthyridone-3-carboxylic acids", J. Med. Chem (1993), 36(26): 4139-51.

Marki, H. P. et. al., "Piperidine Renin Inhibitors: from leads to drug candidates", IL Farmaco, Rome, IT (2001), 56: 21-27.

Specker; "Dissertation—Rational drug design—Titled: De novo-Design und Synthese neuer Leitstrukturen als Ubergangszustandsmimetika zur selektiven Inhibition der HIV-1 Protease und Cathepsin D"; Fachbereich Pharmazie der Philipps-Universitat Marburg [English Translation of Introduction and issues involved] (2004).

Thomas et. al.; "Beta-Analogs of PLG (L-Prolyl-L-Leucyl-Glycinamide): Ex-Chiral Pool Syntheses and Dopamine D2 Receptor Modulating Effects"; Bioorg. Med. Chem. Lett.; (1998); 8: 2885-2890.

Powell, et al., "Rational design of 6-(2,4-diaminopyrimidiny1)-1,4-benzoxazin-3-ones as small molecule renin inhibitors" Bioorg. Med. Chem. 15(2007) 5912-5949.

Powell, et al., "Equipotent activity in both enantiomers of a series of ketopiperazine-based renin inhibitors" Bioorg med. Chem. Lett. 2005, 15, 2371-2374.

Holsworth, et al., "Discovery of novel non-peptidic ketopiperazine-based renin inhibitors" Bioorg Med. Chem. 2005, 13, 2657-2664.

Powell, et al., "Benzyl ether structure-activity relationships in a series of ketopiperazine-based renin inhibitors" Bioorg Med. Chem. Lett 2005, 15, 4713-4716.

Holsworth, et al., "Ketopiperazine-based renin inhibitors: Optimization of the "C" ring" Bioorg Med. Chem. Lett 2006, 16, 2500-2504.

Holsworth, et al., "Discovery of 6-ethyl-2,4diaminopyrimidine-based small molecule renin inhibitors" Bioorg Med. Chem. Lett, 17 (2007) 3575-3580.

Yokokawa, et al., "Recent advances in the discovery of non-peptidic direct renin inhibitors as antihypertensives: new patent applications in years 2000-2008" Expert Opin. Ther. Patents (2008)18(6), 581-602.

SEQUENCE LISTING

<160> NUMBER OF SEQ ID NOS: 2

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide substrate.
<223> OTHER INFORMATION: The Glutamic Acid is labeled with EDANS
      fluorophore, which interacts with the Dabcyl
      quencher attached to the Lysine at position 13.
<223> OTHER INFORMATION: A Dabcyl quencher is attached to the Lysine,
      which interacts with the EDANS fluorophore attached the
      Glutamic Acid at residue 2.

<400> SEQUENCE: 1

Arg Glu Ile His Pro Phe His Leu Val Ile His Thr Lys Arg
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide substrate with acetate
      attached at N terminus and labeled at C terminus with
      DY-505-X5 (green fluorescent phalloidin derivative
      for selectively labeling F-actin).

<400> SEQUENCE: 2

Ile His Pro Phe His Leu Val Ile His Asn Lys Asp Tyr
 1               5                  10

ORGANIC COMPOUNDS

This application claims benefit under 35 U.S.C. §119(a)-(d) or (f) or 365(b) of EP Applications No. 07111209.8, filed Jun. 28, 2007, and 07012412.8, filed Jun. 25, 2007, the contents of which are incorporated herein by reference in their entirety.

The invention relates to 3,5-substituted piperidine compounds of formula I, these compounds for use in the diagnostic and therapeutic treatment of a warm-blooded animal, especially for the treatment of a disease (=disorder) that depends on activity of renin; the use of a compound of that class for the preparation of a pharmaceutical formulation for the treatment of a disease that depends on activity of renin; the use of a compound of that class in the treatment of a disease that depends on activity of renin; pharmaceutical formulations comprising said 3,5-substituted piperidine compound; a method of treatment comprising administering said 3,5-substituted piperidine compound and a method for the manufacture of said 3,5-substituted piperidine compounds.

We have recently described novel 3,5-substituted piperidines which are useful as renin inhibitors (see PCT/EP06/012581). Although these compounds are suitable and effective for this purpose, there is a continued need to develop renin inhibitors with a further improved pharmacokinetic profile whilst at the same time achieving a good potency and safety profile. In particular, the provision of renin inhibitors with enhanced bioavailability is of therapeutic advantage. Bioavailability is an important factor limiting the therapeutic applications of bioactive compounds. The object of the present invention was thus to provide novel potent renin inhibitors with enhanced bioavailability.

The present invention relates to a compound of the formula I

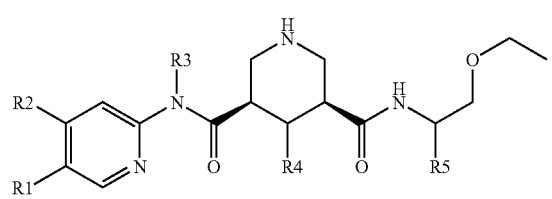

(I)

wherein
R1 is $C_{1-7}$alkyl, which is optionally substituted by one, two or three substituents selected form the group consisting of hydroxyl, halo and $C_1$-$C_7$-alkoxy;
R2 is hydrogen, $C_{1-7}$alkyl, $C_1$-$C_7$-alkoxy, halo-$C_1$-$C_7$-alkyl, halo-$C_1$-$C_7$-alkoxy or $C_1$-$C_7$-alkoxy-$C_1$-$C_7$-alkoxy;
R3 is $C_{1-7}$alkyl or $C_{3-8}$cycloalkyl;
R4 is hydrogen or hydroxyl; and
R5 is $C_{1-7}$alkyl or $C_{3-8}$cycloalkyl;
or a salt thereof.

In one preferred embodiment the invention relates to a compound of the formula I wherein
R1 is $C_{1-7}$alkyl, which is optionally substituted by one, two or three substituents selected form the group consisting of hydroxyl, halo and $C_1$-$C_7$-alkoxy;
R2 is hydrogen, $C_{1-7}$alkyl, $C_1$-$C_7$-alkoxy, halo-$C_1$-$C_7$-alkyl or halo-$C_1$-$C_7$-alkoxy;
R3 is $C_{1-7}$alkyl or $C_{3-8}$cycloalkyl;
R4 is hydrogen or hydroxyl; and
R5 is $C_{1-7}$alkyl or $C_{3-8}$cycloalkyl;
or a salt thereof.

The present invention also relates to a compound of the formula II

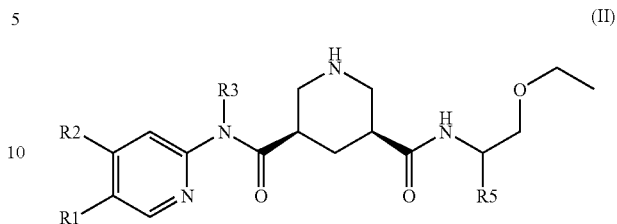

(II)

wherein
R1 is $C_{1-7}$alkyl, which is optionally substituted by one, two or three substituents selected form the group consisting of hydroxyl, halo and $C_1$-$C_7$-alkoxy;
R2 is hydrogen, $C_{1-7}$alkyl, $C_1$-$C_7$-alkoxy, halo-$C_1$-$C_7$-alkyl, halo-$C_1$-$C_7$-alkoxy or $C_1$-$C_7$-alkoxy-$C_1$-$C_7$-alkoxy;
R3 is $C_{1-7}$alkyl or $C_{3-8}$cycloalkyl;
R4 is hydrogen or hydroxyl; and
R5 is $C_{1-7}$alkyl or $C_{3-8}$cycloalkyl;
or a salt thereof.

In another preferred embodiment the invention relates to a compound of the formula II wherein
R1 is $C_{1-7}$alkyl, which is optionally substituted by one, two or three substituents selected form the group consisting of hydroxyl, halo and $C_1$-$C_7$-alkoxy;
R2 is hydrogen, $C_{1-7}$alkyl, $C_1$-$C_7$-alkoxy, halo-$C_1$-$C_7$-alkyl or halo-$C_1$-$C_7$-alkoxy;
R3 is $C_{1-7}$alkyl or $C_{3-8}$cycloalkyl;
R4 is hydrogen or hydroxyl; and
R5 is $C_{1-7}$alkyl or $C_{3-8}$cycloalkyl;
or a salt thereof.

The compounds of the formula II are preferred embodiments of the formula I wherein R4 is hydrogen.

The present invention also relates to a compound of the formula III

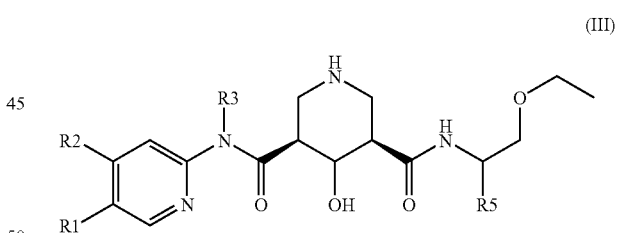

(III)

R1 is $C_{1-7}$alkyl, which is optionally substituted by one, two or three substituents selected form the group consisting of hydroxyl, halo and $C_1$-$C_7$-alkoxy;
R2 is hydrogen, $C_{1-7}$alkyl, $C_1$-$C_7$-alkoxy, halo-$C_1$-$C_7$-alkyl, halo-$C_1$-$C_7$-alkoxy or $C_1$-$C_7$-alkoxy-$C_1$-$C_7$-alkoxy;
R3 is $C_{1-7}$alkyl or $C_{3-8}$cycloalkyl;
R4 is hydrogen or hydroxyl; and
R5 is $C_{1-7}$alkyl or $C_{3-8}$cycloalkyl;
or a salt thereof.

The compounds of the formula III are preferred embodiments of the formula I wherein R4 is hydroxyl.

The compounds of the present invention exhibit inhibitory activity on the natural enzyme renin. Thus, compounds of formula I may be employed for the treatment (this term also including prophylaxis) of one or more disorders or diseases especially selected from the diseases given in detail below, especially as far as these diseases can be modulated (more especially beneficially influenced) by renin inhibition. Listed below are definitions of various terms used to describe the compounds of the present invention as well as their use and synthesis, starting materials and intermediates and the like. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group.

Alkyl is $C_1$-$C_7$-alkyl, more preferably $C_1$-$C_4$-alkyl, that is straight-chained or branched (one or, where appropriate, more times). The term $C_1$-$C_7$ alkyl defines a moiety with up to and including maximally 7, especially up to and including maximally 4, carbon atoms, said moiety being branched (one or more times) or straight-chained and bound via a terminal or a non-terminal carbon. $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl or tert-butyl.

Halo or halogen is preferably fluoro, chloro, bromo or iodo, most preferably fluoro, chloro or bromo; where halo is mentioned, this can mean that one or more (e.g. up to three) halogen atoms are present in moieties such as halo-$C_1$-$C_7$-alkyl, halo-$C_1$-$C_7$-alkoxy and the like (e.g. trifluoromethyl).

$C_3$-$C_8$-cycloalkyl is preferably mono- or bicyclic, more preferably monocyclic, cycloalkyl, which may include one or more double and/or triple bonds, $C_3$-$C_6$-cycloalkyl is preferred.

$C_1$-$C_7$-alkoxy is, for example, $C_1$-$C_4$-alkoxy and may be linear or branched. Examples are methoxy, ethoxy, n- and i-propyloxy, n-, i- and t-butyloxy, pentyloxy and hexyloxy. $C_1$-$C_4$alkoxy is preferred.

Aryl preferably is a mono- or bicyclic aryl with 6 to 22 carbon atoms, especially phenyl, indenyl, indanyl or naphthyl, in particular phenyl.

Alkenyl may be linear or branched alkyl containing a double bond and comprising preferably 2 to 12 C atoms, 2 to 8 C atoms being especially preferred. Particularly preferred is a linear $C_{2-4}$alkenyl. Especially preferred is allyl.

Bonds with the asterisk (*) denote point of binding to the rest of the molecule.

In all definitions above and below the person having skill in the art will, without undue experimentation or effort, be able to recognize which are especially relevant (e.g. those that if present provide compounds that are sufficiently stable for the manufacture of pharmaceuticals, e.g. having a half-life of more than 30 seconds, preferably of more than a week) and thus are preferably encompassed by the present claims and that only chemically feasible bonds and substitutions (e.g. in the case of double or triple bonds, hydrogen carrying amino or hydroxy groups and the like can be avoided in order to avoid tautomerism) are encompassed, as well as tautomeric forms where present, especially in equilibrium. For example, preferably, for reasons of stability or chemical feasibility, directly vicinal atoms in chains preferably are not selected from oxy plus oxy, thio plus oxy, oxy plus thio or thio plus thio, except where ring systems or the like are present that are sufficiently stable. Substitutents binding via an O (e.g. in $C_1$-$C_7$-alkoxy) or S that is part of them are preferably not bound to nitrogen e.g. in rings.

Salts are especially the pharmaceutically acceptable salts of compounds of formula I. They can be formed where salt forming groups, such as basic or acidic groups, are present that can exist in dissociated form at least partially, e.g. in a pH range from 4 to 10 in aqueous solutions, or can be isolated especially in solid, especially crystalline, form.

Such salts are formed, for example, as acid addition salts, preferably with organic or inorganic acids, from compounds of formula I with a basic nitrogen atom (e.g. imino or amino), especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfonyl, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable comprised in pharmaceutical preparations), and these are therefore preferred.

In view of the close relationship between the compounds in free form and in the form of their salts, including those salts that can be used as intermediates, for example in the purification or identification of the compounds or salts thereof, any reference to "compounds", "starting materials" and "intermediates" hereinbefore and hereinafter, especially to the compound(s) of the formula I or their precursors, is to be understood as referring also to one or more salts thereof or a mixture of a corresponding free compound and one or more salts thereof, each of which is intended to include also any solvate, metabolic precursor such as ester or amide of the compound of formula I, or salt of any one or more of these, as appropriate and expedient and if not explicitly mentioned otherwise. Different crystal forms may be obtainable and then are also included.

Where the plural form is used for compounds, starting materials, intermediates, salts, pharmaceutical preparations, diseases, disorders and the like, this is intended to mean one (preferred) or more single compound(s), salt(s), pharmaceutical preparation(s), disease(s), disorder(s) or the like, where the singular or the indefinite article ("a", "an") is used, this is intended to include the plural (for example also different configuration isomers of the same compound, e.g. enantiomers in racemates or the like) or preferably the singular ("one").

The compounds of the present invention can possess two or more asymmetric centers depending on the choice of the substituents. The preferred absolute configurations are as indicated herein specifically. However, any possible isolated or pure diastereoisomers, enantiomers or geometric enantiomers, and mixtures thereof, e.g., mixtures of enantiomers, such as racemates, are encompassed by the present invention.

As described above, the compounds of the present invention are inhibitors of renin activity and, thus, may be employed for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, Alzheimer's disease, dementia, anxiety states and cognitive disorders, and the like, especially where inhibition of (especially inappropriate) renin activity is required.

"Inappropriate" renin activity preferably relates to a state of a warm-blooded animal, especially a human, where renin shows a renin activity that is too high in the given situation (e.g. due to one or more of misregulation, overexpression e.g. due to gene amplification or chromosome rearrangement or infection by microorganisms such as virus that express an aberrant gene, abnormal activity e.g. leading to an erroneous substrate specificity or a hyperactive renin e.g. produced in normal amounts, too low activity of renin activity product removing pathways, high substrate concentration and/or the like) and/or leads to or supports a renin dependent disease or disorder as mentioned above and below, e.g. by too high renin activity. Such inappropriate renin activity may, for example, comprise a higher than normal activity, or further an activity in the normal or even below the normal range which, however, due to preceding, parallel and or subsequent processes, e.g. signaling, regulatory effect on other processes, higher substrate or product concentration and the like, leads to direct or indirect support or maintenance of a disease or disorder, and/or an activity that supports the outbreak and/or presence of a disease or disorder in any other way. The inappropriate activity of renin may or may not be dependent on parallel other mechanisms supporting the disorder or disease, and/or the prophylactic or therapeutic effect may or may include other mechanisms in addition to inhibition of renin. Therefore "dependent" can be read as "dependent inter alia", (especially in cases where a disease or disorder is really exclusively dependent only on renin) preferably as "dependent mainly", more preferably as "dependent essentially only". A disease dependent on (especially inappropriate) activity of renin may also be one that simply responds to modulation of renin activity, especially responding in a beneficial way (e.g. lowering the blood pressure) in case of renin inhibition.

Where a disease or disorder dependent on (=that "depends on", "depending") (especially inappropriate) activity of a renin is mentioned (such in the definition of "use" in the following paragraph and also especially where a compound of the formula I is mentioned for use in the diagnostic or therapeutic treatment which is preferably the treatment of a disease or disorder dependent on inappropriate renin activity, this refers preferably to any one or more diseases or disorders that depend on inappropriate activity of natural renin and/or one or more altered or mutated forms thereof.

Where subsequently or above the term "use" is mentioned (as verb or noun) (relating to the use of a compound of the formula I or of a pharmaceutically acceptable salt thereof, or a method of use thereof), this (if not indicated differently or to be read differently in the context) includes any one or more of the following embodiments of the invention, respectively (if not stated otherwise): the use in the treatment of a disease or disorder that depends on (especially inappropriate) activity of renin, the use for the manufacture of pharmaceutical compositions for use in the treatment of a disease or disorder that depends on (especially inappropriate) activity of renin; a method of use of one or more compounds of the formula I in the treatment of a disease or disorder that depends on (especially inappropriate) activity of renin; a pharmaceutical preparation comprising one or more compounds of the formula I for the treatment of a disease or disorder that depends on (especially inappropriate) activity of renin; and one or more compounds of the formula I for use in the treatment of a disease or disorder in a warm-blooded animal, especially a human, preferably a disease that depends on (especially inappropriate) activity of renin; as appropriate and expedient, if not stated otherwise.

The terms "treat", "treatment" or "therapy" refer to the prophylactic (e.g. delaying or preventing the onset of a disease or disorder) or preferably therapeutic (including but not limited to preventive, delay of onset and/or progression, palliative, curing, symptom-alleviating, symptom-reducing, patient condition ameliorating, renin-modulating and/or renin-inhibiting) treatment of said disease(s) or disorder(s), especially of the one or more diseases or disorders mentioned above or below.

PREFERRED EMBODIMENTS ACCORDING TO THE INVENTION

The groups of preferred embodiments of the invention mentioned below are not to be regarded as exclusive, rather, e.g., in order to replace general expressions or symbols with more specific definitions, parts of those groups of compounds can be interchanged or exchanged using the definitions given above, or omitted, as appropriate, and each of the more specific definitions, independent of any others, may be introduced independently of or together with one or more other more specific definitions for other more general expressions or symbols.

The invention preferably relates to a compound of the formula I, II or III wherein the moiety R5 is bound in the R configuration or alternatively wherein this moiety is bound in the S configuration.

The invention thus more preferably relates to a compound of the formula I, II or III as defined herein before or hereinafter which has the configuration shown in the following formula IIA or IIB,

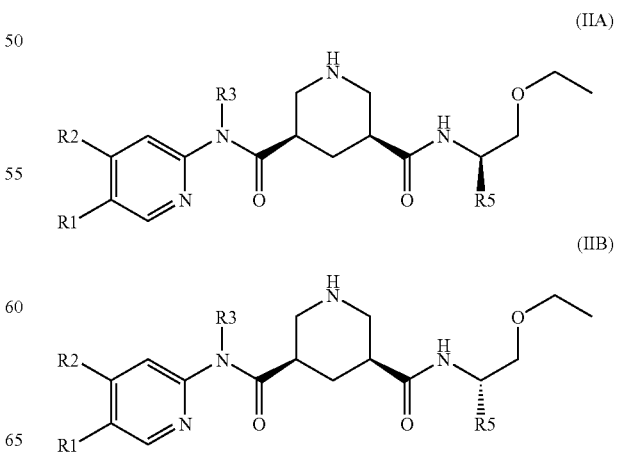

or a (preferably pharmaceutically acceptable) salt thereof, or alternatively the configuration shown in the following formulae IIIA or IIIB

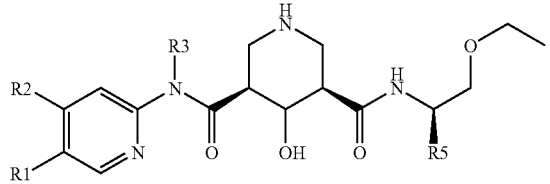
(IIIA)

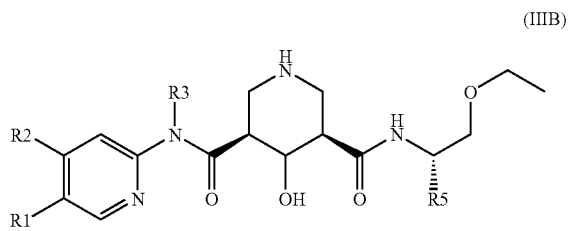
(IIIB)

or a (preferably pharmaceutically acceptable) salt thereof, where in formulae IIA, IIB, IIIA and IIIB, R1, R2, R3 and R5 are as defined above or below for a compound of the formula I.

Alternatively and also more preferably, the invention relates to a compound of the formula I or III as defined herein before or hereinafter which has the configuration shown in the following formula III',

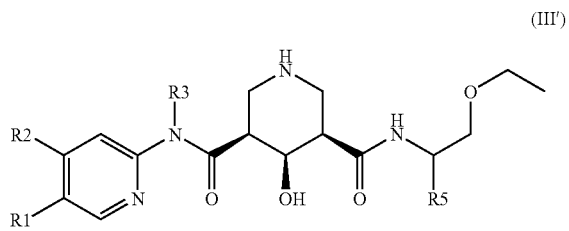
(III')

or a (preferably pharmaceutically acceptable) salt thereof, where in formulae III', R1, R2, R3 and R5 are as defined above or below for a compound of the formula I.

Alternatively and also more preferably, the invention relates to a compound of the formula I or III as defined herein before or hereinafter which has the configuration shown in the following formula III'A or III'B,

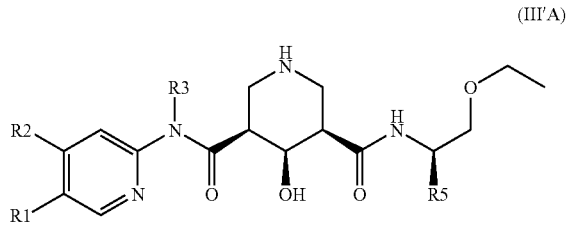
(III'A)

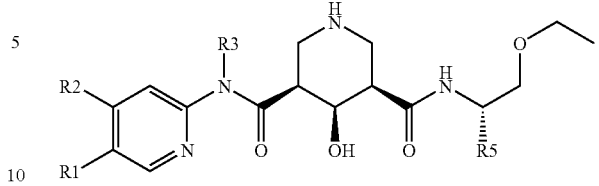
(III'B)

or a (preferably pharmaceutically acceptable) salt thereof, where in formulae III'A and III'B, R1, R2, R3 and R5 are as defined above or below for a compound of the formula I.

In a first preferred embodiment, the invention especially relates to a compound of the formulae I, II, III, III', IIA, IIB, IIIA, IIIB, III'A or III'B, wherein R1 is a $C_{1-7}$alkyl, more preferably $C_{1-4}$-alkyl, which is optionally substituted by $C_1$-$C_7$-alkoxy, more preferably $C_{1-4}$-alkoxy. In one embodiment, R1 is a $C_{1-7}$alkyl, which is unsubstituted. Particularly preferred examples for R1 are selected from

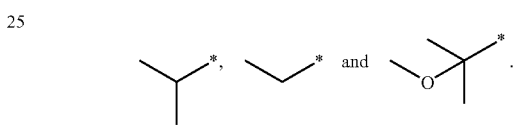

In another preferred embodiment, the invention especially relates to a compound of the formulae I, II, III, III', IIA, IIB, IIIA, IIIB, III'A or III'B, wherein R2 is hydrogen, $C_1$-$C_7$-alkoxy or $C_1$-$C_7$-alkoxy-$C_1$-$C_7$-alkoxy; more preferably hydrogen, $C_1$-$C_4$-alkoxy or $C_1$-$C_4$-alkoxy-$C_1$-$C_4$-alkoxy. Particularly preferred examples for R2 are selected from

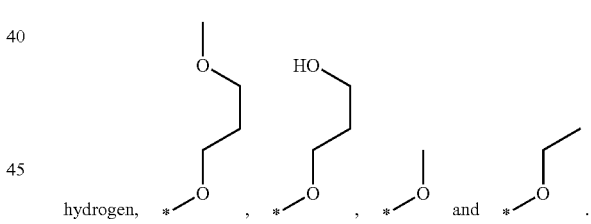

In one preferred embodiment, the invention especially relates to a compound of the formulae I, II, III, III', IIA, IIB, IIIA, IIIB, III'A or III'B, wherein R2 is hydrogen or $C_1$-$C_7$-alkoxy; more preferably hydrogen or $C_1$-$C_4$-alkoxy. Particularly preferred examples for R2 are selected from

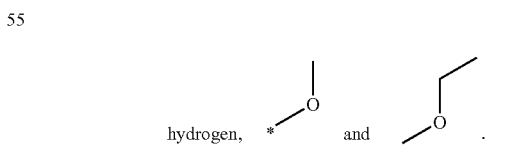

In another preferred embodiment, the invention especially relates to a compound of the formulae I, II, III, III', IIA, IIB, IIIA, IIIB, III'A or III'B, wherein R3 is $C_{3-7}$alkyl or $C_{3-6}$-cycloalkyl; more preferably branched $C_{4-6}$-alkyl or cyclopropyl. Particularly preferred examples for R3 are

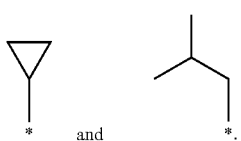

In one embodiment, R3 is cyclopropyl.

In another preferred embodiment, the invention especially relates to a compound of the formulae I, II, III, III', IIA, IIB, IIIA, IIIB, III'A or III'B, wherein R5 is $C_{1-5}$alkyl or $C_{3-6}$-cycloalkyl; more preferably $C_{1-4}$alkyl or cyclohexyl. The alkyl can be branched or bonded via a non-terminal C. Particularly preferred examples for R5 are

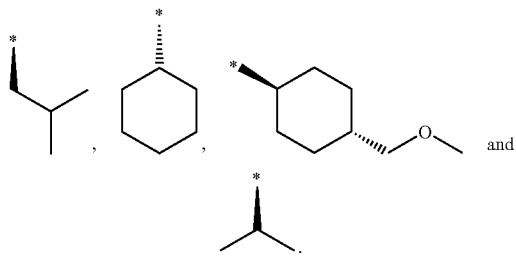

Particular embodiments of the invention are provided in the Examples—the invention thus, in a very preferred embodiment, relates to a compound of the formula I or a salt thereof, selected from the compounds given in the Examples, as well as the use thereof according to the invention.

Process of Manufacture

A compound of formula I, or a salt thereof, is prepared especially as described or in analogy to methods described in PCT/EP06/012581, in general by a process comprising:

a) reacting a compound of the formula IV,

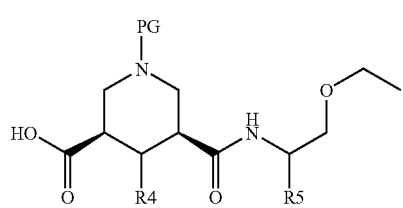

wherein PG is a protecting group and R4 and R5 are as defined above, or (preferably) an activated derivative thereof, with a compound of the formula V,

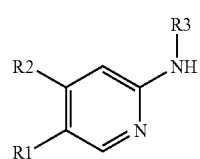

wherein R1, R2 and R3 are as defined above; or b) reacting a compound of the formula VI,

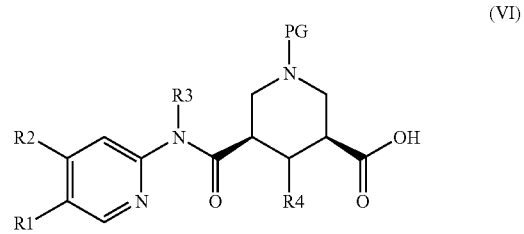

wherein PG is a protecting group and R1, R2, R3 and R4 are as defined above, or (preferably) an activated derivative thereof, with a compound of the formula VII,

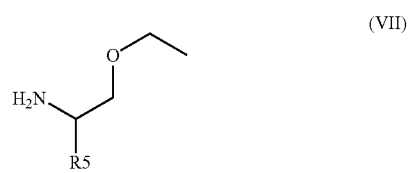

wherein R5 is as defined above;

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups or bound resins are removed at an appropriate stage in order to obtain a corresponding compound of the formula I, or a salt thereof.

Alternatively, a compound of formula I, or a salt thereof, is prepared in general by a process comprising:

reacting a compound of formula (IXa)

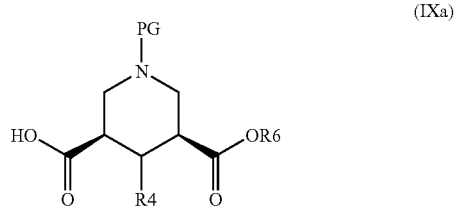

wherein PG is a protecting group, R4 is as defined above and R6 is unsubstituted or substituted alkyl or alkenyl, preferably $C_1$-$C_4$ alkyl, or (preferably) an activated derivative thereof, with a compound of the formula V,

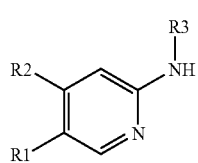
(V)

wherein R1, R2 and R3 are as defined above; to obtain the amide of formula Xa

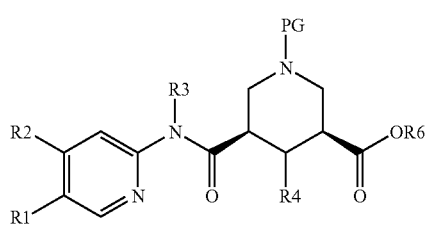
(Xa)

which is subjected to hydrolysis of the ester moiety to obtain a compound of formula XIa

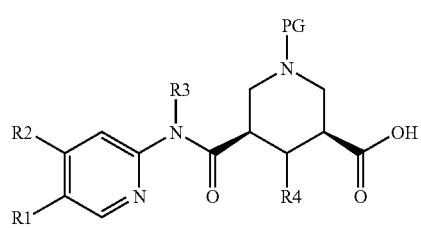
(XIa)

which compound or (preferably) an activated derivative thereof, can be in turn reacted with a compound of the formula VII,

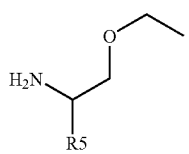
(VII)

wherein R5 is as defined above, to obtain a compound of formula XII

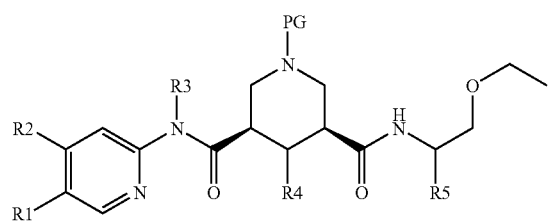
(XII)

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups or bound resins are removed at an appropriate stage in order to obtain a corresponding compound of the formula I, or a salt thereof. In addition, a compound of formula I, or a salt thereof, can be prepared in general by a process comprising:

reacting a compound of formula (IXb)

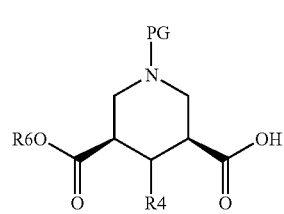
(IXb)

wherein PG is a protecting group, R4 is as defined above and R6 is unsubstituted or substituted alkyl or alkenyl, preferably $C_1$-$C_4$ alkyl, or (preferably) an activated derivative thereof, with a compound of the formula VII,

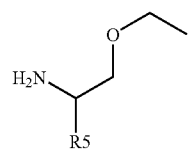
(VII)

wherein R5 is as defined above, to obtain the amide of formula Xb

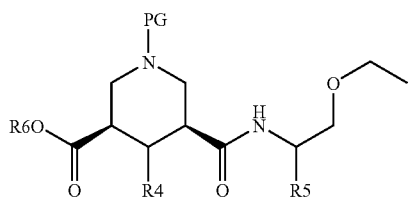
(Xb)

which is subjected to hydrolysis of the ester moiety to obtain a compound of formula XIb

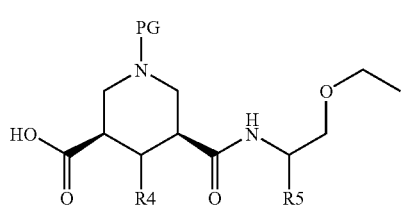
(XIb)

which compound or (preferably) an activated derivative thereof, can be in turn reacted with a compound of the formula V,

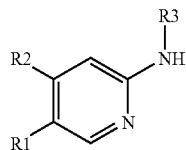
(V)

wherein R1, R2 and R3 are as defined above, to obtain a compound of formula XII

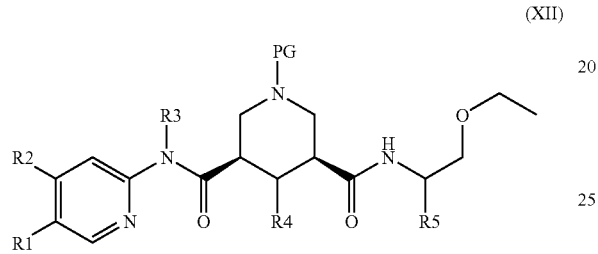
(XII)

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups or bound resins are removed at an appropriate stage in order to obtain a corresponding compound of the formula I, or a salt thereof.

In the case of a compound of the formula IV, VI, IXa, IXb, XIa or XIb, an activated derivative thereof, is the corresponding compound wherein the OH group of the carboxyl is preferably replaced by a leaving group, such as halo, e.g. chloro, bromo or iodo, or organic sulfonyloxy, such as tosyloxy or methanesulfonyloxy. The reaction of such activated derivative thereof with a compound of the formula V or VII then preferably takes under standard conditions for nucleophilic substitution. In a preferred embodiment, activated derivatives include, for example, acyl halides, anhydrides, and activated esters. An activated ester is one which is known to one skilled in the art, for example N-succinimide. An activated derivative of a carboxylic acid of formula IV, VI, IXa or IXb is, for example, the corresponding intermediate compound formed upon reaction of said acid with EDCl, BopCl or TcBocCl. In another preferred embodiment, an activated derivative of compounds of formula IV, VI, IXa, IXb, XIa or XIb is the corresponding derivative formed under Vilsmeier reaction conditions.

Moreover, a process for the manufacture of a compound of the formula I, or a pharmaceutically acceptable salt thereof, can comprise reacting a compound of the formula VIII

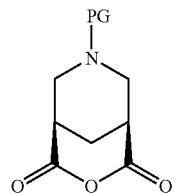
(VIII)

wherein PG is a protecting group, with an alcohol R6OH, wherein R6 is unsubstituted or substituted alkyl or alkenyl, preferably $C_1$-$C_4$ alkyl, in the presence of a chiral amine catalyst, to obtain a compound of formula VIII'a or VIII'b

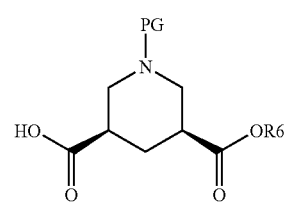
(VIII'a)

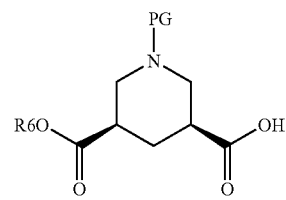
(VIII'b)

The nature of the amine governs the position of the ester formation and thus the stereoselectivity. Preferred examples of the chiral amine catalyst are chiral tertiary amines, more preferably cinchona alkaloids, such as quinidine and quinine, most preferably modified cinchona alkaloids. Examples of such modified cinchona alkaloids are given below. For a more detailed description, reference is made to Tian, S.-K.; Chen, Y.; Hang, J.; Tang, L.; McDiad, P.; Deng, L. *Acc. Chem. Res.* 2004, 37, 621-631 and references cited therein.

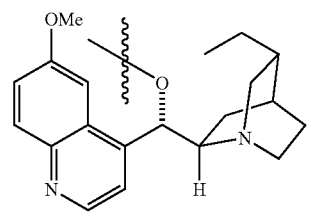
DHQD(dihydroquinidyl)

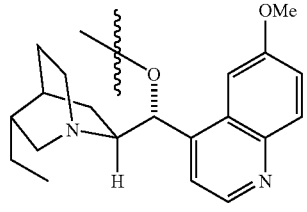
DHQ(dihydroquiniyl)

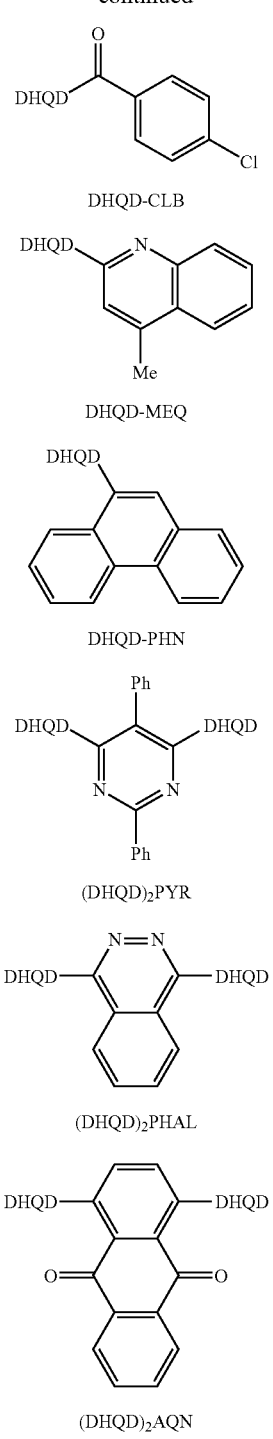

ABBREVIATIONS

DHQD-CLB Hydroquinidine 4-chlorobenzoate
DHQ-CLB Hydroquinine 4-chlorobenzoate
DHQD-MEQ Hydroquinidine 4-methyl-2-quinolyl ether
DHQ-MEQ Hydroquinine 4-methyl-2-quinolyl ether
DHQD-PHN Hydroquinidine 9-O-(9'-phenanthryl)ether
DHQ-PHN Hydroquinine 9-O-(9'-phenanthryl)ether
(DHQD)$_2$PYR Hydroquinidine 2,5-diphenyl-4,6-pyrimidinediyl diether
(DHQ)$_2$PYR Hydroquinine 2,5-diphenyl-4,6-pyrimidinediyl diether
(DHQD)$_2$PHAL Hydroquinidine 1,4-phthalazinediyl diether
(DHQ)$_2$PHAL Hydroquinine 1,4-phthalazinediyl diether
(DHQD)$_2$AQN Hydroquinidine anthraquinone-1,4-diyl diether
(DHQ)$_2$AQN Hydroquinine anthraquinone-1,4-diyl diether Preferred amines are DHQ, such as (DHQ)$_2$AQN, and DHQD, such as (DHQD)$_2$AQN. For reaction conditions, reference is made again to Tian, S.-K. et al. Specifically, the chiral amine catalyst is typically employed in a below-equimolar amount, preferably below 50 mol %, such as 5 to 40 mol %, more preferably 10 to 35 mol %, most preferably 30 mol %.

The alcohol R6OH is a suitable alcohol for esterification on a compound of formula VIII and hydrolysis in the presence of an amide, such as unsubstituted or substituted alkyl or alkenyl, preferably $C_1$-$C_4$ alkyl, whereby substituted alkyl is preferably selected from halo, aryl or substituted alkyl, in particular fluoro or phenyl. Examples of substituted alkyl include trifluoromethyl, difluoromethyl, difluoroethyl, fluoromethyl, fluoroethyl or benzyl. Most preferably, R6OH is methanol1.

Reaction solvents can be chosen as described below, in particular preferred are ethereal solvents such as diethyl ether or tetrahydrofuran (THF) or mixtures of these such as diethyl ether:THF (4:1) or (3:1). The reaction temperature can be chosen so as to bring the reaction to completion in an efficient manner while at the same time suppress the formation of unwanted side products as much as possible. Typical reaction temperatures are −100 to 20° C., such as −80 to 10° C., preferably −40 to 0° C.

Separation of the products VIII'a or VIII'b can be achieved by suitable recrystallization techniques known in the art. For example, reference is made to the recrystallization methods employed in Park, J.-S.; Yeom, C.-E.; Choi, S. H.; Ahn, Y. S.; Ro, S.; Jeom, Y. H.; Shin, D.-K.; Kim, B. M. *Tetrahedron Lett.* 2003, 44, 1611-1614 and the reference cited therein. Thus, chiral amines such as α-phenylethylamine can be employed.

Scheme 1a and 1b show two preferred methods for preparing a compound of formula II. It should be noted that the brief description on each of the arrows for each conversion has been added for illustration purposes only and should not be regarded as limiting with respect to the sequence or each individual step.

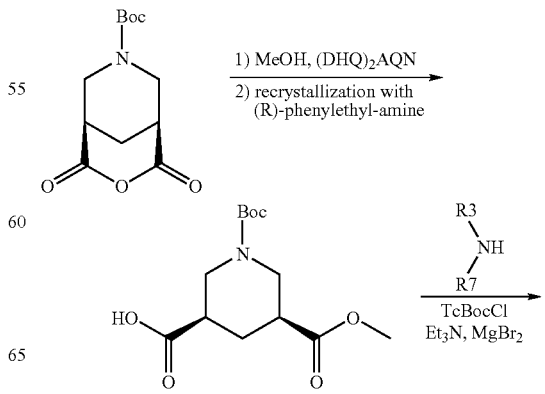

Scheme 1a

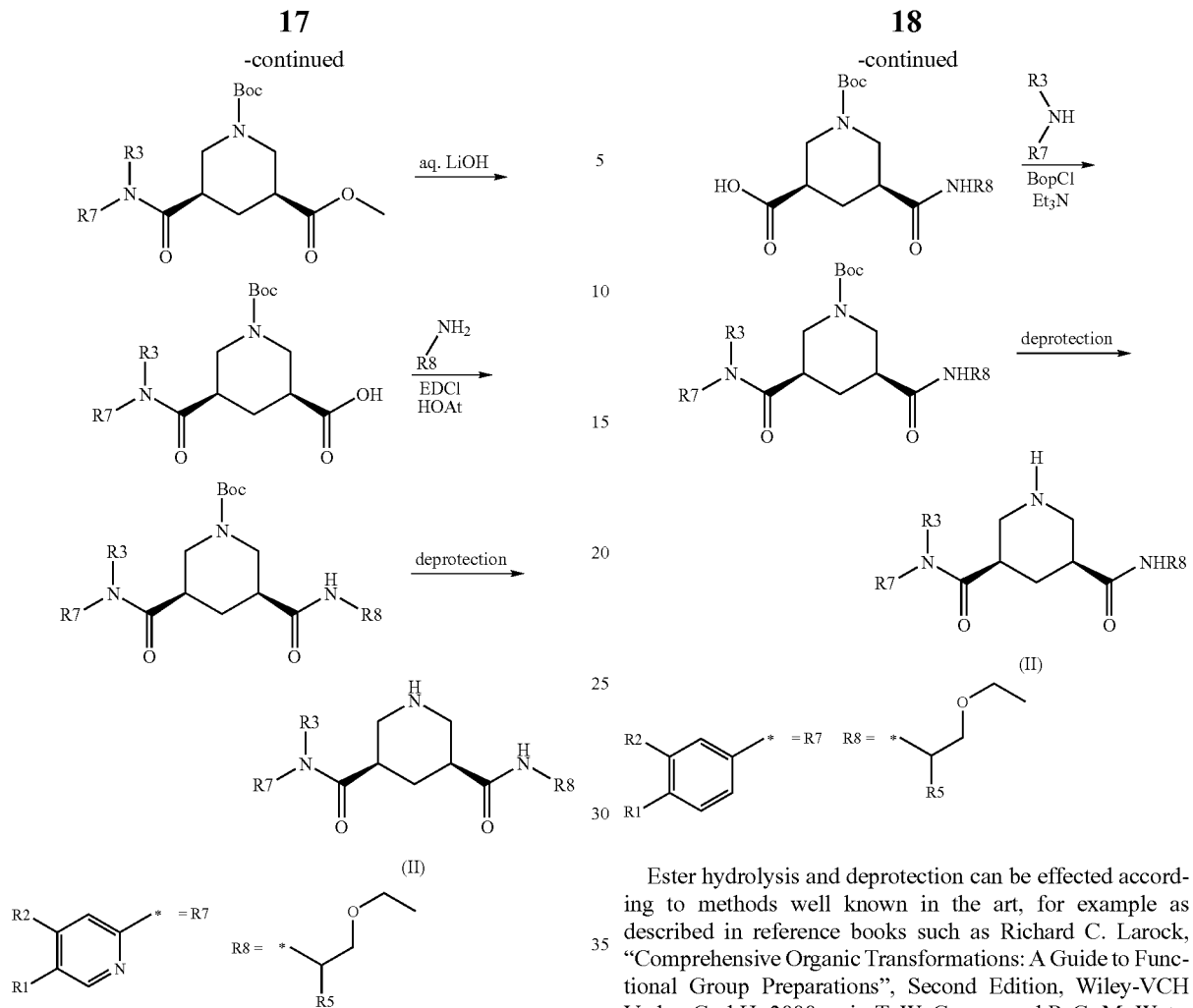

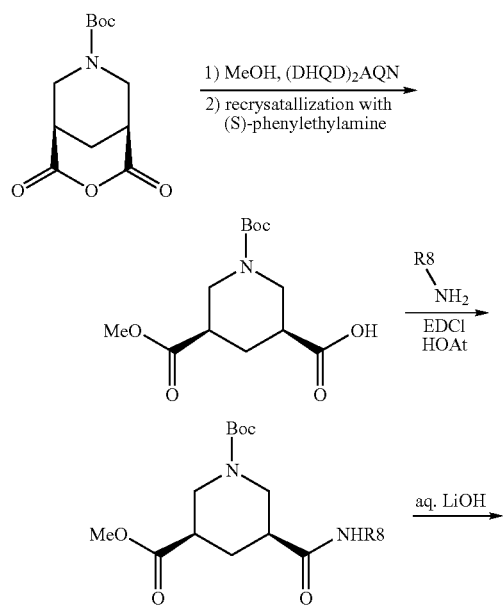

Ester hydrolysis and deprotection can be effected according to methods well known in the art, for example as described in reference books such as Richard C. Larock, "Comprehensive Organic Transformations: A Guide to Functional Group Preparations", Second Edition, Wiley-VCH Verlag GmbH, 2000 or in T. W. Greene and P. G. M. Wuts, "Protective Groups in Organic Synthesis", Third edition, Wiley, New York 1999; see also the reference made below with respect to protection and deprotection methods.

The present invention includes all pharmaceutically acceptable isotopically-labeled compounds of formula (I) wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{13}$O, phosphorus, such as $^{32}$P, and sulphur, such as $^{35}$S.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of formula (I) can generally be prepared by conventional techniques known to those skilled in the art or by processes analogous to those described in the accompanying Examples and Preparations Sections using an appropriate isotopically-labeled reagent in place of the non-labeled reagent previously employed.

Starting Materials

In the subsequent description of starting materials (this term including also intermediates) and their synthesis, R1, R2, R3, R4, R5, R6, R7, R8 and PG have the meanings given above or in the Examples for the respective starting materials or intermediates, if not indicated otherwise directly or by the context. Protecting groups, if not specifically mentioned, can be introduced and removed at appropriate steps in order to prevent functional groups, the reaction of which is not desired in the corresponding reaction step or steps, employing protecting groups, methods for their introduction and their removal are as described above or below. The person skilled in the art will readily be able to decide whether and which protecting groups are useful or required.

Where for any of the starting materials isomers (e.g. diastereomers, enantiomers) are present, they can be separated according to standard procedures at appropriate stages. Other starting materials are known in the art, commercially available, and/or they can be found in or derived analogously from the Examples.

General Process Conditions

The following applies in general (where possible) to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula I is designated a "protecting group" or PG, unless the context indicates otherwise. The protection of functional groups by such protecting groups, the protecting groups themselves, and the reactions appropriate for their introduction and removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of Organic Chemistry*), Houben Weyl, 4th edition, Volume 15/I, Georg Thieme Verlag, Stuttgart 1974, in H.-D. Jakubke and H. Jeschkeit, "Aminosäuren, Peptide, Proteine" (*Amino acids, Peptides, Proteins*), Verlag Chemie, Weinheim, Deerfield Beach, and Basel 1982, and in Jochen Lehmann, "Chemie der Kohlenhydrate: Monosaccharide und Derivate" (*Chemistry of Carbohydrates: Monosaccharides and Derivatives*), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

Examples of the protecting group or PG, in particular for nitrogen such as the piperidine nitrogen of the compounds described herein are alkoxycarbonyl, sulfonyl and acyl groups. Preferred protecting groups comprise, for example, (i) $C_1$-$C_2$-alkyl that is mono-, di- or trisubstituted by phenyl, such as benzyl, (or) benzhydryl or trityl, wherein the phenyl ring is unsubstituted or substituted by one or more, e.g. two or three, residues e.g. those selected from the group consisting of $C_1$-$C_7$-alkyl, hydroxy, $C_1$-$C_7$-alkoxy, halogen, nitro, cyano, and $CF_3$; phenyl-$C_1$-$C_2$-alkoxycarbonyl; and allyl or cinnamyl. Especially preferred are lower (e.g. $C_1$-$C_7$) alkoxycarbonyl, such as tert-butoxycarbonyl or benzyloxycarbonyl; benzyloxycarbonyl (Cbz), 9-fluorenylmethyloxycarbonyl (Fmoc), benzyloxymethyl (BOM), pivaloyl-oxy-methyl (POM), trichloroethxoycarbonyl (Troc), 1-adamantyloxycarbonxyl (Adoc), but can also be benzyl, cumyl, benzhydryl, trityl, allyl, alloc (allyloxycarbonyl). The protecting group can also be silyl, like trialklysilyl, especially trimethylsilyl, tert-butyl-dimethylsilyl, triethylsilyl, triisopropylsilyl, trimethylsilyethoxymethyl (SEM), and can also be substituted sulfonyl or substituted sulfenyl. Most preferred is lower (e.g. $C_1$-$C_7$) alkoxycarbonyl, such as tert-butoxycarbonyl. The protecting group may also be a sulfonyl group, preferably an aryl sulfonyl group such as a substituted or unsubstituted phenyl sulfonyl group. In this case, phenyl, if substituted, may be mono-, di- or tri-substituted, preferably mono- or di-substituted with a suitable substituent such as $C_1$-$C_7$-alkyl, $C_1$-$C_7$-alkoxy, halo-$C_1$-$C_7$-alkyl, halo-$C_1$-$C_7$-alkoxy, halo, hydroxy, nitro, cyano, more preferably nitro or methyl. Particularly preferred examples of the sulfonyl protecting group are 2,4-dinitrophenylsulfonyl, 4-nitrophenyl sulfonyl, 2-nitrophenyl sulfonyl and 4-methylphenyl sulfonyl.

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about $-100°$ C. to about $190°$ C., preferably from approximately $-80°$ C. to approximately $150°$ C., for example at from $-80$ to $-60°$ C., at room temperature, at from $-20$ to $40°$ C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

The invention relates also to those forms of the processes in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the processes of the present invention those starting materials are preferably used which result in compounds of formula I described as being preferred. Special preference is given to reaction conditions that are identical or analogous to those mentioned in the Examples. The invention relates also to novel starting compounds and intermediates described herein, especially those leading to novel compounds of the formula I or compounds of the formula I mentioned as preferred herein.

Pharmaceutical Use, Pharmaceutical Preparations and Methods

As described above, the compounds of the formula I are inhibitors of renin activity and, thus, may be of use for the treatment of hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, and the like. Hypertension, at least as one component of the disease to be treated, is especially preferred, meaning that hypertension alone or in combination with one or more (especially of the mentioned) other diseases may be treated (prophylactically and/or therapeutically).

The present invention further provides pharmaceutical compositions comprising a therapeutically effective amount of a pharmacologically active compound of the formula I, alone or in combination with one or more pharmaceutically acceptable carriers.

The pharmaceutical compositions according to the present invention are those suitable for enteral, such as oral or rectal, transdermal and parenteral administration to mammals, including man, to inhibit renin activity, and for the treatment of conditions associated with (especially inappropriate) renin activity. Such conditions include hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders and the like. Especially preferred is a disease which comprises hypertension, more especially hypertension itself, where treatment with a pharmaceutical composition or the use of a compound of the formula I for its synthesis is useful prophylactically and/or (preferably) therapeutically.

Thus, the pharmacologically active compounds of the formula I may be employed in the manufacture of pharmaceutical compositions comprising an effective amount thereof in conjunction or admixture with excipients or carriers suitable for either enteral or parenteral application. Preferred are tablets and gelatin capsules comprising the active ingredient together with:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and or polyvinylpyrrolidone; if desired
d) disintegrants, e.g., starches, agar, alginic acid or its sodium salt, or effervescent mixtures; and/or
e) absorbants, colorants, flavors and sweeteners.

Injectable compositions are preferably aqueous isotonic solutions or suspensions, and suppositories are advantageously prepared from fatty emulsions or suspensions.

Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Suitable formulations for transdermal application include a therapeutically effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound optionally with carriers, optionally a rate controlling barrier to deliver the compound of the skin of the host at a controlled and pre-determined rate over a prolonged period of time, and means to secure the device to the skin.

Accordingly, the present invention provides pharmaceutical compositions as described above for the treatment of conditions mediated by renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, as well as methods of their use.

The pharmaceutical compositions may contain a therapeutically effective amount of a compound of the formula I as defined herein, either alone or in a combination with another therapeutic agent, e.g., each at an effective therapeutic dose as reported in the art. Such therapeutic agents include:

a) antidiabetic agents such as insulin, insulin derivatives and mimetics; insulin secretagogues such as the sulfonylureas, e.g., Glipizide, glyburide and Amaryl; insulinotropic sulfonylurea receptor ligands such as meglitinides, e.g., nateglinide and repaglinide; peroxisome proliferator-activated receptor (PPAR) ligands; protein tyrosine phosphatase-1B (PTP-1B) inhibitors such as PTP-112; GSK3 (glycogen synthase kinase-3) inhibitors such as SB-517955, SB-4195052, SB-216763, N,N-57-05441 and N,N-57-05445; RXR ligands such as GW-0791 and AGN-194204; sodium-dependent glucose cotransporter inhibitors such as T-1095; glycogen phosphorylase A inhibitors such as BAY R3401; biguanides such as metformin; alpha-glucosidase inhibitors such as acarbose; GLP-1 (glucagon like peptide-1), GLP-1 analogs such as Exendin-4 and GLP-1 mimetics; and DPPIV (dipeptidyl peptidase IV) inhibitors such as LAF237;
b) hypolipidemic agents such as 3-hydroxy-3-methyl-glutaryl coenzyme A (HMG-CoA) reductase inhibitors, e.g., lovastatin, pitavastatin, simvastatin, pravastatin, cerivastatin, mevastatin, velostatin, fluvastatin, dalvastatin, atorvastatin, rosuvastatin and rivastatin; squalene synthase inhibitors; FXR (farnesoid X receptor) and LXR (liver X receptor) ligands; cholestyramine; fibrates; nicotinic acid and aspirin;

c) anti-obesity agents such as orlistat; and d) anti-hypertensive agents, e.g., loop diuretics such as ethacrynic acid, furosemide and torsemide; angiotensin converting enzyme (ACE) inhibitors such as benazepril, captopril, enalapril, fosinopril, lisinopril, moexipril, perinodopril, quinapril, ramipril and trandolapril; inhibitors of the Na—K-ATPase membrane pump such as digoxin; neutralendopeptidase (NEP) inhibitors; ACE/NEP inhibitors such as omapatrilat, sampatrilat and fasidotril; angiotensin II antagonists such as candesartan, eprosartan, irbesartan, losartan, telmisartan and valsartan, in particular valsartan; β-adrenergic receptor blockers such as acebutolol, atenolol, betaxolol, bisoprolol, metoprolol, nadolol, propranolol, sotalol and timolol; inotropic agents such as digoxin, dobutamine and milrinone; calcium channel blockers such as amlodipine, bepridil, diltiazem, felodipine, nicardipine, nimodipine, nifedipine, nisoldipine and verapamil; aldosterone receptor antagonists; and aldosterone synthase inhibitors.

Other specific anti-diabetic compounds are described by Patel Mona in *Expert Opin Investig Drugs,* 2003, 12(4), 623-633, in the FIGS. 1 to 7. A compound of the formula I may be administered either simultaneously, before or after the other active ingredient, either separately by the same or different route of administration or together in the same pharmaceutical formulation.

The structure of the therapeutic agents identified by code numbers, generic or trade names may be taken from the actual edition of the standard compendium "The Merck Index" or from databases, e.g., Patents International (e.g. IMS World Publications).

Accordingly, the present invention provides pharmaceutical products or compositions comprising a therapeutically effective amount of a compound of the formula I alone or in combination with a therapeutically effective amount of another therapeutic agent, preferably selected from anti-diabetics, hypolipidemic agents, anti-obesity agents and anti-hypertensive agents, most preferably from antidiabetics, anti-hypertensive agents and hypolipidemic agents as described above.

The present invention further relates to pharmaceutical compositions as described above for use as a medicament.

The present invention further relates to use of pharmaceutical compositions or combinations as described above for the preparation of a medicament for the treatment of conditions mediated by (especially inappropriate) renin activity, preferably, hypertension, atherosclerosis, unstable coronary syndrome, congestive heart failure, cardiac hypertrophy, cardiac fibrosis, cardiomyopathy postinfarction, unstable coronary syndrome, diastolic dysfunction, chronic kidney disease, hepatic fibrosis, complications resulting from diabetes, such as nephropathy, vasculopathy and neuropathy, diseases of the coronary vessels, restenosis following angioplasty, raised intra-ocular pressure, glaucoma, abnormal vascular growth and/or hyperaldosteronism, and/or further cognitive impairment, alzheimers, dementia, anxiety states and cognitive disorders, and the like.

Thus, the present invention also relates to a compound of formula I for use as a medicament, to the use of a compound of formula I for the preparation of a pharmaceutical composition for the prevention and/or treatment of conditions mediated by (especially inappropriate) renin activity, and to a pharmaceutical composition for use in conditions mediated by (especially inappropriate) renin activity comprising a compound of formula I, or a pharmaceutically acceptable salt thereof, in association with a pharmaceutically acceptable diluent or carrier material.

The present invention further provides a method for the prevention and/or treatment of conditions mediated by (especially inappropriate) renin activity, which comprises administering a therapeutically effective amount of a compound of the formula I to a warm-blooded animal, especially a human, in need of such treatment.

A unit dosage for a mammal of about 50-70 kg may contain between about 1 mg and 1000 mg, advantageously between about 5-600 mg of the active ingredient. The therapeutically effective dosage of active compound is dependent on the species of warm-blooded animal (especially mammal, more especially human), the body weight, age and individual condition, on the form of administration, and on the compound involved.

In accordance with the foregoing the present invention also provides a pharmaceutical product comprising a therapeutic combination, e.g., a kit, kit of parts, e.g., for use in any method as defined herein, comprising a compound of formula I, or a pharmaceutically acceptable salt thereof, to be used concomitantly or in sequence with at least one pharmaceutical composition comprising at least another therapeutic agent, preferably selected from anti-diabetic agents, hypolipidemic agents, anti-obesity agents or anti-hypertensive agents. The kit may comprise instructions for its administration.

Similarly, the present invention provides a kit of parts comprising: (i) a pharmaceutical composition comprising a compound of the formula I according to the invention; and (ii) a pharmaceutical composition comprising a compound selected from an anti-diabetic, a hypolipidemic agent, an anti-obesity agent, an anti-hypertensive agent, or a pharmaceutically acceptable salt thereof, in the form of two separate units of the components (i) to (ii).

Likewise, the present invention provides a method as defined above comprising co-administration, e.g., concomitantly or in sequence, of a therapeutically effective amount of a compound of formula I, or a pharmaceutically acceptable salt thereof, and at least a second drug substance, said second drug substance preferably being an anti-diabetic, a hypolipidemic agent, an anti-obesity agent or an anti-hypertensive agent, e.g., as indicated above.

Preferably, a compound of the invention is administered to a mammal in need thereof.

Preferably, a compound of the invention is used for the treatment of a disease which responds to a modulation of (especially inappropriate) renin activity, especially one or more of the specific diseases mentioned above.

Finally, the present invention provides a method or use which comprises administering a compound of formula I in combination with a therapeutically effective amount of an anti-diabetic agent, a hypolipidemic agent, an anti-obesity agent or an anti-hypertensive agent.

Ultimately, the present invention provides a method or use which comprises administering a compound of formula I in the form of a pharmaceutical composition as described herein.

The above-cited properties are demonstrable in vitro and in vivo tests using advantageously mammals, e.g., mice, rats, rabbits, dogs, monkeys or isolated organs, tissues and preparations thereof. Said compounds can be applied in vitro in the form of solutions, e.g., preferably aqueous solutions, and in vivo either enterally, parenterally, advantageously intravenously, e.g., as a suspension or in aqueous solution. The concentration level in vitro may range between about $10^{-3}$ molar and $10^{-10}$ molar concentrations. A therapeutically effective amount in vivo may range depending on the route of administration, between about 0.001 and 500 mg/kg, preferably between about 0.1 and 100 mg/kg.

As described above, the compounds of the present invention have enzyme-inhibiting properties. In particular, they inhibit the action of the natural enzyme renin. Renin passes from the kidneys into the blood where it effects the cleavage of angiotensinogen, releasing the decapeptide angiotensin I which is then cleaved in the lungs, the kidneys and other organs to form the octapeptide angiotensin II. The octapeptide increases blood pressure both directly by arterial vasoconstriction and indirectly by liberating from the adrenal glands the sodium-ion-retaining hormone aldosterone, accompanied by an increase in extracellular fluid volume which increase can be attributed to the action of angiotensin II. Inhibitors of the enzymatic activity of renin lead to a reduction in the formation of angiotensin I, and consequently a smaller amount of angiotensin II is produced. The reduced concentration of that active peptide hormone is a direct cause of the hypotensive effect of renin inhibitors.

The action of renin inhibitors may be demonstrated inter alia experimentally by means of in vitro tests, the reduction in the formation of angiotensin I being measured in various systems (human plasma, purified human renin together with synthetic or natural renin substrate).

Inter alia the following in vitro tests may be used:

1) Recombinant human renin (expressed in Chinese Hamster Ovary cells and purified using standard methods) at 7.5 nM concentration is incubated with test compound at various concentrations for 1 h at RT in 0.1 M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 2 µM and increase in fluorescence is recorded at an excitation wave-length of 350 nm and at an emission wave-length of 500 nm in a microplate spectro-fluorimeter. IC50 values are calculated from percentage of inhibition of renin activity as a function of test compound concentration (Fluorescence Resonance Energy Transfer, FRET, assay). Compounds of the formula I, in this assay, preferably can show $IC_{50}$ values in the range from 1 nM to 20 µM.

2) Alternatively, recombinant human renin (expressed in Chinese Hamster Ovary cells and purified using standard methods) at 0.5 nM concentration is incubated with test compound at various concentrations for 2 h at 37° C. in 0.1 M Tris-HCl buffer, pH 7.4, containing 0.05 M NaCl, 0.5 mM EDTA and 0.05% CHAPS. Synthetic peptide substrate Arg-Glu(EDANS)-Ile-His-Pro-Phe-His-Leu-Val-Ile_His_Thr-Lys(DABCYL)-Arg9 is added to a final concentration of 4 µM and increase in fluorescence is recorded at an excitation wave-length of 340 nm and at an emission wave-length of 485 nm in a microplate spectro-fluorimeter. IC50 values are calculated from percentage of inhibition of renin activity as a function of test compound concentration (Fluorescence Resonance Energy Transfer, FRET, assay). Compounds of the formula I, in this assay, preferably can show $IC_{50}$ values in the range from 1 nM to 20 µM.

3) In another assay, human plasma spiked with recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I, in this assay, preferably can show $IC_{50}$ values in the range from 1 nM to 20 µM.

4) In another assay, recombinant human renin (expressed in Chinese Hamster Ovary cells and purified using standard methods) at 0.8 nM concentration is incubated with test compound at various concentrations for 2 h at 37° C. in 0.1 M Tris/HCl pH 7.4 containing 0.05 M NaCl, 0.5 mM EDTA and 0.025% (w/v) CHAPS. Synthetic peptide substrate Ac-Ile-His-Pro-Phe-His-Leu-Val-Ile-His-Asn-Lys-[DY-505-X5] is added to a final concentration of 2.5 µM. The enzyme reaction is stopped by adding an excess of a blocking inhibitor. The product of the reaction is separated by capillary electrophoresis and quantified by spectrophotometric measurement at 505 nM wave-length. IC50 values are calculated from percentage of inhibition of renin activity as a function of test compound concentration. Compounds of the formula I, in this assay, preferably show $IC_{50}$ values in the range from 1 nM to 20 µM.

In animals deficient in salt, renin inhibitors bring about a reduction in blood pressure. Human renin may differ from the renin of other species. In order to test inhibitors of human renin, primates, e.g., marmosets (*Callithrix jacchus*) may be used, because human renin and primate renin are substantially homologous in the enzymatically active region. Inter alia the following in vivo tests may be used:

Compounds of the formula I can be tested in vivo in primates as described in the literature (see for example by Schnell C R et al. Measurement of blood pressure and heart rate by telemetry in conscious, unrestrained marmosets. Am J Physiol 264 (Heart Circ Physiol 33). 1993: 1509-1516; or Schnell C R et al. Measurement of blood pressure, heart rate, body temperature, ECG and activity by telemetry in conscious, unrestrained marmosets. Proceedings of the fifth FELASA symposium: Welfare and Science. Eds BRIGHTON. 1993.

It has been found that the new compounds, beside being potent renin inhibitors, also show an improved bioavailability, The bioavailability is preferably equal to or higher than 20%, more preferably equal to or higher than 30%. The bioavailability can be determined as follows.

Pharmacokinetic profiles are investigated in male Sprague-Dawley rats implanted with jugular vein catheters. Compounds are administered orally in 0.5% aqueous methylcellulose solution or intravenously in N-methylpyrrolidinone-PEG200 (10:90, v/v). Typical doses are 6 mg/kg p.o. and 2 mg/kg i.v., respectively. Blood samples are serially taken through venous catheters into heparinized tubes at various time points until 32 h post dose and plasma is separated by centrifugation. Plasma concentrations of the compounds described in this invention are measured by liquid chromatography-tandem mass spectrometry after extraction with acetonitrile.

Pharmacokinetic parameters are calculated by using a non-compartmental method.

ABBREVIATIONS

Boc tert-butoxycarbonyl
BopCl bis(2-oxo-3-oxazolidinyl)phosphinic chloride
CAN ammonium cerium (IV) nitrate
DMF N,N-dimethylformamide DMSO dimethylsulfoxide
EDCl.HCl 1-[3-(dimethylamino)propyl]-3-ethylcarbodiimide hydrochloride
Et ethyl
EtOAc ethyl acetate
h hour(s)
HOAT 1-hydroxy-7-azabenzotriazole
mL milliliter
Me methyl
MS mass spectrometry
NMP N-methylpyrrolidinone
Ph phenyl
i-Pr isopropyl
RT room temperature
TcBocCl 2,2,2-trichloro-1,1-dimethylethyl chloroformate
TFA trifluoroacetic acid
THF tetrahydrofuran
TLC thin layer chromatography
$t_R$ retention time Temperatures are measured in degrees Celsius. Unless otherwise indicated, the reactions take place at RT. Unless otherwise indicated, the hydrogenation reactions in the presence of $H_2$ take place at atmospheric pressure. The microwave irradiation is performed by using a "Biotage Initiator 60" machine.

HPLC Condition-A:
Column: CombiScreen ODS-AM, 50×4.6 mm.
Flow rate: 2.0 mL/min
Mobile phase: A) TFA/water (0.1/100, v/v), B) TFA/acetonitrile (0.1/100, v/v)
Gradient: linear gradient from 5% B to 100% B in 5 min then 100% B in 2 min
Detection: UV at 215 nm HPLC Condition-B:
Column: ACQUITY HPLC™ BEH $C_{18}$ 1.7 μm, 50×2.1 mm.
Flow rate: 0.5 mL/min
Mobile phase: A) TFA/water (0.1/100, v/v), B) TFA/acetonitrile (0.1/100, v/v)
Gradient: 5% B in 0.5 min then linear gradient from 5% B to 100% B in 1.5 min then 100% B in 1.0 min
Detection: UV at 215 nm HPLC Condition-C:
Column: ACQUITY HPLC™ BEH $C_{18}$ 1.7 μm, 50×2.1 mm.
Flow rate: 0.5 mL/min
Mobile phase: A) TFA/water (0.1/100, v/v), B) TFA/acetonitrile (0.1/100, v/v)
Gradient: 5% B in 0.5 min then linear gradient from 5% B to 100% B in 5.0 min then 100% B in 1.5 min
Detection: UV at 215 nm TLC conditions: $R_f$ values for TLC are measured on 5×10 cm TLC plates, silica gel $F_{254}$, Merck, Darmstadt, Germany.

Methods for preparing compounds of formula I are described in detail below. It should be noted that the brief description on each of the arrows for each conversion has been added for illustration purposes only and should not be regarded as limiting with respect to the sequence or each individual step.

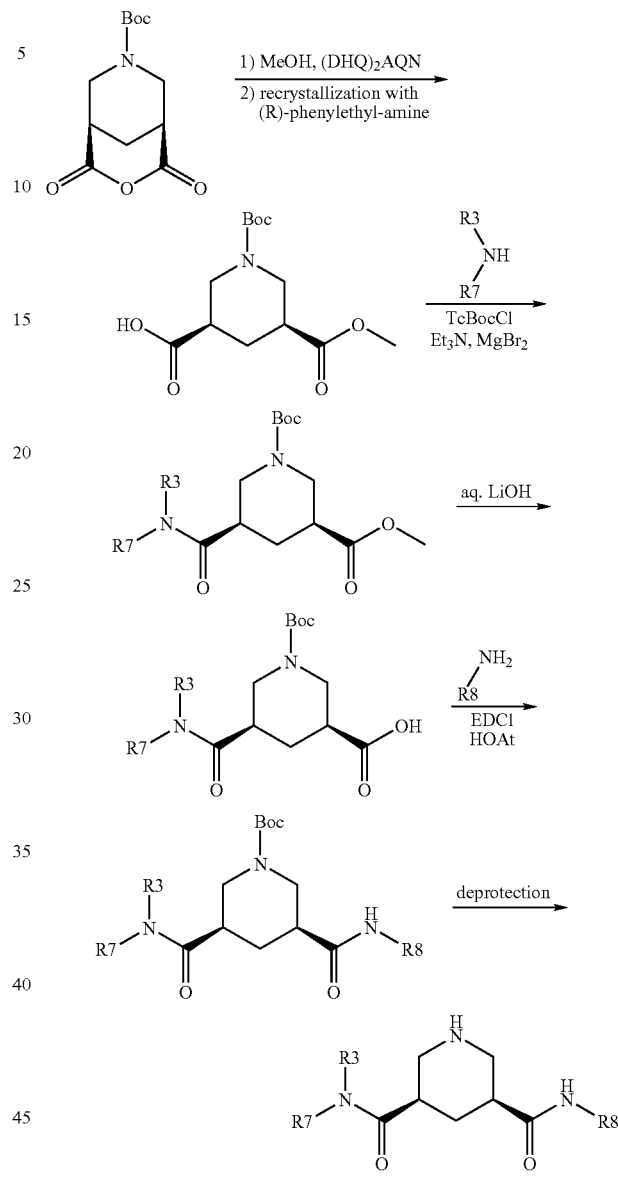

Scheme 1a

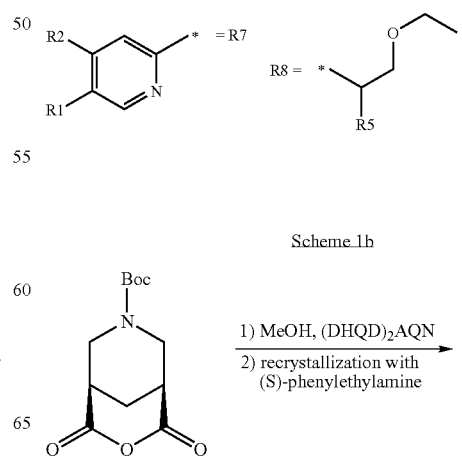

Scheme 1b

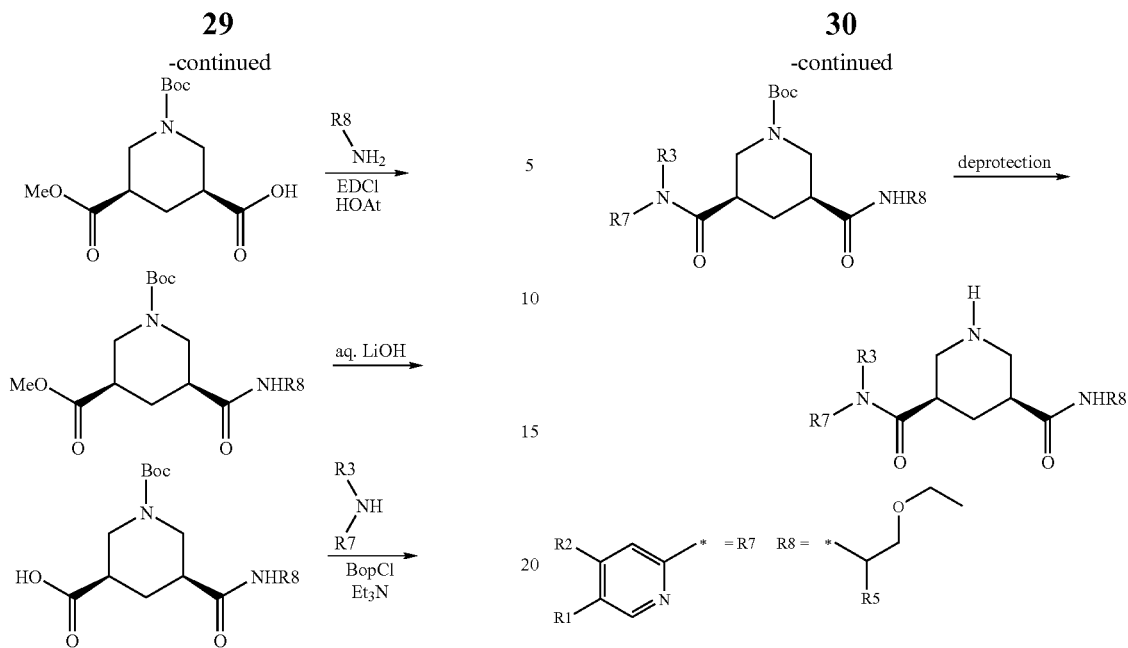
Scheme 2
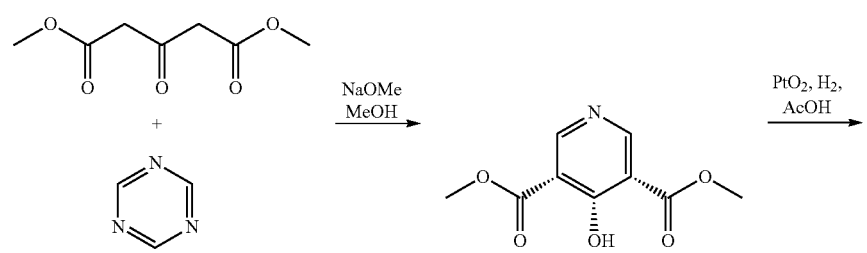
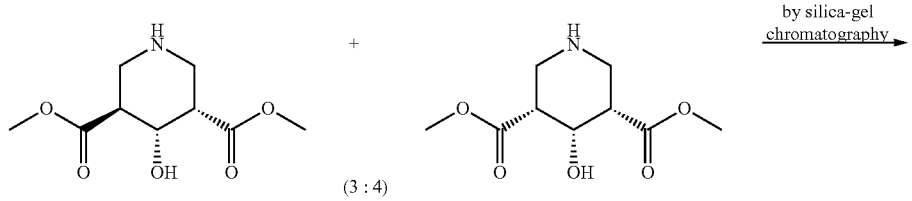
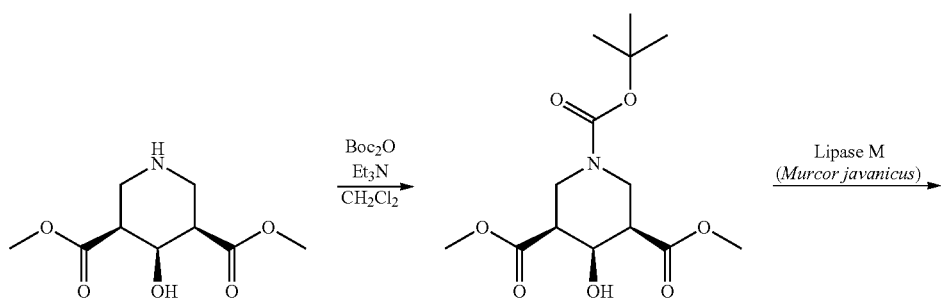

-continued
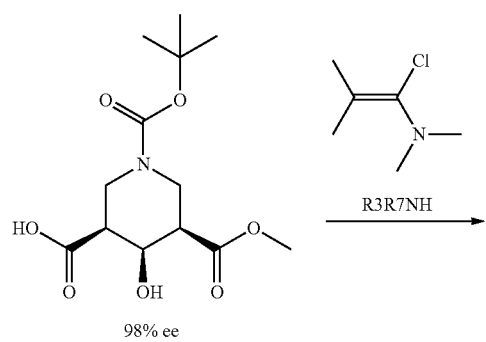
98% ee
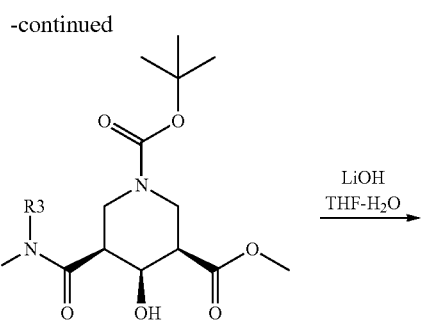
LiOH
THF-H$_2$O
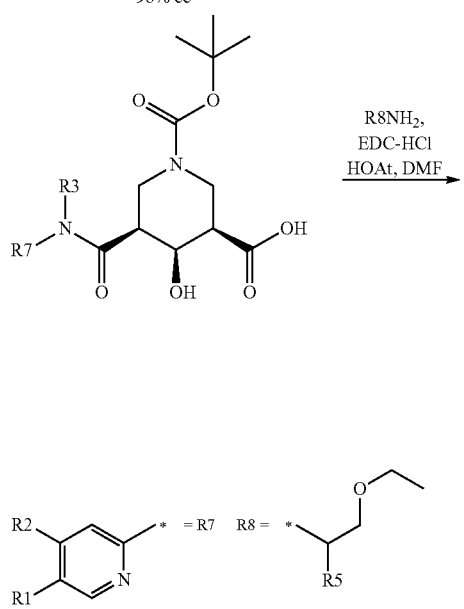
R8NH$_2$,
EDC-HCl
HOAt, DMF
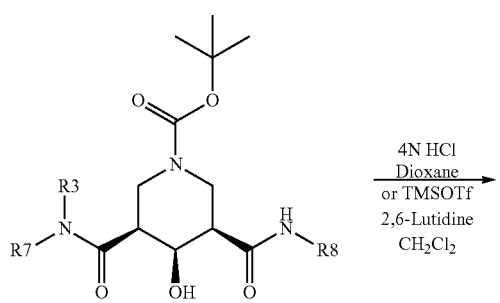
4N HCl
Dioxane
or TMSOTf
2,6-Lutidine
CH$_2$Cl$_2$
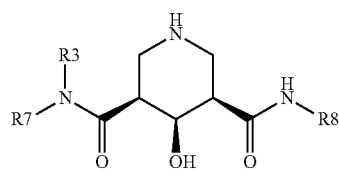
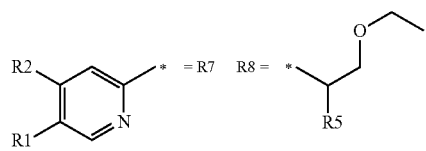
Scheme 3 (preparation of the cyclic anhydride shown as starting material in Schemes 1a and 1b)
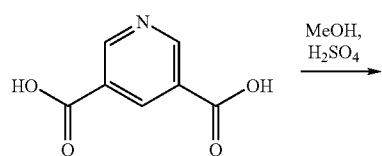
MeOH,
H$_2$SO$_4$
-continued
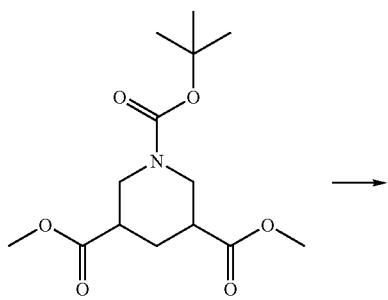
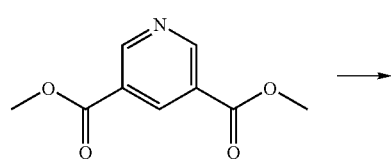
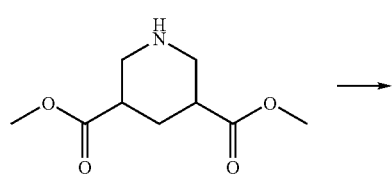
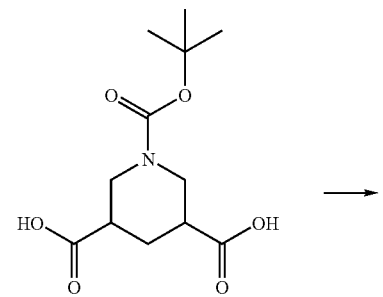

-continued

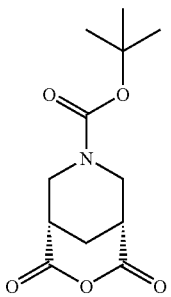

A: Pyridine-3,5-dicarboxylic acid dimethyl ester

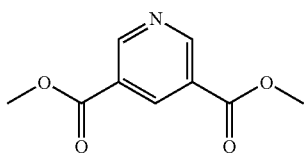

3,5-Pyridinedicarboxylic acid (1.5 g, 63 mmol) and conc. H$_2$SO$_4$ (0.9 mL) in MeOH (15 mL) are heated in a microwave oven at 120° C. for 2 h. The solvent is evaporated to give a residue which is partitioned between ethyl acetate and sat. aq. NaHCO$_3$. The organic phase is washed with brine, dried over Na$_2$SO$_4$, filtered and evaporated to give a light yellow solid.

MS (LC-MS): 196 [M+H]$^+$ TLC, Rf (ethyl acetate/hexane 1:1)=0.56.

B: Piperidine-3,5-dicarboxylic acid dimethyl ester

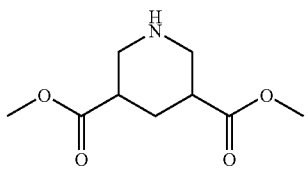

Pyridine-3,5-dicarboxylic acid dimethyl ester (5.3 g, 27 mmol) and Rh/PtO$_2$ (0.5 g) in MeOH (200 mL) are stirred under hydrogen overnight. The resulting mixture is filtered and the solvents are evaporated to give a brown oil. MS (LC-MS): 202 [M+H]$^+$ C: Piperidine-1,3,5-tricarboxylic acid 1-tert-butyl ester 3,5-dimethyl ester

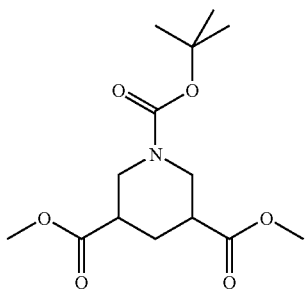

A solution of piperidine-3,5-dicarboxylic acid dimethyl ester (5.4 g, 26.8 mmol) in CH$_2$Cl$_2$ (55 mL) is treated with Boc$_2$O (6.4 g, 29.5 mmol) and the reaction is stirred at rt overnight. The reaction is quenched with 0.1N aq. HCl and the organic phase is washed with 0.1N aq HCl. The combined aqueous phases are extracted 2 times with CH$_2$Cl$_2$/MeOH (9/1) before the combined organic phases are dried over Na$_2$SO$_4$, filtered and evaporated. The resulting residue is purified by flash chromatography on silica gel (eluent: CH$_2$Cl$_2$/MeOH 95:5) to give the title compound as a yellow solid. MS (LC-MS): 302 [M+H]$^+$. TLC, Rf (CH$_2$Cl$_2$/MeOH 95:5)=0.5.

D: Piperidine-1,3,5-tricarboxylic acid 1-tert-butyl ester

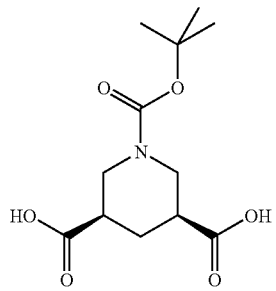 [SMILES: CC(C)(C)OC(=O)N1C[C@H](C(=O)O)C[C@H](C(=O)O)C1]

To a solution of piperidine-1,3,5-tricarboxylic acid 1-tert-butyl ester 3,5-dimethyl ester (6.8 g, 22.5 mmol) in MeOH/water (4:1, 120 mL) is added K$_2$CO$_3$ (9.4 g, 68 mmol). The reaction mixture is stirred at reflux overnight. The MeOH is evaporated and the residue is extracted with dicholoromethane and 1N aq. HCl. The organic phase is dried over Na$_2$SO$_4$, filtered and evaporated to give a light yellow solid. MS (LC-MS): 274 [M+H]$^+$.

E: 2,4-Dioxo-3-oxa-7-aza-bicyclo[3.3.1]nonane-7-carboxylic acid tert-butyl ester

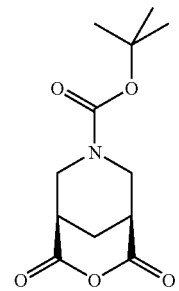 [SMILES: CC(C)(C)OC(=O)N1C[C@H]2C[C@@H](C1)C(=O)OC2=O]

A suspension of piperidine-1,3,5-tricarboxylic acid 1-tert-butyl ester (1 g, 3.6 mmol) in acetic anhydride (20 mL) is heated at reflux for 2 h. The reaction mixture is evaporated three times with toluene before it is dried under high vacuum at rt overnight to give a yellow solid. MS (LC-MS): 278 [M+Na]$^+$.

(3S, 5R)-starting material-F

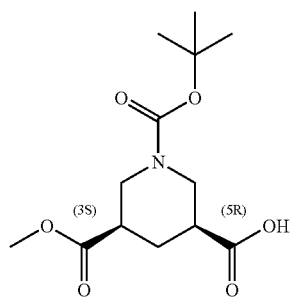 [SMILES: COC(=O)[C@@H]1C[C@H](C(=O)O)CN(C(=O)OC(C)(C)C)C1]

To a solution of (3S, 5R)-starting material-F (67% ee) (47 g, 162 mmol) in hot EtOH (162 mL) is added (S)-(−)-1-phenylethylamine (20.6 mL, 162 mmol) at 80° C. The solution is cooled to r.t. and allowed to stand for overnight, which results in the precipitation of a salt. The salt is collected by filtration. After repeating the same recrystallization procedure in EtOH three times, the resulting salt is dissolved in water, acidified with 5N and 1N HCl, and extracted with AcOEt. The combined organic phases are washed with brine, dried over MgSO$_4$. Concentration under reduced pressure gives (3S, 5R)-starting material-F: colorless crystal; ES-MS: M+H=288: $_B$t$_{Ret}$=2.67 min. chiral HPLC (column: CHIRALPAH AD-H (0.46 cm×25 cm), eluent: hexane/i-PrOH/0.1% TFA=95/5, flow rate: 0.5 mL/min, detection: UV 210 nm, temperature: rt) t$_R$=37 min (3S, 5R)-Starting material-F (98% ee)

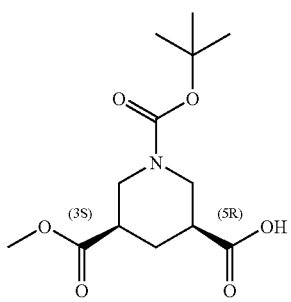 [SMILES: COC(=O)[C@@H]1C[C@H](C(=O)O)CN(C(=O)OC(C)(C)C)C1]

To the solution of starting material-E (401.5 mg, 1.57 mmol) and commercially available (DHQD)$_2$AQN (423.6 mg, 0.47 mmol, 95% purity)$^a$ in Et$_2$O (60 mL) and THF (20 mL) under N$_2$ is added MeOH (0.64 mL, 15.67 mmol) at −40° C. After stirring at that temperature for 24 h, sat. citric acid aq. is added. The reaction mixture is extracted with EA. The organic phase is washed with brine, dried over Na$_2$SO$_4$ and subjected to silica chromatography to give (3S, 5R)-starting material-F in 98% ee as a white amorphous material ES-MS: M+H-tBu=232; HPLC: $_C$t$_{Ret}$=2.73 min. chiral HPLC (column: CHIRALPAH AD-H (0.46 cm×25 cm), eluent: hexane/i-PrOH=95/5, flow rate: 0.5 mL/min, detection: UV 210 nm, temperature: rt) t$_R$=33.25 min $^a$ Chen, Y.; Tian, S-K.; Deng, Li. *J. Am. Chem. Soc.* 2000, 122, 9542-9543.

(3R, 5S)-starting material-F, 35.56 min for (3S, 5R)-starting material-F, (3R, 5S)-Starting material-F

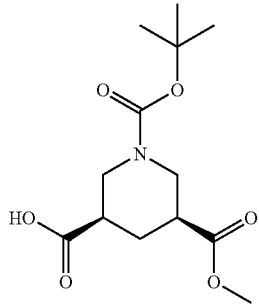 [SMILES: COC(=O)[C@H]1C[C@@H](C(=O)O)CN(C(=O)OC(C)(C)C)C1]

To a solution of (3R, 5S)-starting material-F (72% ee) (4.2 g, 14.6 mmol) in hot EtOH (20 mL) is added (R)-1-phenylethylamine (1.79 g, 14.76 mmol) at 70° C. The solution is cooled to rt and allowed to stand for 1 h, which results in the precipitation of a salt. The salt is collected by filtration. After repeating the same recrystallization procedure three times, the resulting salt was dissolved in water, acidified with 1M HClaq and extracted five times with ether. The combined organic phases are washed with brine, dried with MgSO$_4$. Concentration under reduced pressure gives (3R, 5S)-starting material-F: colorless crystal; ES-MS: M+H=288: $_B$t$_{Ret}$=2.67 min. chiral HPLC: AD-H, 5% i-PrOH/Hexane, flow 0.5 mL/min, 210 nm, t$_{Ret}$=33 (major), 36 (minor).

(3R, 5S)-starting material-F (72% ee)

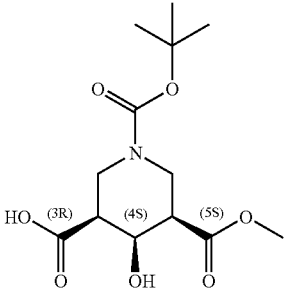

To a solution of starting material-E (200 mg, 0.78 mmol) in THF (10 mL) and ether (30 mL) is added (DHQ)$_2$AQN (67 mg, 0.08 mmol) and MeOH (0.32 mL) at 0° C. under N$_2$. The resulting mixture is stirred for 5 h at 0° C. After adding 1M HCl aq, the mixture is extracted with EtOAc. The organic phases are washed with brine and dried with MgSO$_4$. Concentration under reduced pressure and silica gel flash chromatography give (3R, 5S)-starting material-F: ES-MS: M+H=288: $_C$t$_{Ret}$=2.67 min. chiral HPLC: 72% ee, AD-H, 5% i-PrOH/Hexane, flow 0.5 mL/min, 210 nm, t$_{Ret}$=33 (major), 36 (minor).

(3R,4S,5S)-starting material-G ((3R,4S,5S)—N-tert-Butyloxycarbonyl-4-hydroxy-piperidine-3,5-dicarboxylic acid 3-methyl ester)

A mixture of (3R,4S,5S), and (3S,4R,5R), -N-tert-Butyloxycarbonyl-4-hydroxy-piperidine-3,5-dicarboxylic acid 3-methyl ester (96% ee) (78 g, 0.26 mol) is dissolved in MeOH (500 mL) and (S)-(−)1-phenylethylamine (33 mL, 0.26 mol) at room temperature is added. The mixture is stirred for 30 min at room temperature and concentrated under reduced pressure to provide a salt as a colorless amorphous. The resulting residue is dissolved in CH$_3$CN (1.3 L) at 70° C. and stirred vigorously at room temperature for 20 h. A white crystalline salt is collected by filtration, washed with Et$_2$O. After repeating the same recrystallization procedure (dissolution in CH$_3$CN and stirring at room temperature) two or three times the resulting salt is dissolved in water, acidified to pH 3 with 5N and 1N HCl, and extracted with AcOEt. The combined organic phases are dried over Na$_2$SO$_4$. Concentration under reduced pressure gives enantiomeric pure (3R,4S,5S)-starting material-G as a white solid: ES-MS: M+H=304: $_c$t$_{Ret}$=2.37 min. chiral HPLC: >99.9% ee, AD-H, 7.5% i-PrOH/Hexane/0.1% TFA, flow 0.75 mL/min, 210 nm, t$_{Ret}$=24 min (3R,4S,5S)-starting material-G (96% ee)

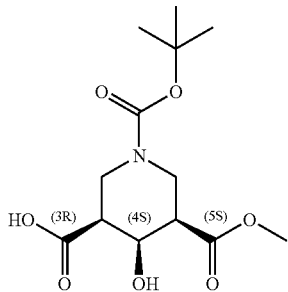 [SMILES: COC(=O)[C@@H]1CN(C(=O)OC(C)(C)C)C[C@H](C(=O)O)[C@@H]1O]

To a solution of (3,4-cis-4,5-cis)-N-tert-Butyloxycarbonyl-4-hydroxy-piperidine-3,5-dicarboxylic acid dimethyl ester (18 g, Liang, X.; Lohse, A.; Bols, M. *J. Org. Chem.* 2000, 65, 7432.) in phosphate buffer (0.2M, pH 7.5, 540 mL) is added Lipase M (*Mucor javanicus*) (5.4 g) at room temperature. The reaction mixture is stirred for 6 days at 35° C. and then acidified to pH 3 with 5N and 1N HCl. The mixture is extracted with EtOAc, the organic phases are dried with Na$_2$SO$_4$ Concentration under reduced pressure gives (3R,4S,5S)-starting material-G as a white solid: ES-MS: M+H=304: $_c$t$_{Ret}$=2.37 min. chiral HPLC: 95.8% ee, AD-H, 7.5% i-PrOH/Hexane/0.1% TFA, flow 0.75 mL/min, 210 nm, t$_{Ret}$=24 min (3R,4S,5S), 26 min (3S,4R,5R).

EXAMPLE 1

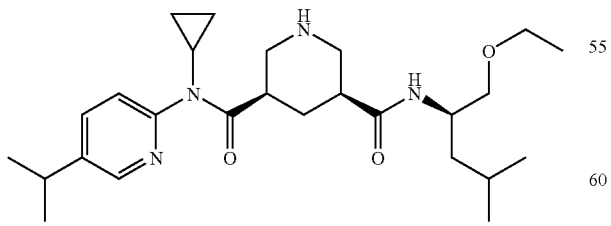

A mixture of Intermediate 1.1 (70 mg, 0.125 mmol) in 4N HCl in dioxane (2 mL) is stirred at room temperature. After stirring for 1 h, the reaction mixture is concentrated in vacuo to give Example 1: ES-MS: M+H=459: $_c$t$_{Ret}$=3.26 min.

Intermediate 1.1

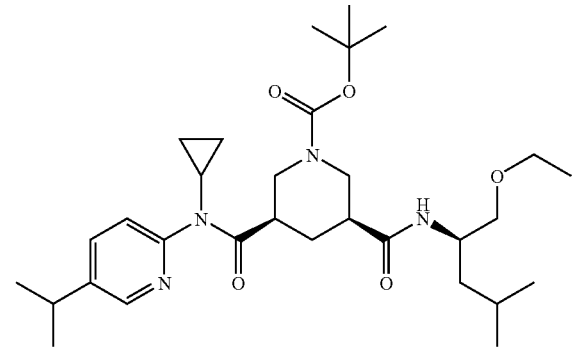 [SMILES: CCOC[C@@H](CC(C)C)NC(=O)[C@H]1C[C@@H](C(=O)N(c2ccc(C(C)C)cn2)C2CC2)CN(C(=O)OC(C)(C)C)C1]

To a solution of Intermediate 1.4 (27 mg, 0.150 mmol) and Intermediate 1.9 (50 mg, 0.125 mmol) in CH$_2$Cl$_2$ are added BopCl (47 mg, 0.188) and Et$_3$N (19 mg, 0.188 mmol). After stirring for 16 h at room temperature, the reaction mixture is diluted with H$_2$O (10 mL) and extracted with EtOAc (50 mL). The organic phase is successively washed with 5% NaHCO$_3$aq, H$_2$O, and brine, then dried over Na$_2$SO$_4$. The organic phase is concentrated in vacuo to give the crude residue, which is purified by SiO$_2$ column chromatography to give Intermediate 1.1 as a white amorphous material; ES-MS: M+H=559; HPLC: $_c$t$_{Ret}$=4.23 min.

Intermediate 1.2

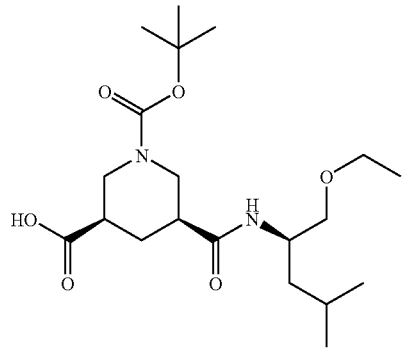 [SMILES: CCOC[C@@H](CC(C)C)NC(=O)[C@H]1C[C@@H](C(=O)O)CN(C(=O)OC(C)(C)C)C1]

To a solution of Intermediate 1.3 (450 mg, 1.09 mmol) in THF/H$_2$O (5/5 mL) is added LiOH.H$_2$O (84 mg, 2 mmol) at 0° C. After stirring for 1 h at the same temperature, the reaction is quenched by 5% aqueous KHSO$_4$ (20 mL) and extracted with EtOAc (200 mL). The organic phase is washed with H$_2$O and brine, then dried over Na$_2$SO$_4$. The organic phase is concentrated in vacuo to give Intermediate 1.2 as a white amorphous material; ES-MS: M+H=401: $_c$t$_{Ret}$=3.30.

Intermediate 1.3

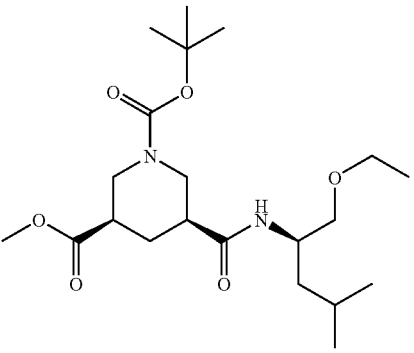 [SMILES: CCOC[C@@H](CC(C)C)NC(=O)[C@H]1C[C@@H](C(=O)OC)CN(C(=O)OC(C)(C)C)C1]

Intermediate 1.3 is synthesized by coupling reaction of Intermediate 1.7 with (3S, 5R)-starting material-F analogously to the preparation of Intermediate 1.1: ES-MS: M+H=415: $_c t_{Ret}$=3.69 min.

Intermediate 1.4

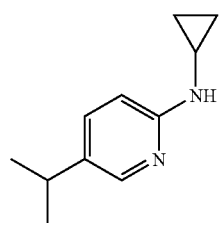

To a solution of Intermediate 1.5 (230 mg, 1.20 mmol) in CH$_2$Cl$_2$ (10 mL) are added Et$_3$SiH (728 mg, 6.26 mmol) and TFA (1.48 g, 12.9 mmol) at 0° C., then the mixture is stirred at room temperature. After stirring for 15 h, the reaction mixture is concentrated in vacuo. The residue is suspended in 5% aqueous NaHCO$_3$ and extracted with CH$_2$Cl$_2$. The organic phase is washed with H$_2$O and brine, then dried over Na$_2$SO$_4$. The organic phase is concentrated in vacuo and the resulting residue is purified by SiO$_2$ column chromatography to give Intermediate 1.4 as a white amorphous material; ES-MS: M+H=177; HPLC: $_c t_{Ret}$=2.24 min.

Intermediate 1.5

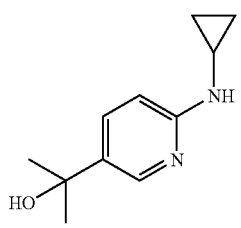

To a solution of Intermediate 1.6 (300 mg, 1.45 mmol) in THF (10 mL) is added MeLi (1M in Et$_2$O, 7.25 mmol) at 0° C., then the mixture is stirred at room temperature. After stirring for 1 h, the reaction mixture is cooled down to 0° C. and quenched with 5% aqueous NaHCO$_3$ (50 mL). The reaction mixture is then extracted with EtOAc (200 mL). The organic phase is washed with H$_2$O and brine, and then dried over Na$_2$SO$_4$. The organic phase is concentrated in vacuo to give the crude residue, which is purified by SiO$_2$ column chromatography to give Intermediate 1.5 as a white amorphous material; ES-MS: M+H=193; HPLC: $_c t_{Ret}$=1.74 min.

Intermediate 1.6

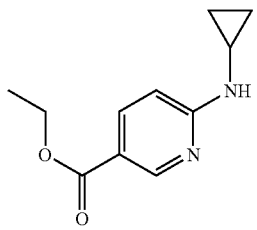

To a solution of 6-chloronicotinic acid ethyl ester (1 g, 5.4 mmol) in NMP (10 mL) are added cyclopropylamine (4.12 g, 72.2 mmol) and K$_2$CO$_3$ (2.2 g, 16 mmol) at room temperature, then the mixture is stirred at 70° C. After stirring for 12 h, the reaction mixture is cooled down to room temperature and quenched with H$_2$O (100 mL). The reaction mixture is extracted with EtOAc (200 mL). The organic phase is washed with H$_2$O and brine, then dried over Na$_2$SO$_4$. The organic phase is concentrated in vacuo to give the crude residue, which is recrystallized from n-hexane/Et$_2$O to give Intermediate 1.6 as a white amorphous material; ES-MS: M+H=207; HPLC: $_c t_{Ret}$=1.98 min.

Intermediate 1.7

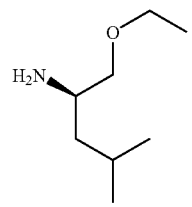

Intermediate 1.7 is synthesized by deprotection of Intermediate 1.8 analogously to the preparation of Example 1: ES-MS: M+H=146: $_B t_{Ret}$=1.32 min.

Intermediate 1.8

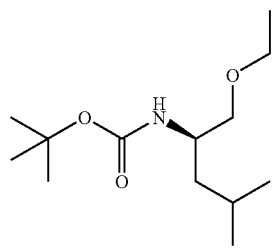 [SMILES: CCOC[C@@H](CC(C)C)NC(=O)OC(C)(C)C]

To a solution of Boc-D-Leucinol (277.9 mg, 1.278 mmol) in DMF (5 mL) under N$_2$ at 0° C. is added NaH (80.3 mg of 60 wt % in mineral oil, 2.00 mmol). After stirring at the same temperature for a few min, EtI (0.122 mL, 1.53 mmol) is added. The resulting solution is stirred at rt for 2 h. The reaction is quenched with H$_2$O and the mixture is extracted with EtOAc, and dried over Na$_2$SO$_4$. Concentration under reduced pressure gives the crude product. The crude product is purified by silica gel chromatography to afford Intermediate 1.8: ES-MS: M+H-Boc=146: $_B t_{Ret}$=2.11 min.

EXAMPLE 2

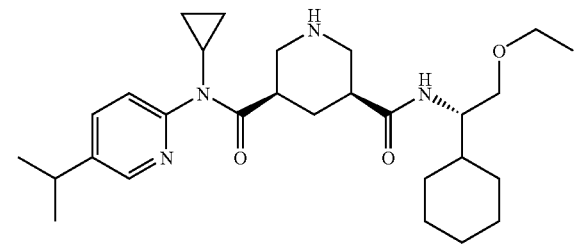 [SMILES: CCOC[C@@H](NC(=O)[C@@H]1CNC[C@H](C(=O)N(c2ccc(C(C)C)cn2)C2CC2)C1)C1CCCCC1]

A solution of Intermediate 2.1 (194.2 mg, 0.33 mmol) in 4N HCl in EtOAc (3 mL) under N$_2$ is stirred at RT for 35 min. Concentration under the reduced pressure gives Example 2 as a white amorphous material: ES-MS: M+H=485: $_c t_{Ret}$=3.08 min.

Intermediate 2.1

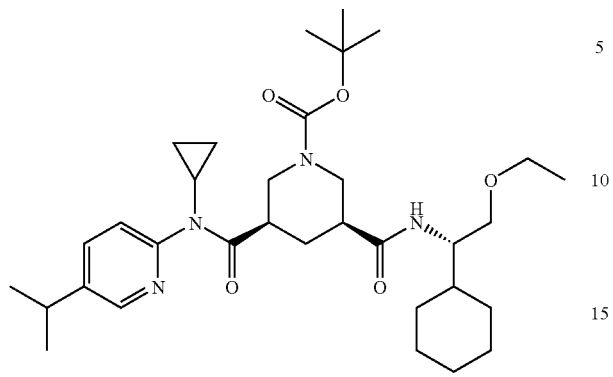

To a solution of Intermediate 2.2 (153.8 mg, 0.356 mmol) in CH$_2$Cl$_2$ (5 mL) under N$_2$ at RT are added EDCl.HCl (95 mg, 0.42 mmol) and HOAt (70 mg, 0.51 mmol). The resulting solution is stirred at the same temperature for 15 min. Then, a solution of Intermediate 2.4 (73 mg, 0.35 mmol) and triethylamine (0.25 mL, 1.78 mmol) in CH$_2$Cl$_2$ (3 ml) is slowly added at 0° C. The solution is stirred at RT for 60 min. Concentration under reduced pressure gives the crude residue, which is purified by silica gel chromatography to afford Intermediate 2.1 as a white amorphous material; ES-MS: M=585; HPLC: $_c$t$_{Ret}$=4.78 min.

Intermediate 2.2

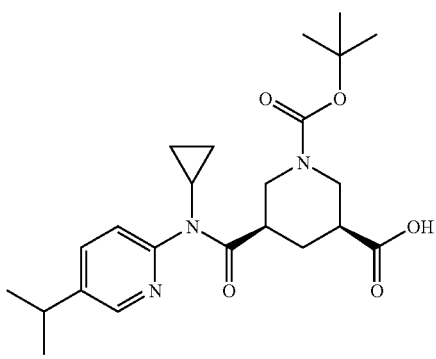 [SMILES: CC(C)c1ccc(N(C(=O)[C@@H]2C[C@H](C(=O)O)CN(C(=O)OC(C)(C)C)C2)C2CC2)nc1]

To a solution of Intermediate 2.3 (160 mg, 0.359 mmol) in THF/H$_2$O (5/5 mL) is added LiOH.H$_2$O (29 mg, 0.691 mmol) at 0° C. After stirring for 1 h at the same temperature, the reaction is quenched by 5% aqueous KHSO$_4$ (20 mL) and extracted with CH$_2$Cl$_2$ (50 mL). The organic phase is washed with H$_2$O and brine, then dried over Na$_2$SO$_4$. The organic phase is concentrated in vacuo to give Intermediate 2.2 as a white amorphous material; ES-MS: M+H=432; HPLC: $_c$t$_{Ret}$=3.50 min.

Intermediate 2.3

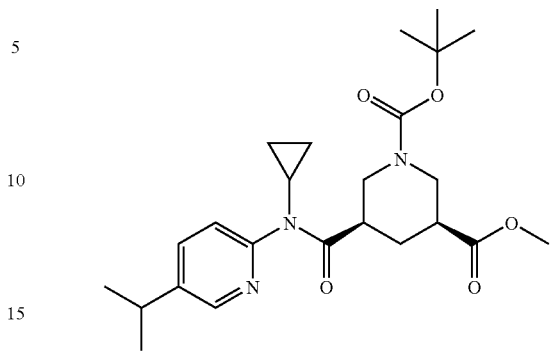

To a solution of (3R, 5S)-starting material-F (293 mg, 1.02 mmol) in THF (10 mL) are added Et$_3$N (206 mg, 2.04 mmol) and TcBocCl (488 mg, 2.04 mmol) at 0° C. After stirring for 1 h at the same temperature, MgBr$_2$.Et$_2$O (527 mg, 2.04 mmol) and Intermediate 1.4 (180 mg, 1.02 mmol) are added at 0° C., then the mixture is stirred at room temperature. After stirring for 3 h, the reaction is quenched with 5% aqueous KHSO$_4$ (50 mL) and extracted with EtOAc (100 mL). The organic phase is washed with H$_2$O and brine, and then dried over Na$_2$SO$_4$. The organic phase is concentrated in vacuo and the resulting residue is purified by SiO$_2$ column chromatography to give Intermediate 2.3 as a white amorphous material; ES-MS: M+H=446; HPLC: $_c$t$_{Ret}$=3.86 min.

Intermediate 2.4

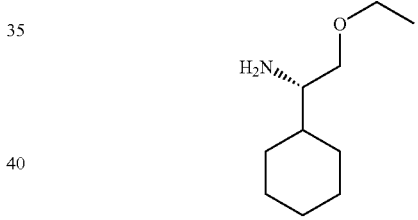

Intermediate 2.4 is synthesized by deprotection of Intermediate 2.5 analogously to the preparation of Example 1. ES-MS: M+H=172: $_B$t$_{Ret}$=1.55 min.

Intermediate 2.5

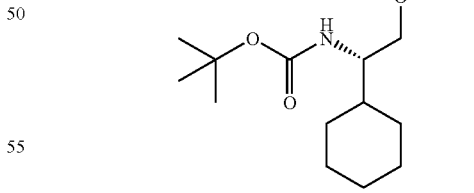

To a solution of commercially available N-Boc-L-cyclohexylglycinol (499 mg, 2.05 mmol) in DMF (8 mL) under N$_2$ at RT are added NaH (164 mg, 4.10 mmol) and EtI (179 μL, 2.26 mmol) at 0° C. The reaction mixture is stirred at RT for 2 h. Then, H$_2$O is added to the resulting solution. The aqueous phase is extracted with CH$_2$Cl$_2$. The combined organic phases are dried over Na$_2$SO$_4$. Concentration under reduced pressure, followed by purification with silica gel column chromatography give Intermediate 2.5: white amorphous material, ES-MS: M+H=272: $_B$t$_{Ret}$=2.46 min.

EXAMPLE 3

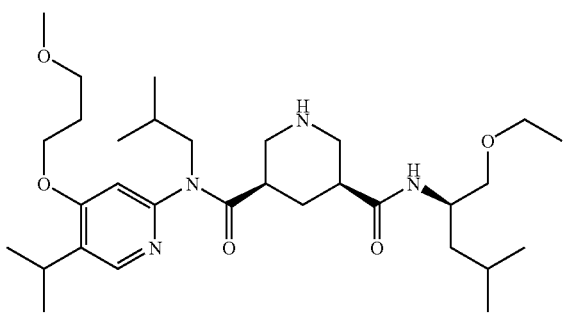 [SMILES: CCOC[C@@H](CC(C)C)NC(=O)[C@@H]1CNC[C@H](C(=O)N(CC(C)C)c2cc(OCCCOC)c(C(C)C)cn2)C1]

A mixture of Intermediate 3.1 (65 mg, 0.098 mmol) and 4M HCl in dioxane (2 mL) is stirred at room temperature. After stirring for 1 h, the reaction mixture is concentrated in vacuo to give Example 3: ES-MS: M+H=563; $_ct_{Ret}$=4.21 min.

Intermediate 3.1

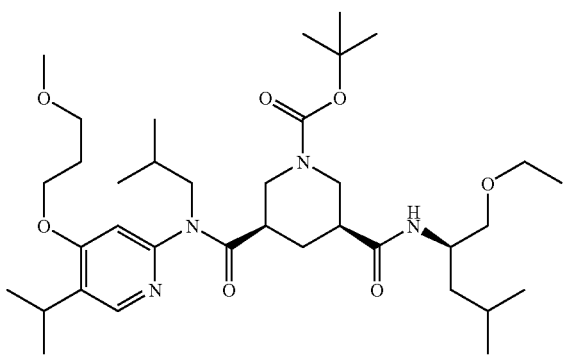 [SMILES: CCOC[C@@H](CC(C)C)NC(=O)[C@H]1C[C@@H](C(=O)N(CC(C)C)c2cc(OCCCOC)c(C(C)C)cn2)CN(C(=O)OC(C)(C)C)C1]

To a solution of Intermediate 3.2 (60 mg, 0.112 mmol) and Intermediate 1.7 (24 mg, 0.132 mmol) in CH$_2$Cl$_2$ (1 mL) are added EDCl.HCl (32 mg, 0.168 mmol), HOAt (23 mg, 0.168 mmol), and Et$_3$N (17 mg, 0.168 mmol) at room temperature; then the mixture is stirred at room temperature. After stirring for 16 h at the same temperature, the reaction mixture is diluted with H$_2$O (10 mL) and extracted with EtOAc (50 mL). The organic phase is successively washed with 5% NaHCO$_3$aq, H$_2$O and brine, and then dried over Na$_2$SO$_4$. The organic phase is concentrated in vacuo to give the crude residue, which is purified by SiO$_2$ column chromatography to give Intermediate 3.1 as a white amorphous material; ES-MS: M+H=663; HPLC: $_ct_{Ret}$=4.83 min.

Intermediate 3.2

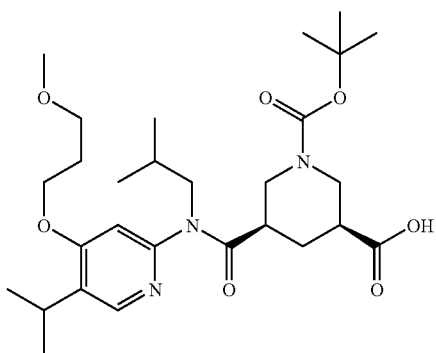 [SMILES: COCCCOc1cc(N(CC(C)C)C(=O)[C@@H]2C[C@H](C(=O)O)CN(C(=O)OC(C)(C)C)C2)ncc1C(C)C]

To a solution of Intermediate 3.3 (85 mg, 0.155 mmol) in THF/H$_2$O (5/5 mL) is added LiOH.H$_2$O (14 mg, 0.330 mmol) at 0° C. After stirring for 1 h at the same temperature, the reaction mixture is quenched with 5% aqueous KHSO$_4$ (20 mL) and extracted with Et$_2$O (100 mL). The organic phase is washed with H$_2$O and brine, and then dried over Na$_2$SO$_4$. The organic phase is concentrated in vacuo to give Intermediate 3.2 as a white amorphous material; ES-MS: M+H=536; HPLC: $_ct_{Ret}$=4.32 min.

Intermediate 3.3

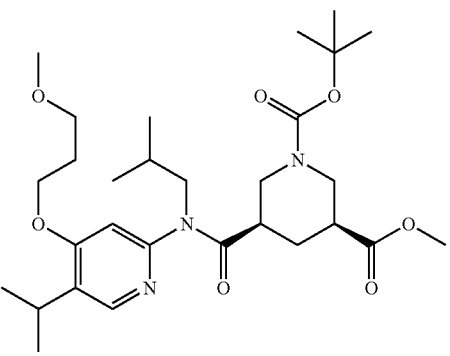 [SMILES: COCCCOc1cc(N(CC(C)C)C(=O)[C@@H]2C[C@H](C(=O)OC)CN(C(=O)OC(C)(C)C)C2)ncc1C(C)C]

To a solution of (3R, 5S)-starting material-F (103 mg, 0.36 mmol) in CH$_3$CN (1 mL) are added Et$_3$N (43 mg, 0.43 mmol), TcBocCl (86 mg, 0.36 mmol) at 0° C. After stirring for 1 h at the same temperature, MgBr$_2$.Et$_2$O (112 mg, 0.43 mmol) and Intermediate 3.4 (100 mg, 0.36 mmol) are added at 0° C., then the mixture is stirred at room temperature. After stirring for 24 h, the reaction mixture is quenched with 5% aqueous KHSO$_4$ and extracted with EtOAc. The organic phase is washed with H$_2$O and brine, and then dried over Na$_2$SO$_4$. The organic phase is concentrated in vacuo to give the crude residue, which is purified by SiO$_2$ column chromatography to give Intermediate 3.3 as a white amorphous material; ES-MS: M+H=550; HPLC: $_ct_{Ret}$=4.65 min.

Intermediate 3.4

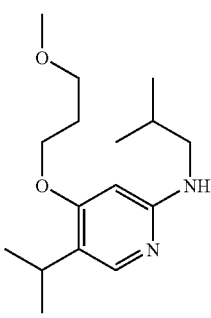 [SMILES: COCCCOc1cc(NCC(C)C)ncc1C(C)C]

To a solution of Intermediate 3.5 (550 mg, 1.85 mmol) in CH$_2$Cl$_2$ (20 mL) are added Et$_3$SiH (2.3 g, 10.8 mmol) and TFA (7.4 g, 64.5 mmol) at 0° C. The resulting mixture is stirred at room temperature. After stirring for 15 h, the reaction mixture is concentrated in vacuo. The residue is suspended in 5% aqueous NaHCO$_3$ and extracted with CH$_2$Cl$_2$. The organic phase is washed with H$_2$O and brine, and then dried over Na$_2$SO$_4$. The organic phase is concentrated in vacuo to give a crude residue, which is purified by SiO$_2$ column chromatography to give Intermediate 3.4 as a white amorphous material; ES-MS: M+H=281; HPLC: $_ct_{Ret}$=3.61 min.

Intermediate 3.5

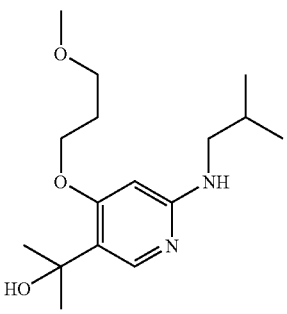 [SMILES: COCCCOc1cc(NCC(C)C)ncc1C(C)(C)O]

To a solution of Intermediate 3.6 (574 mg, 1.7 mmol) in THF (18 mL) is added MeMgBr (0.96 M solution in ether, 8.83 mL, 8.48 mmol) at 0° C. The resulting mixture is stirred at room temperature for 1 h. After adding water, the mixture is extracted with EtOAc, washed with NaHCO$_3$aq., brine and dried over MgSO$_4$. The organic phase is concentrated in vacuo to give the crude residue, which is purified by SiO$_2$ column chromatography to give Intermediate 3.5 as a colorless oil; ES-MS: M+H=297; HPLC: $_ct_{Ret}$=3.50 min.

Intermediate 3.6

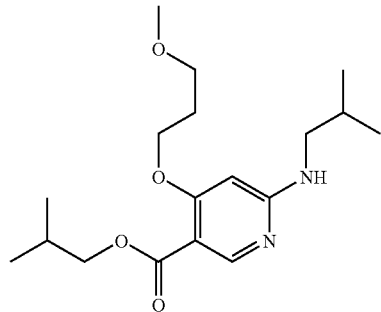 [SMILES: COCCCOc1cc(NCC(C)C)ncc1C(=O)OCC(C)C]

To a solution of Intermediate 3.7 (737 mg, 2.44 mmol) in NMP (17 mL) are added K$_2$CO$_3$ (1.69 g, 12.2 mmol) and isobutylamine (535 mg, 7.32 mmol), and the resulting mixture is stirred at 120° C. overnight. After adding water, the mixture is extracted with EtOAc, washed with water, brine and dried over MgSO$_4$. The organic phase is concentrated in vacuo to give the crude residue, which is purified by SiO$_2$ column chromatography to give Intermediate 3.6 as a colorless crystal; ES-MS: M+H=339; HPLC: $_ct_{Ret}$=3.94 min.

Intermediate 3.7

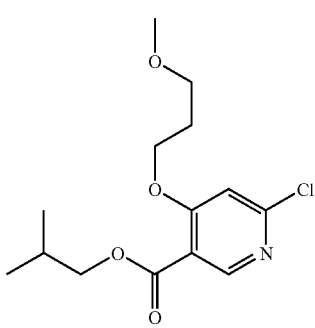 [SMILES: COCCCOc1cc(Cl)ncc1C(=O)OCC(C)C]

To a solution of Intermediate 3.8 (1 g, 4.07 mmol) in DMF (15 mL) are added K$_2$CO$_3$ (1.69 g, 12.2 mmol) and isobutyl-iodide (1.5 g, 8.14 mmol), and the resulting mixture is stirred at 60° C. for 2 hr. The mixture is then diluted with EtOAc, washed with water, sat. KHSO$_4$ aq., sat. NaHCO$_3$ aq., brine and dried over MgSO$_4$. The organic phase is concentrated in vacuo to give the crude residue, which is purified by SiO$_2$ column chromatography to give Intermediate 3.7 as a colorless crystal; ES-MS: M+H=302; HPLC: $_ct_{Ret}$=4.49 min.

Intermediate 3.8

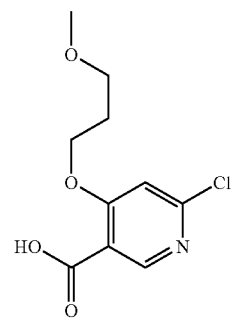 [SMILES: COCCCOc1cc(Cl)ncc1C(=O)O]

To a solution of 3-methoxypropan-1-ol (1.4 g) in THF (30 mL) is added NaH (625 mg, 15.6 mmol) at 0° C. and the mixture is stirred for 30 min at r.t. Then, to the mixture is added a solution of 4,6-dichloronicotinic acid (1.2 g, 6.25 mmol, U.S. Pat. 200549419.) in THF (10 mL) at 0° C. and it is next stirred for 3 h at r.t. After adding water, the mixture is washed with ether. The aqueous phase is acidified with KHSO$_4$ and then extracted with ether. The organic phase is washed with brine and dried over MgSO$_4$. The organic phase is concentrated in vacuo to give crude residue, which is purified by SiO$_2$ column chromatography to give Intermediate 3.7 as a colorless crystal; ES-MS: M+H=; 246, HPLC: $_ct_{Ret}$=3.34 min.

EXAMPLE 4

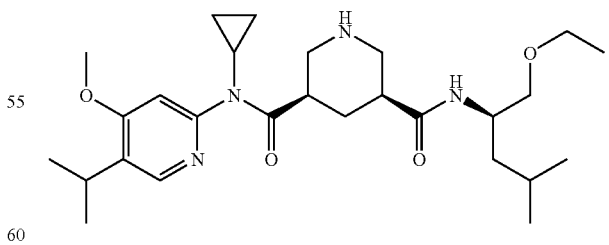

Example 4 is synthesized by deprotection of Intermediate 4.1 (18 mg, 0.03 mmol) analogously to the preparation of Example 1. Example 4: ES-MS: M+H=489: $_ct_{Ret}$=2.84 min.

Intermediate 4.1

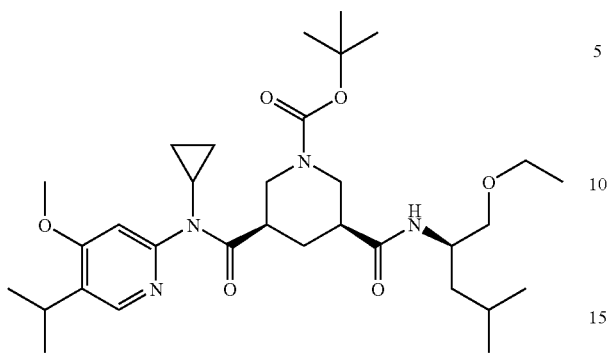

A solution of Intermediate 4.2 (468 mg, 2.27 mmol), Intermediate 1.2 (1 g, 2.5 mmol), BopCl (1.73 g, 6.81 mmol) and triethylamine (688 mg, 6.81 mmol) is stirred at r.t. for 4 h. After adding sat. KHSO$_4$aq., the mixture is extracted with EtOAc. The organic layer is washed with water, sat. NaHCO$_3$ aq, brine and dried over MgSO$_4$. Silica gel column chromatography gives Intermediate 4.1: colorless oil, ES-MS: M+H=589: $_B t_{Ret}$=1.92 min.

Intermediate 4.2

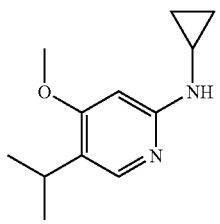

Intermediate 4.3 (2 g, 9 mmol) is dissolved in CH$_2$Cl$_2$ (14 ml). To the solution is added triethylsilane (14 mL) and TFA (14 mL) at r.t. and the mixture is stirred at 50° C. for 3 h. The solvent is removed under vacuum, and the residue is diluted with AcOEt. The resulting mixture is washed with sat. NaHCO$_3$ aq., brine and dried over MgSO$_4$. Silica gel column chromatography gives Intermediate 4.2: colorless crystal, ES-MS: M+H=207: $_B t_{Ret}$=1.51 min.

Intermediate 4.3

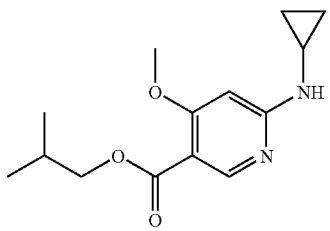 [SMILES: COc1cc(NC2CC2)ncc1C(=O)OCC(C)C]

To a solution of Intermediate 4.4 (2.5 g, 2.63 mmol) in NMP (20 mL) is added K$_2$CO$_3$ (9.2 g, 66.6 mmol) and isobutyl iodide (2.3 mL, 20 mmol). The resulting mixture is stirred at 80° C. for 40 min. Then cyclopropylamine (4.6 mL, 66.6 mmol) is added and the reaction mixture is stirred overnight at 110° C. After adding water, the mixture is extracted with AcOEt. The organic layer is washed with water, brine and dried over MgSO$_4$. Recrystallization from EtOAc-n-hexane gives Intermediate 4.3: colorless crystal, ES-MS: M+H= 265: $_B t_{Ret}$=1.54 min.

Intermediate 4.4

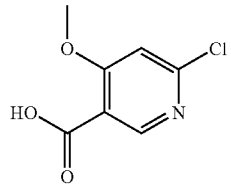

To a suspension of NaH (5.2 g, 130 mmol) in THF (100 mL) is added MeOH (4.2 g, 130 mmol) at 0° C. After stirring at r.t. for 30 min, a solution of 4,6-dichloronicotinic acid (10 g, 52.9 mmol, U.S. Pat. 2005049419.) in THF (100 mL) is added dropwise at 0° C. The resulting mixture is stirred at room temperature overnight. After adding water, the mixture is washed with ether. The aqueous phase is acidified with KHSO$_4$ and then extracted with ether. The organic phase is washed with brine and dried over MgSO$_4$. Concentration under reduced pressure gives Intermediate 4.4: colorless crystal, ES-MS: M+H=188: $_C t_{Ret}$=1.80 min.

EXAMPLE 5

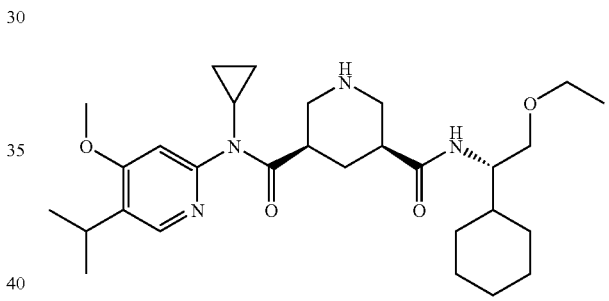

Example 5 is synthesized by deprotection of Intermediate 5.1 analogously to the preparation of Example 1. Example 5: ES-MS: M+H=515: $_C t_{Ret}$=3.92 min.

Intermediate 5.1

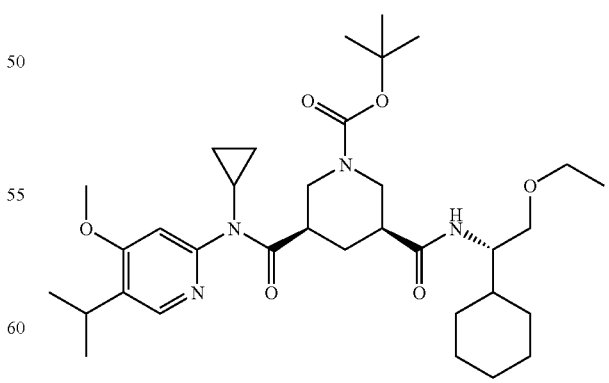

Intermediate 5.1 is synthesized by coupling reaction of Intermediate 5.2 with Intermediate 2.4 analogously to the preparation of Intermediate 1.1: ES-MS: M+H= 615: $_C t_{Ret}$=4.45 min.

Intermediate 5.2

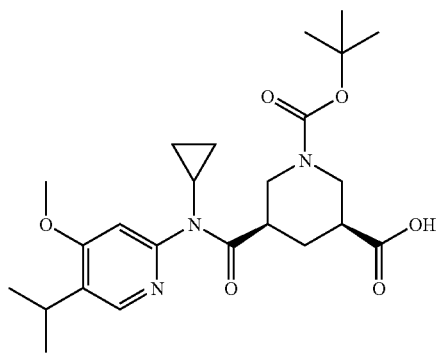 [SMILES: COc1cc(N(C(=O)[C@@H]2C[C@H](C(=O)O)CN(C(=O)OC(C)(C)C)C2)C2CC2)ncc1C(C)C]

Intermediate 5.2 is synthesized by saponification of Intermediate 5.3 (1 g, 2.1 mmol) analogously to the preparation of Intermediate 1.2. Intermediate 5.2; colorless oil, ES-MS: M=462; HPLC: $_ct_{Ret}$=2.85 min.

Intermediate 5.3

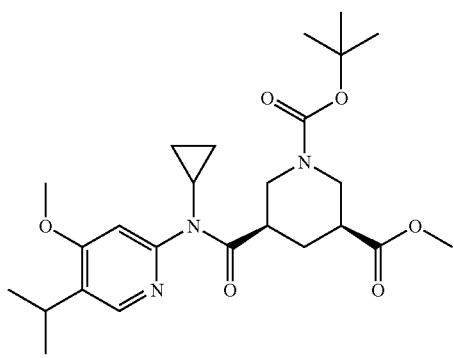 [SMILES: COC(=O)[C@H]1C[C@@H](C(=O)N(c2cc(OC)c(C(C)C)cn2)C2CC2)CN(C(=O)OC(C)(C)C)C1]

Intermediate 5.3 is synthesized by condensation of Intermediate 4.2 (800 mg, 3.88 mmol) and (3R,5S)-Starting material-F (1230 mg, 4.27 mmol) analogously to the preparation of Intermediate 1.3. Intermediate 5.3; colorless oil, ES-MS: M=476; HPLC: $_ct_{Ret}$=1.78 min.

EXAMPLE 6

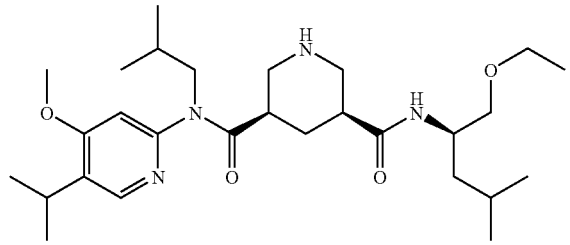 [SMILES: CCOC[C@@H](CC(C)C)NC(=O)[C@@H]1CNC[C@H](C(=O)N(CC(C)C)c2cc(OC)c(C(C)C)cn2)C1]

Example 6 is synthesized by deprotection of Intermediate 6.1 analogously to the preparation of Example 1. Example 6: ES-MS: M+H=505: $_ct_{Ret}$=3.29 min.

Intermediate 6.1

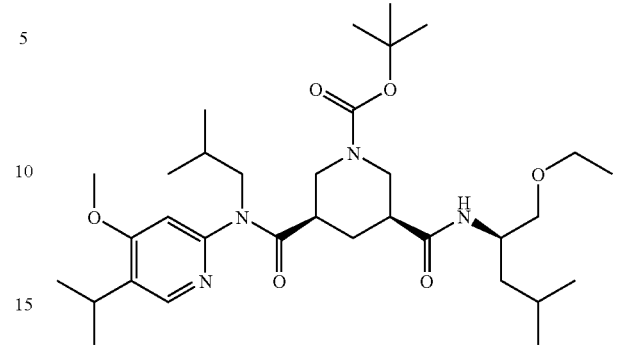

Intermediate 6.1 is synthesized by coupling reaction of Intermediate 6.2 with Intermediate 1.7. analogously to the preparation of Intermediate 1.1. Intermediate 6.1: ES-MS: M+H=605: $_ct_{Ret}$=4.11 min.

Intermediate 6.2

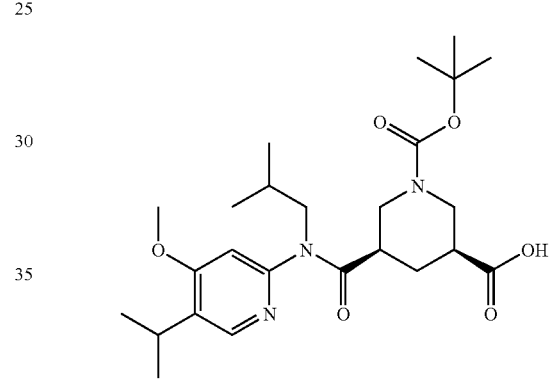

Intermediate 6.2 is synthesized by saponification of Intermediate 6.3 analogously to the preparation of Intermediate 1.2. Intermediate 6.2: ES-MS: M+H=478: $_ct_{Ret}$=3.41 min.

Intermediate 6.3

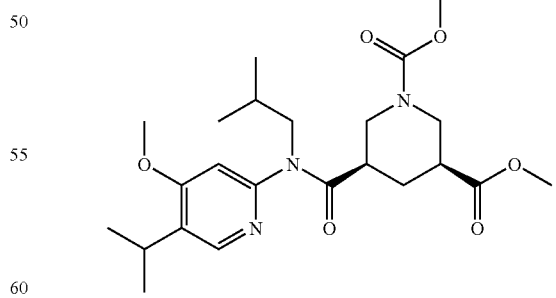

Intermediate 6.3 is synthesized by coupling reaction of Intermediate 6.4 with (3R, 5S)-starting material-F analogously to the preparation of Intermediate 1.3. Intermediate 6.3: S-MS: M+H=492: $_ct_{Ret}$=3.81 min.

Intermediate 6.4

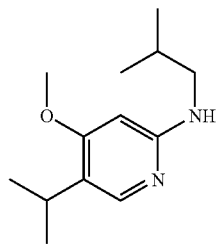 [SMILES: COc1cc(NCC(C)C)ncc1C(C)C]

Intermediate 6.4 is synthesized by dehydroxylation of Intermediate 6.5 analogously to the preparation of Intermediate 1.4. Intermediate 6.4: ES-MS: M+H=223: $_c t_{Ret}$=2.78 min.

Intermediate 6.5

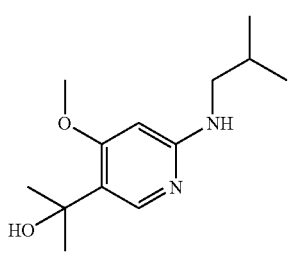 [SMILES: COc1cc(NCC(C)C)ncc1C(C)(C)O]

Intermediate 6.5 is synthesized by alkylation of Intermediate 6.6 analogously to the preparation of Intermediate 1.5. Intermediate 6.5: ES-MS: M+H=239: $_c t_{Ret}$=1.95 min.

Intermediate 6.6

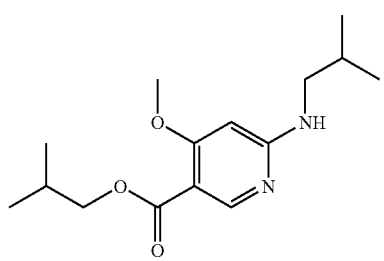 [SMILES: COc1cc(NCC(C)C)ncc1C(=O)OCC(C)C]

Intermediate 6.6 is synthesized from Intermediate 4.6 (using isobutylamine instead of cyclopropylamine) analogously to the preparation of Intermediate 4.5. Intermediate 6.6: ES-MS: M+H=281: $_c t_{Ret}$=2.54 min.

EXAMPLE 7

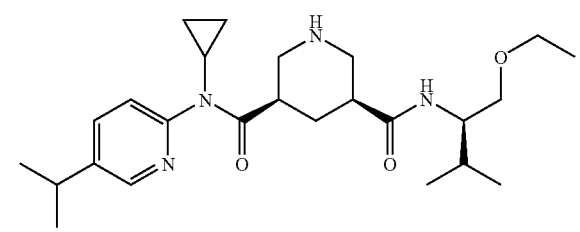 [SMILES: CCOC[C@H](NC(=O)[C@@H]1CNC[C@H](C(=O)N(c2ccc(C(C)C)cn2)C2CC2)C1)C(C)C]

Example 7 is synthesized by deprotection of Intermediate 7.1 analogously to the preparation of Example 1. Intermediate 7.1: ES-MS: M+H=445: $_c t_{Ret}$=3.44 min.

Intermediate 7.1

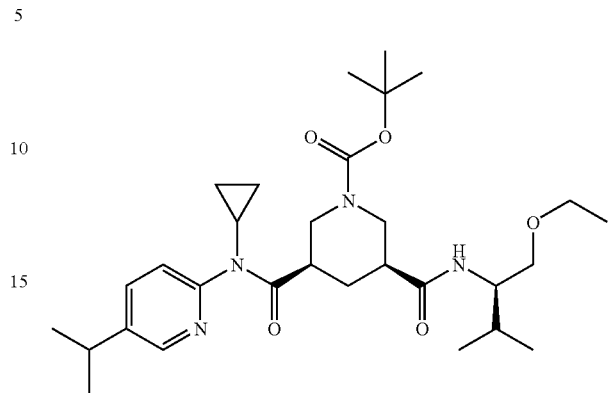

Intermediate 7.1 is synthesized by coupling reaction of Intermediate 2.2 with Intermediate 7.2 analogously to the preparation of Intermediate 1.1. Intermediate 7.1: ES-MS: M+H=545: $_c t_{Ret}$=4.30 min.

Intermediate 7.2

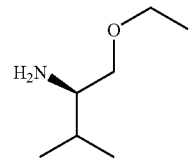

Intermediate 7.2 is synthesized by deprotection of Intermediate 7.3 analogously to the preparation of Example 1. Intermediate 7.2: ES-MS: M+H=132: $_B t_{Ret}$=1.17 min.

Intermediate 7.3

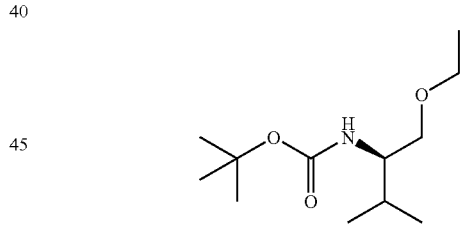

Intermediate 7.3 is synthesized by alkylation of Boc-D-valinol [Journal of Organic Chemistry, 2000, 65 (16), 5037-5042] analogously to the preparation of Example 1.8. Intermediate 7.3: ES-MS: M+H-Boc=132: $_B t_{Ret}$=2.03 min

EXAMPLE 8

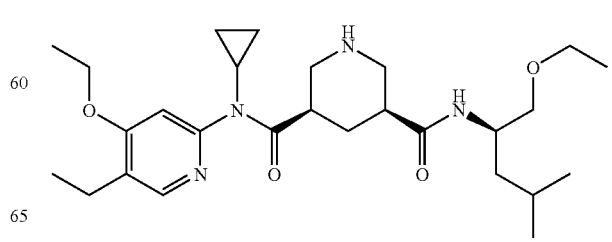

Example 8 is synthesized by deprotection of Intermediate 8.1 analogously to the preparation of Example 1. Example 8: ES-MS: M+H=589: $_ct_{Ret}$=3.50 min.

Intermediate 8.1

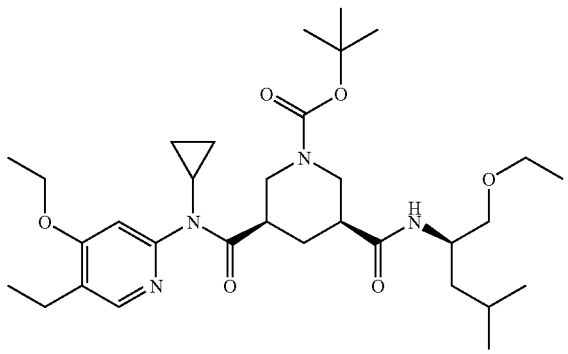 [SMILES: CCOC[C@@H](CC(C)C)NC(=O)[C@H]1C[C@@H](C(=O)N(c2cc(OCC)c(CC)cn2)C2CC2)CN(C(=O)OC(C)(C)C)C1]

To a solution of Intermediate 8.2 (49 mg, 0.239 mmol) and Intermediate 1.2 (80 mg, 0.20 mmol) in $CH_2Cl_2$ are added BopCl (153 mg, 0.60 mmol) and $Et_3N$ (61 mg, 0.60 mmol). After stirring for 25 h at room temperature, the reaction mixture is diluted with $H_2O$ (10 mL) and extracted with EtOAc (50 mL). The organic phase is successively washed with 5% $NaHCO_3$aq, $H_2O$, and brine, then dried over $Na_2SO_4$. The organic phase is concentrated in vacuo to give the crude residue, which is purified by $SiO_2$ column chromatography to give Intermediate 8.1 as a white amorphous material; ES-MS: M+H=589; HPLC: $_ct_{Ret}$=3.50 min.

Intermediate 8.2

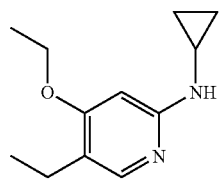

Intermediate 8.2 is synthesized by reduction of Intermediate 8.3 analogously to the preparation of Intermediate 1.4. Intermediate 8.2: ES-MS: M+H=207: $_ct_{Ret}$=3.71 min.

Intermediate 8.3

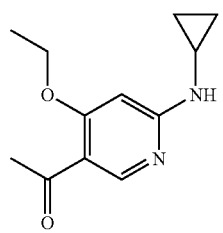 [SMILES: CCOc1cc(NC2CC2)ncc1C(C)=O]

To a solution of Intermediate 8.4 (500 mg, 2.5 mmol) in DMSO (10 mL) are added cyclopropylamine (1.65 g, 28.9 mmol) and $K_2CO_3$ (415 mg, 7.5 mmol) at room temperature. The resulting mixture is then stirred at 80° C. After stirring for 5 h, the reaction mixture is cooled down to room temperature and quenched with $H_2O$ (50 mL). The resulting mixture is extracted with EtOAc (100 mL). The organic phase is washed with $H_2O$ and brine, and then dried over $Na_2SO_4$. The organic phase is concentrated in vacuo to give the crude residue, which is purified by $SiO_2$ column chromatography to give Intermediate 8.3 as a yellow amorphous material; ES-MS: M+H=221; HPLC: $_ct_{Ret}$=2.34 min.

Intermediate 8.4

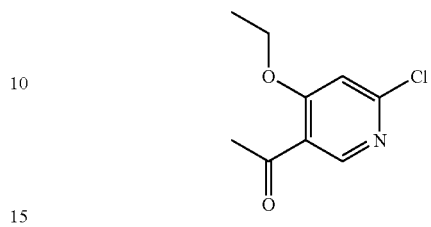

To a solution of Intermediate 8.5 (1.85 g, 7.56 mmol) in THF (40 mL) is added MeLi (1M in $Et_2O$, 9.07 mmol) at 0° C., then the mixture is stirred at room temperature. After stirring for 1 h at room temperature, the reaction mixture is cooled down to 0° C. and quenched with 5% aqueous $KHSO_4$ (100 mL). The reaction mixture is then extracted with $CH_2Cl_2$ (100 mL). The organic phase is washed with 5% aqueous $NaHCO_3$, $H_2O$ and brine, and then dried over $Na_2SO_4$. The organic phase is concentrated in vacuo to give Intermediate 8.4 as a yellow amorphous material; ES-MS: M+H=200; HPLC: $_ct_{Ret}$=2.82 min.

Intermediate 8.5

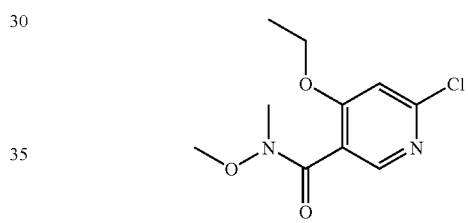

To a solution of Intermediate 8.6 (2 g, 10 mmol) in $ClCH_2CH_2Cl$ are added $SOCl_2$ (2 mL) and DMF (0.1 mL) at room temperature, then the mixture is stirred at 60° C. After stirring for 3 h at 60° C., the reaction mixture is concentrated in vacuo to give a gummy material which is used in the next reaction without further purification.

To a solution of the crude in $CH_2Cl_2$ is added N,O-dimethyl hydroxylamine hydrochloride (1.46 g, 15 mmol) and $Et_3N$ (1.52 g, 15 mmol) at 0° C., then the mixture is stirred at room temperature. After stirring for 19 h at room temperature, the reaction mixture is quenched with $H_2O$ (100 mL) and extracted with $CH_2Cl_2$ (100 mL). The organic phase is successively washed with 5% $NaHCO_3$ aq, $H_2O$, and brine, and then dried over $Na_2SO_4$. The organic phase is concentrated in vacuo to give the crude residue, which is purified by $SiO_2$ column chromatography to give Intermediate 8.5 as a brown oil; ES-MS: M+H=245; HPLC: $_ct_{Ret}$=2.27 min.

Intermediate 8.6

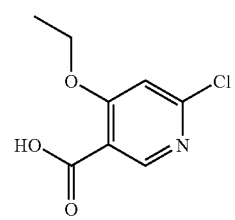

Intermediate 8.6 is synthesized by reaction of 2,4-dichloronicotinic (U.S. Pat. 2005049419.) acid with sodium ethoxide, analogously to the preparation of Intermediate 4.6. Intermediate 8.6: ES-MS: M+H=202: $_c t_{Ret}$=2.12 min.

EXAMPLE 9

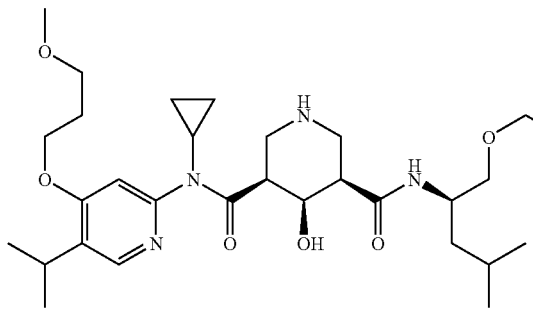

A solution of Intermediate 9.1 (13 mg, 0.02 mmol) in 4 N HCl-dioxane (4 mL) under $N_2$ is stirred at 0° C. for 15 min. Then, the solution is warmed up to room temperature and stirred at RT for 1 h. The mixture is concentrated under reduced pressure to give Example 9 as a white amorphous material. ES-MS: M+H=563: $_A t_{Ret}$=2.48 min.

Intermediate 9.1

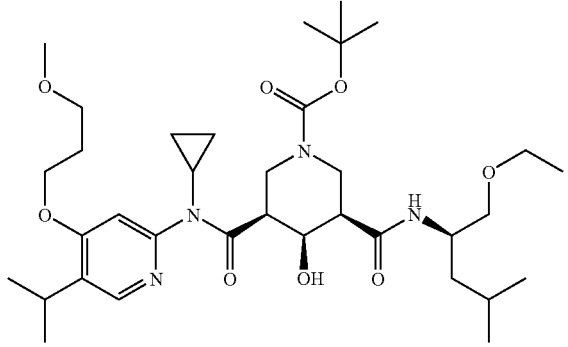 [SMILES: CCOC[C@@H](CC(C)C)NC(=O)[C@@H]1CN(C(=O)OC(C)(C)C)C[C@H](C(=O)N(c2cc(OCCCOC)c(C(C)C)cn2)C2CC2)[C@@H]1O]

To a solution of Intermediate 9.2 (20 mg, 0.037 mmol) in $CH_2Cl_2$ (3 mL) under $N_2$ at 0° C. are added EDCl.HCl (11.6 mg, 0.075 mmol) and HOAt (10.1 mg, 0.075 mmol). After stirring at the same temperature for 5 min, Intermediate 1.7 (13.6 mg, 0.075 mmol) and $Et_3N$ (0.04 mL, 0.22 mmol) are added to the reaction mixture. The resulting solution is warmed up to RT and stirred at room temperature overnight. The reaction is quenched with $H_2O$ and extracted with $CH_2Cl_2$. The combined organic extracts are washed with $H_2O$ and brine, dried over $Na_2SO_4$, filtered, and concentrated in vacuo. The residue is purified by flash chromatography on silica gel to give the desired coupling product, Intermediate 9.1 as a white amorphous material. ES-MS: M+H=663; HPLC: $_c t_{Ret}$=3.71 min.

Intermediate 9.2

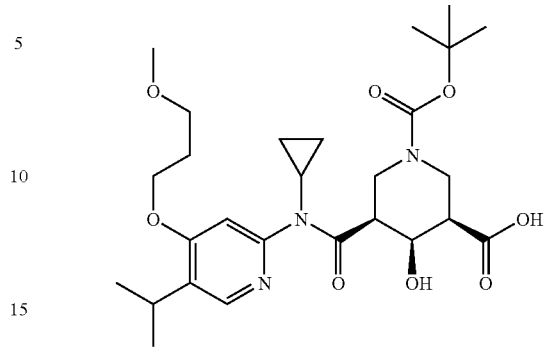

To a solution of Intermediate 9.3 (20 mg, 0.04 mmol) in dry THF (1 mL) is added 0.22 M solution of LiOH (0.5 mL, 0.11 mmol) at 0° C. The resulting solution is stirred at RT for 2 h. The reaction is quenched with saturated $KHSO_4$ solution (1 mL) and extracted with EtOAc. Upon drying over with $Na_2SO_4$, concentration under reduced pressure gives Intermediate 9.2 as a solid. This material is used in the next step without further purification. ES-MS: M+H=536: $_c t_{Ret}$=2.93 min.

Intermediate 9.3

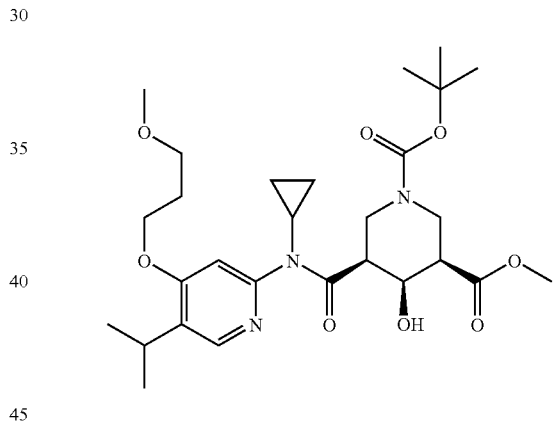

To a solution of (3R,4S,5S)-starting material-G (100 mg, 0.33 mmol) in dry THF (5 mL) under $N_2$ is added (1-Chloro-2-methyl-propenyl)-dimethyl-amine (0.066 ml, 0.69 mmol) with cooling in an ice-bath. After stirring at the same temperature for 5 min., the reaction is warmed up to RT and it is additionally stirred for 20 min. The reaction mixture is concentrated under reduced pressure to give (3R,4R,5S)-5-Chlorocarbonyl-4-hydroxy-piperidine-1,3-d icarboxylic acid 1-tert-butyl ester 3-methyl ester. This material is used in the next step without further purification. To a solution of Intermediate 9.4 (87 mg, 0.33 mmol) and $Et_3N$ (0.13 mL, 0.99 mmol) in dry THF (2 mL) is added dropwise a solution of the acyl chloride in THF (2 mL) at 0° C., and the resulting mixture is stirred for 2 h at RT. The mixture is quenched with sat. aq. $NaHCO_3$ and washed with water, dried over $Na_2SO_4$ and concentrated under reduced pressure. The residue is purified by reversed phase chromatography to afford Intermediate 9.3 as an oil. ES-MS: M+H=550: $_c t_{Ret}$=3.74 min.

Intermediate 9.4

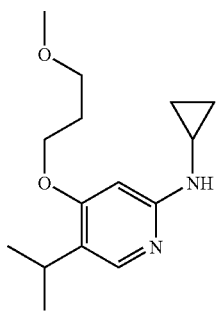 [SMILES: COCCCOc1cc(NC2CC2)ncc1C(C)C]

Intermediate 9.5 (4.3 g, 15.3 mmol) is dissolved in CH$_2$Cl$_2$ (51 mL). To the solution is added triethylsilane (24.4 mL, 153 mmol) and TFA (22.7 mL, 306 mmol) at RT. and the mixture is stirred at 35° C. for 10 h. The solvent is removed under vacuum, and the residue is diluted with AcOEt. The organic phase is washed with sat. NaHCO$_3$ aq., brine and dried over Na$_2$SO$_4$. Silica gel column chromatography gives Intermediate 9.4: Colorless crystal, ES-MS: M+H=265: $_ct_{Ret}$=2.53 min.

Intermediate 9.5

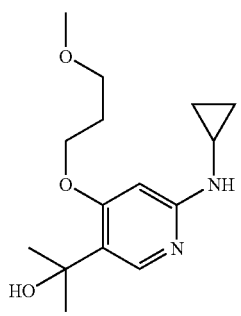 [SMILES: COCCCOc1cc(NC2CC2)ncc1C(C)(C)O]

Intermediate 9.6 (5.3 g, 16.4 mmol) is dissolved in THF (84 mL). To the solution is added 0.97 M MeMgBr in THF (85 mL, 82.2 mmol) at 0° C. and the mixture is stirred for 1 h at the same temperature. After adding water, the mixture is extracted with AcOEt. The organic layer is washed with brine and dried over Na$_2$SO$_4$. Silica gel column chromatography gives Intermediate 9.5: Colorless crystal, ES-MS: M+H= 281: $_ct_{Ret}$=1.75 min.

Intermediate 9.6

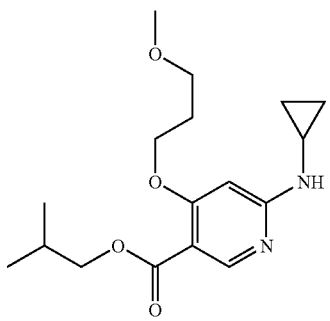 [SMILES: COCCCOc1cc(NC2CC2)ncc1C(=O)OCC(C)C]

Intermediate 9.7 (22.1 g, 90.2 mmol) is dissolved in NMP (250 mL). To the solution is added K$_2$CO$_3$ (37.2 g, 270.6 mmol) and isobutyl iodide (15.5 mL, 135.3 mmol) and the mixture is stirred at 80° C. for 1 h, then cyclopropylamine (33.9 mL, 451.0 mmol) is added and the mixture is stirred for overnight at 110° C. After adding water, the mixture is extracted with AcOEt. The organic layer is washed with water, brine and dried over Na$_2$SO$_4$. Silica gel column chromatography gives Intermediate 9.6: Colorless crystal, ES-MS: M+H=323: $_ct_{Ret}$=2.61 min.

Intermediate 9.7

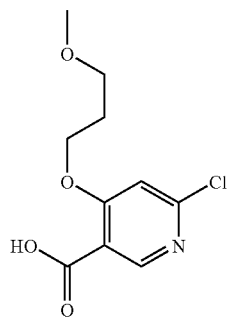 [SMILES: COCCCOc1cc(Cl)ncc1C(=O)O]

4,6-Dichloronicotinic acid (20 g, 104.7 mmol, U.S. Pat. 2005049419.) is dissolved in THF (120 mL). The solution is added to a solution of NaH (11.4, 262 mmol) and 3-methoxy-propan-1-ol (23.6 g, 262 mmol) in THF (120 mL) at 0° C. and the resulting mixture is stirred for 2 h at RT. After adding water, the mixture is washed with ether. The aqueous layer is acidified with 1 N aq. HCl and extracted with EtOAc. The organic layer is washed with brine and dried over Na$_2$SO$_4$. Removal of the solvent under vacuum gives Intermediate 9.7: Colorless crystal, ES-MS: M+H=246: $_ct_{Ret}$=2.14 min.

EXAMPLE 10

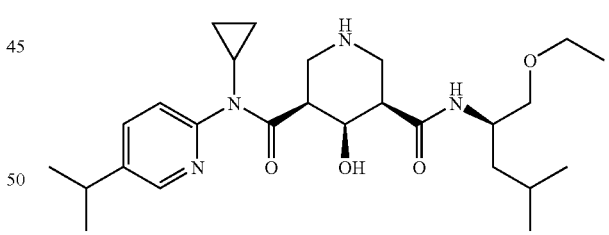

A solution of Intermediate 10.1 (262 mg, 0.46 mmol) in 4N HCl in dioxane (3 mL) under N$_2$ is stirred at RT for 40 min. Concentration under the reduced pressure gives the HCl salt. Then, sat. NaHCO$_3$ aq. is added. The aqueous phase is extracted with EtOAc. The combined organic extracts are dried over Na$_2$SO$_4$. Concentration under reduced pressure gives the crude residue, which is purified by silica gel chromatography followed by preparative reversed phase HPLC to give the desired amine (170.2 mg, 0.358 mmol). To a solution of amine in toluene (3 mL) is added 4N HCl-dioxane (3 mL). Concentration under reduced pressure gives the desired Example 10 (HCl salt) as a white material: ES-MS: M+H=475: $_ct_{Ret}$=2.87 min.

Intermediate 10.1

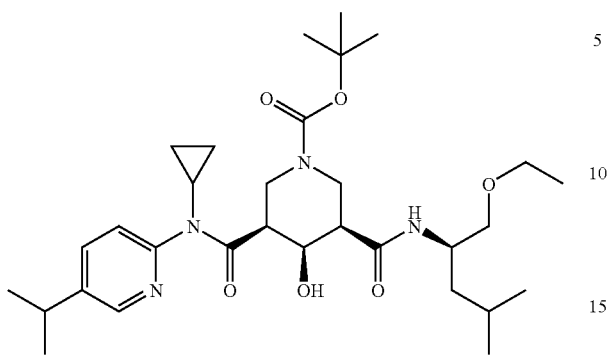

To a solution of Intermediate 10.2 (174.5 mg, 0.39 mmol) in CH$_2$Cl$_2$ (10 mL), under N$_2$ at RT, are added EDCl.HCl (130 mg, 0.57 mmol) and HOAt (100 mg, 0.73 mmol). The reaction mixture is stirred at the same temperature for a few minutes. Then, Intermediate 1.7 (117 mg, 0.64 mmol) and triethylamine (0.19 mL, 1.36 mmol) are added at 0° C. The resulting solution is stirred at RT overnight, and then H$_2$O is added to the reaction mixture. The aqueous phase is extracted with CH$_2$Cl$_2$. The combined organic phases are dried over Na$_2$SO$_4$. Concentration under reduced pressure gives the crude residue, which is purified by silica gel chromatography to afford Intermediate 10.1 as a white amorphous material; ES-MS: M=575; HPLC: $_c t_{Ret}$=3.90 min.

Intermediate 10.2

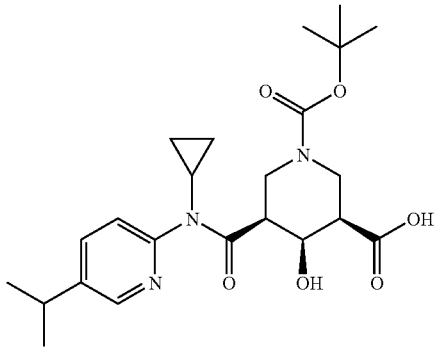 [SMILES: CC(C)c1ccc(N(C(=O)[C@H]2CN(C(=O)OC(C)(C)C)C[C@@H](C(=O)O)[C@H]2O)C2CC2)nc1]

To a solution of Intermediate 10.3 (180 mg, 0.39 mmol) in THF (7 mL) at 0° C. is slowly added aqueous LiOH (40.7 mg, 0.97 mmol in H$_2$O (7 mL). The resulting solution is stirred at the same temperature for 25 min. The reaction mixture is diluted with H$_2$O and then washed with Et$_2$O. The aqueous phase is acidified with sat. KHSO$_4$ aq. and then extracted with Et$_2$O. The combined organic extracts are dried over Na$_2$SO$_4$. Concentration under reduced pressure gives Intermediate 10.2 as a white amorphous material; ES-MS: M=448; HPLC: $_c t_{Ret}$=3.00 min.

Intermediate 10.3

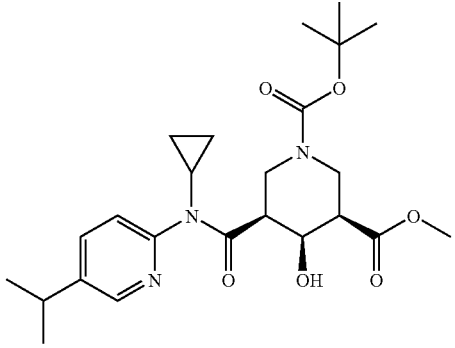

To a solution of (3R,4S,5S)-starting material-G (200 mg, 0.65 mmol) in CH$_2$Cl$_2$ (5 mL), under N$_2$ at 0° C., is added 1-chloro-N,N,2-trimethyl-1-propenyl amine (0.1 mL, 0.76 mmol). The solution is stirred at the same temperature for 60 min. Then, Intermediate 1.4 (229 mg, 1.3 mmol) is added at 0° C. The resulting solution is warmed to RT and stirred for 20 min, then H$_2$O is added and the mixture is extracted with CH$_2$Cl$_2$. The combined organic extracts are dried over Na$_2$SO$_4$. Concentration under reduced pressure gives the crude residue, which is purified by silica gel chromatography to give Intermediate 10.3. ES-MS: M=462; HPLC: $_c t_{Ret}$=3.66 min.

EXAMPLE 11

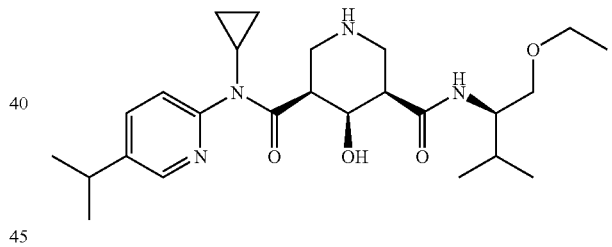

Example 11 is synthesized by deprotection of Intermediate 11.1 analogously to the preparation of Example 1. Example 11: ES-MS: M+H=461: $_c t_{Ret}$=3.80 min.

Intermediate 11.1

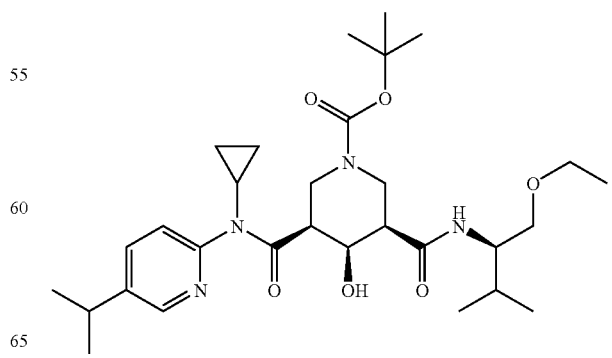

Intermediate 11.1 is synthesized by coupling reaction of Intermediate 10.2 with Intermediate 7.2 analogously to the preparation of Intermediate 1.1. Intermediate 11.1: ES-MS: M+H=561: $_c t_{Ret}$=4.14 min.

EXAMPLE 12

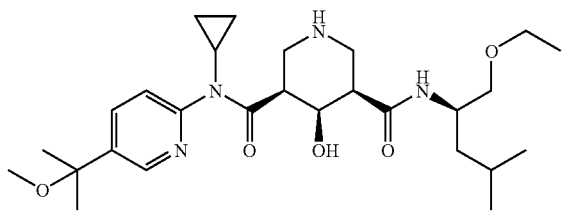 [SMILES: CCOC[C@@H](CC(C)C)NC(=O)[C@@H]1CNC[C@H](C(=O)N(c2ccc(C(C)(C)OC)cn2)C2CC2)[C@@H]1O]

A solution of Intermediate 12.1 (9.3 mg, 0.015 mmol) in 4 N HCl-dioxane (1 mL), under $N_2$, is stirred at 0° C. for 15 min. Then, the solution is warmed up to RT and stirred at room temperature for 20 min. The mixture is concentrated under reduced pressure to give Example 12 as a white amorphous material. ES-MS: M+H=505: $_c t_{Ret}$=2.94 min.
Intermediate 12.1

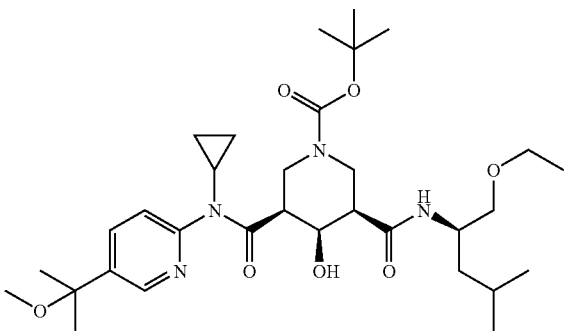 [SMILES: CCOC[C@@H](CC(C)C)NC(=O)[C@@H]1CN(C(=O)OC(C)(C)C)C[C@H](C(=O)N(c2ccc(C(C)(C)OC)cn2)C2CC2)[C@@H]1O]

To a solution of Intermediate 12.2 (63 mg, 0.13 mmol) in $CH_2Cl_2$ (3 mL) under $N_2$ at 0° C. are added EDCl.HCl (33.0 mg, 0.21 mmol) and HOAt (29.0 mg, 0.21 mmol). After stirring at the same temperature for 5 min, Intermediate 1.7 (38.0 mg, 0.21 mmol) and $Et_3N$ (0.06 mL, 0.42 mmol) are added to the reaction mixture. The resulting solution is warmed up to RT and stirred at RT overnight. The reaction is quenched with $H_2O$ and extracted with $CH_2Cl_2$. The combined organic extracts are washed with $H_2O$ and brine, dried over $Na_2SO_4$, filtered, and concentrated in vacuo. The residue is purified by flash chromatography on silica gel to give Intermediate 12.1 as a white amorphous material. ES-MS: M+H=605; HPLC: $_c t_{Ret}$=3.93 min.
Intermediate 12.2

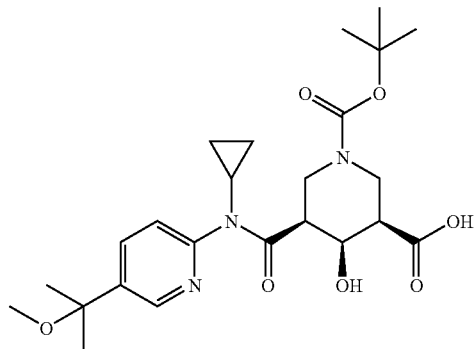 [SMILES: COC(C)(C)c1ccc(N(C(=O)[C@H]2CN(C(=O)OC(C)(C)C)C[C@@H](C(=O)O)[C@H]2O)C2CC2)nc1]

To a solution of Intermediate 12.3 (68 mg, 0.14 mmol) in dry THF (1 mL) is added 0.4 M solution of LiOH (1.0 mL, 0.41 mmol) at 0° C. The resulting solution is stirred at RT for 2 h. The reaction is quenched with sat. $KHSO_4$ aq. (1 mL) and extracted with EtOAc. Upon drying over with $Na_2SO_4$, concentration under reduced pressure gives Intermediate 12.2 as a solid. This material is used in the next step without further purification. ES-MS: M+H=478: $_A t_{Ret}$=2.77 min.
Intermediate 12.3

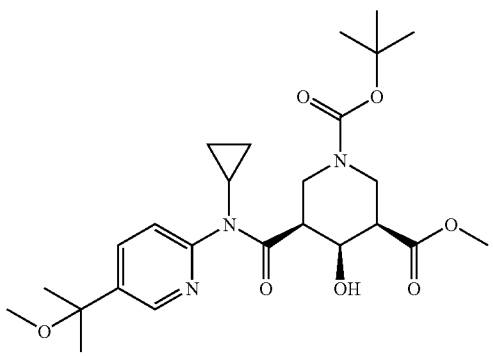

To a solution of (3R,4S,5S)-starting material-G (132 mg, 0.44 mmol) in dry $CH_2Cl_2$ (2 mL), under $N_2$, is added (1-Chloro-2-methyl-propenyl)-dimethyl-amine (0.06 ml, 0.66 mmol) with cooling in an ice-bath. After stirring at the same temperature for 5 min, the reaction is warmed up to RT and additionally stirred for 20 min. The reaction mixture is concentrated under reduced pressure to give (3R,4R,5S)-5-Chlorocarbonyl-4-hydroxy-piperidine-1,3-dicarboxylic acid 1-tert-butyl ester 3-methyl ester. This material is used in the next step without further purification. To a solution of Intermediate 12.4 (90 mg, 0.44 mmol) and $Et_3N$ (0.18 mL, 1.32 mmol) in dry $CH_2Cl_2$ (2 mL) is added dropwise a solution of the acyl chloride in $CH_2Cl_2$ (2 mL) at 0° C. The resulting mixture is stirred for 2 h at room temperature. The mixture is quenched with sat. $NaHCO_3$ (3 mL) aq., washed with water, dried over $Na_2SO_4$, and concentrated under reduced pressure. The residue is purified by flash chromatography on silica gel to afford Intermediate 12.3 as an oil. ES-MS: M+H=492: $_A t_{Ret}$=3.10 min.
Intermediate 12.4

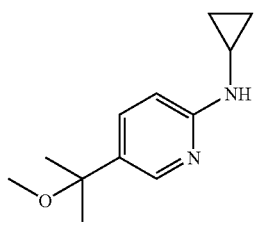

In a 5 mL glass microwave vessel are placed Intermediate 1.5 (100 mg, 0.52 mmol) and CAN (123.4 mg, 0.21 mmol) in dry MeOH (2 mL). The reaction is heated under microwave irradiation using Biotage Initiator 60 EXP at 100° C. for 15 min. The solvent is removed and the residue is washed with sat. aq. $NaHCO_3$, water, dried over $Na_2SO_4$, and concentrated under reduced pressure. The residue is purified by flash chromatography on silica gel to give Intermediate 12.4 as a white solid material. ES-MS: M+H=207: $_c t_{Ret}$=3.02 min.

EXAMPLE 13

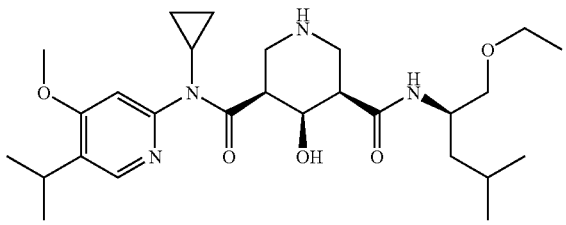 [SMILES: CCOC[C@@H](CC(C)C)NC(=O)[C@@H]1CNC[C@H](C(=O)N(c2cc(OC)c(C(C)C)cn2)C2CC2)[C@@H]1O]

A solution of Intermediate 13.1 (107 mg, 0.177 mmol) in 4N HCl in dioxane (3 mL) under $N_2$ is stirred at RT for 40 min. Concentration under reduced pressure gives the crude HCl salt. The crude is purified by preparative reversed phase HPLC to give Example 13 as a white material: ES-MS: M+H=505: $_Ct_{Ret}$=2.63 min.

Intermediate 13.1

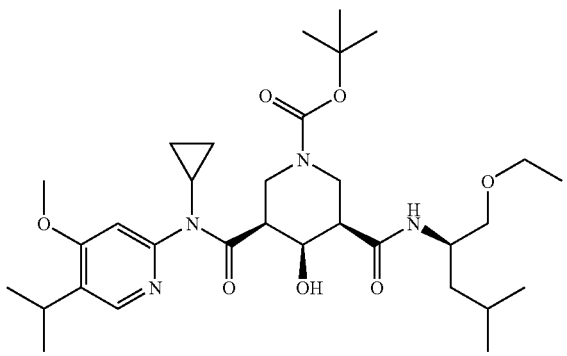 [SMILES: CCOC[C@@H](CC(C)C)NC(=O)[C@@H]1CN(C(=O)OC(C)(C)C)C[C@H](C(=O)N(c2cc(OC)c(C(C)C)cn2)C2CC2)[C@@H]1O]

To a solution of Intermediate 13.2 (122.7 mg, 0.257 mmol) in $CH_2Cl_2$ (5 mL) under $N_2$ at RT are added EDCl.HCl (83 mg, 0.363 mmol) and HOAt (60.9 mg, 0.447 mmol). The reaction mixture is stirred at the same temperature for a few minutes. Then, Intermediate 1.7 (69 mg, 0.38 mmol) and triethylamine (0.11 mL, 0.82 mmol) are added at RT. The resulting solution is stirred at the same temperature overnight. Concentration under reduced pressure gives crude residue, which is purified by silica gel chromatography to afford Intermediate 13.1 as a white amorphous material; ES-MS: M=605; HPLC: $_Ct_{Ret}$=3.39 min.

Intermediate 13.2

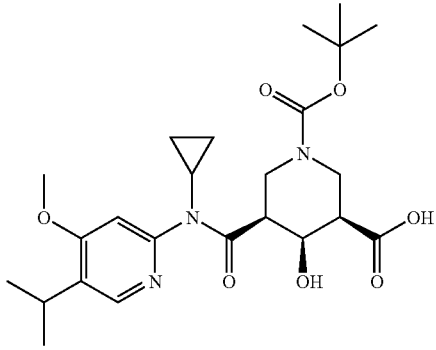 [SMILES: COc1cc(N(C(=O)[C@H]2CN(C(=O)OC(C)(C)C)C[C@@H](C(=O)O)[C@H]2O)C2CC2)ncc1C(C)C]

To a solution of Intermediate 13.3 (168 mg, 0.34 mmol) in THF (10 mL) at 0° C. is slowly added aqueous LiOH (27.65 mg, 0.659 mmol in $H_2O$ (10 mL)). The resulting solution is stirred at the same temperature for 40 min. The reaction mixture is diluted with $H_2O$ and washed with $Et_2O$. The aqueous phase is acidified with sat. $KHSO_4$ aq. and extracted with $Et_2O$. The combined organic extracts are dried over $Na_2SO_4$. Concentration under reduced pressure gives Intermediate 13.2 as a white amorphous material; ES-MS: M=478; HPLC: $_Bt_{Ret}$=1.61 min.

Intermediate 13.3

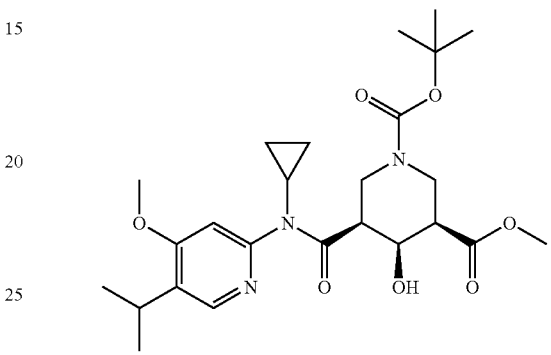

To a solution of (3R,4S,5S)-starting material-G (499.7 mg, 1.647 mmol) in $CH_2Cl_2$ (33 mL) under $N_2$ at 0° C. is added 1-chloro-N,N,2-trimethyl-1-propenyl amine (0.22 mL, 1.65 mmol). The solution is stirred at the same temperature for 60 min. Then, Intermediate 4.4 (683.3 mg, 3.3 mmol) is added at 0° C. The resulting solution is warmed to RT and stirred for 60 min. Then, the mixture is diluted with $H_2O$ and extracted with $CH_2Cl_2$. The combined organic extracts are dried over $Na_2SO_4$. Concentration under reduced pressure gives the crude residue, which is purified by silica gel chromatography to give Intermediate 13.3. ES-MS: M=492; HPLC: $_Ct_{Ret}$=2.96 min.

EXAMPLE 14

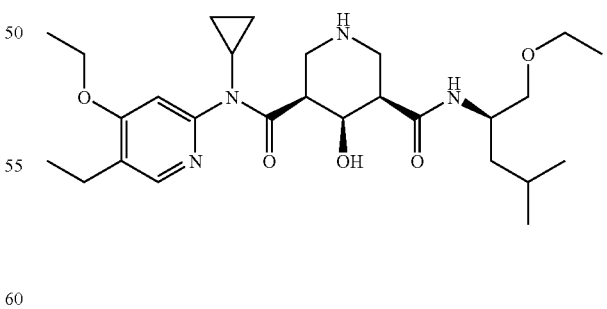

A solution of Intermediate 14.1 (65 mg, 0.107 mmol) in 4N HCl in dioxane (2 mL) under $N_2$ is stirred at RT for 40 min. Concentration under reduced pressure gives the crude HCl salt. The crude is purified by preparative reversed phase HPLC to give Example 14 as a white material: ES-MS: M+H=505: $_Ct_{Ret}$=2.79 min.

Intermediate 14.1

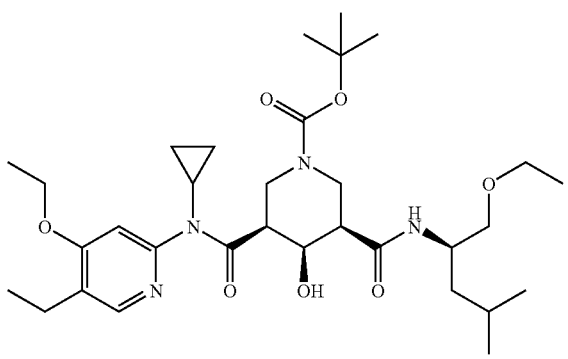 [SMILES: CCOC[C@@H](CC(C)C)NC(=O)[C@@H]1CN(C(=O)OC(C)(C)C)C[C@H](C(=O)N(c2cc(OCC)c(CC)cn2)C2CC2)[C@@H]1O]

To a solution of Intermediate 14.2 (150 mg, 0.314 mmol) in CH$_2$Cl$_2$ (1 mL) under N$_2$ at RT are added EDCl.HCl (90 mg, 0.471 mmol) and HOAt (64 mg, 0.471 mmol). The reaction mixture is stirred at the same temperature for a few minutes. Then, Intermediate 1.7 (69 mg, 0.38 mmol) and triethylamine (0.066 mL, 0.471 mmol) are added at RT. The resulting solution is stirred at the same temperature overnight. Concentration under reduced pressure gives crude residue, which is purified by silica gel chromatography to afford Intermediate 14.1 as a white amorphous material; ES-MS: M=605; HPLC: $_c t_{Ret}$=3.56 min.

Intermediate 14.2

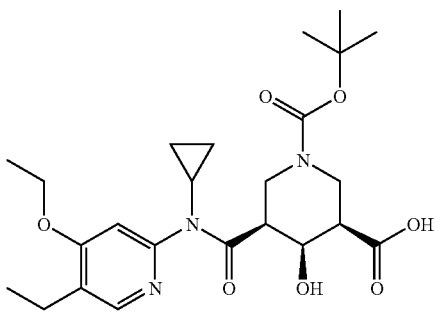 [SMILES: CCOc1cc(N(C(=O)[C@H]2CN(C(=O)OC(C)(C)C)C[C@@H](C(=O)O)[C@H]2O)C2CC2)ncc1CC]

To a solution of Intermediate 14.3 (500 mg, 1.02 mmol) in THF (10 mL) at 0° C. is slowly added aqueous LiOH (84 mg, 2.10 mmol in H$_2$O (10 mL). The resulting solution is stirred at the same temperature for 40 min. The reaction mixture is diluted with H$_2$O and washed with Et$_2$O. The aqueous phase is acidified with sat. KHSO$_4$ aq. and extracted with Et$_2$O. The combined organic extracts are dried over Na$_2$SO$_4$. Concentration under reduced pressure gives Intermediate 14.2 as a white amorphous material; ES-MS: M=478; HPLC: $_c t_{Ret}$=2.79 min.

Intermediate 14.3

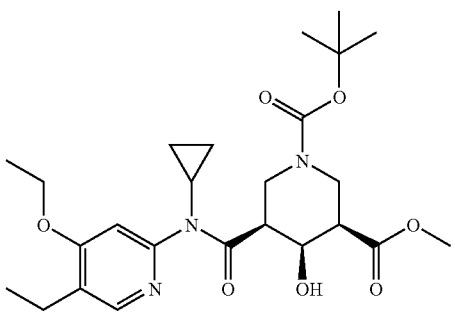 [SMILES: CCOc1cc(N(C(=O)[C@H]2CN(C(=O)OC(C)(C)C)C[C@@H](C(=O)OC)[C@H]2O)C2CC2)ncc1CC]

To a solution of (3R,4S,5S)-starting material-G (1 g, 3.3 mmol) in CH$_2$Cl$_2$ (33 mL) under N$_2$ at 0° C. is added 1-chloro-N,N,2-trimethyl-1-propenyl amine (0.523 mL, 3.95 mmol). The solution is stirred at the same temperature for 60 min. Then, Intermediate 8.2 (817 mg, 3.95 mmol) and Et$_3$N (0.552 mL, 3.95 mmol) are added at 0° C. The resulting solution is warmed to RT and stirred for 60 min. Then, the mixture is diluted with H$_2$O and extracted with CH$_2$Cl$_2$. The combined organic extracts are dried over Na$_2$SO$_4$. Concentration under reduced pressure gives the crude residue, which is purified by silica gel chromatography to give Intermediate 14.3. ES-MS: M=492; HPLC: $_c t_{Ret}$=3.01 min.

EXAMPLE 15

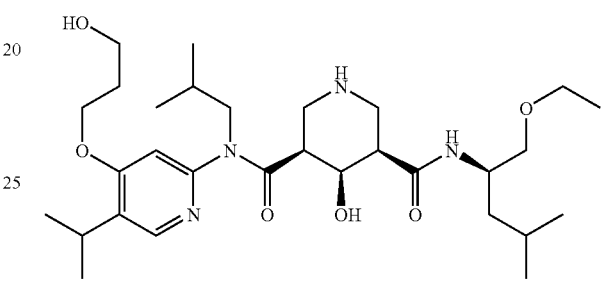

A solution of Intermediate 15.1 (15.1 mg, 0.023 mmol) in 4N HCl in dioxane (3 mL) under N$_2$ is stirred at RT for 30 min. Concentration under reduced pressure gives Example 15 as a white material: ES-MS: M+H=565; $_c t_{Ret}$=4.30 min.

Intermediate 15.1

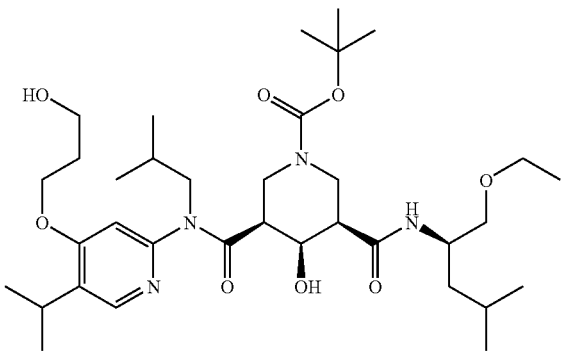 [SMILES: CCOC[C@@H](CC(C)C)NC(=O)[C@@H]1CN(C(=O)OC(C)(C)C)C[C@H](C(=O)N(CC(C)C)c2cc(OCCCO)c(C(C)C)cn2)[C@@H]1O]

H$_2$ gas is streamed into a black suspension of intermediate 15.2 (22 mg, 0.029 mmol) and 10% Pd—C (1 mg) in MeOH (2 mL) at RT. After stirring for overnight at RT, the reaction mixture is filtrated through Celite. The filtrate is concentrated under reduced pressure and purification with silica gel column chromatography (hexane/EtOAc) give intermediate 15.1 (15.1 mg, 0.023 mmol, 78%). ESI-MS (M+H): 665, HPLC: $_c t_{Ret}$=4.57 min.

Intermediate 15.2

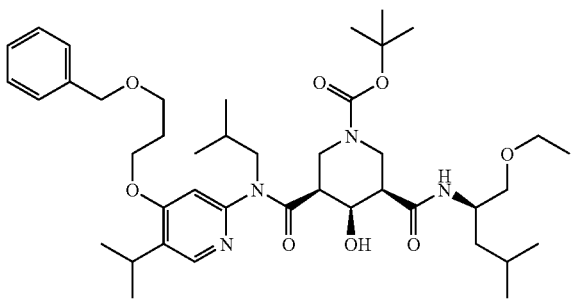 [SMILES: CCOC[C@@H](CC(C)C)NC(=O)[C@@H]1CN(C(=O)OC(C)(C)C)C[C@H](C(=O)N(CC(C)C)c2cc(OCCCOCc3ccccc3)c(C(C)C)cn2)[C@@H]1O]

To a solution of intermediate 15.3 (34.9 mg) and intermediate 1.7 (12.1 mg, 0.067 mmol) in CH$_2$Cl$_2$ (2 mL) are added EDCl.HCl (16 mg, 0.083 mmol), HOAt (11.3 mg, 0.083 mmol), and Et$_3$N (9.3 μL, 0.067 mmol) at room temperature, then the mixture is stirred for overnight at RT. After adding water, the mixture is extracted with CH$_2$Cl$_2$. The organic layer is dried and concentration under reduced pressure and purification with silica gel column chromatography (hexane/EtOAc) to give intermediate 15.2 (22 mg, 0.029 mmol).; ES-MS: M$^+$=755: $_B$t$_{Ret}$=2.54 min.

Intermediate 15.3

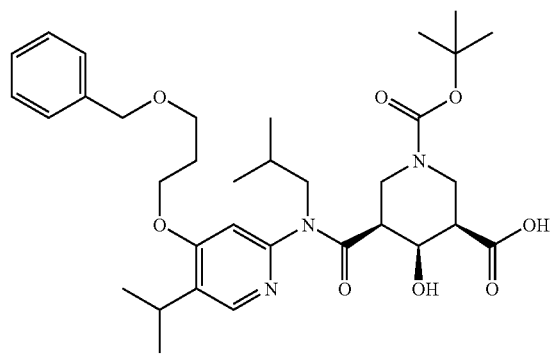 [SMILES: CC(C)CN(C(=O)[C@H]1CN(C(=O)OC(C)(C)C)C[C@@H](C(=O)O)[C@H]1O)c1cc(OCCCOCc2ccccc2)c(C(C)C)cn1]

To a solution of intermediate 15.4 (36.6 mg) in THF/H$_2$O (3/3 mL) is added LiOH.H$_2$O (6.8 mg, 0.29 mmol) at 0° C. After stirring for 30 min at RT, the reaction is quenched with 5% KHSO$_4$ aq. And the mixture is extracted with Et$_2$O. The organic layer is dried over Na$_2$SO$_4$. Concentration under reduced pressure gives intermediate 15.3 (34.9 mg); ESI-MS (M+H): 628, HPLC: $_C$t$_{Ret}$=4.66 min.

Intermediate 15.4

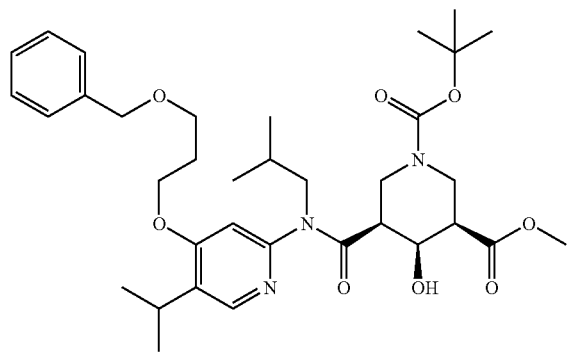 [SMILES: COC(=O)[C@@H]1CN(C(=O)OC(C)(C)C)C[C@H](C(=O)N(CC(C)C)c2cc(OCCCOCc3ccccc3)c(C(C)C)cn2)[C@@H]1O]

To a solution of (3R,4S,5S)-starting material-G (100 mg, 0.33 mmol) in CH$_2$Cl$_2$ (2 mL) under N$_2$ at RT, 1-chloro-N,N-2-trimethyl-1-propenyl amine (55.7 μL, 0.42 mmol) is added. The solution is stirred at RT for 30 min. Then intermediate 15.5 (100 mg, 0.28 mmol) and trimethylamine (62.6 μL, 0.45 mmol) in CH$_2$Cl$_2$ (2 mL) is added at 0° C. The resulting solution is warmed to RT and is stirred at RT for 1 hr. The water and 1N HCl are added. The aqueous phase is extracted with EtOAc. The organic layer is washed with brine, and dried over Na$_2$SO$_4$. Concentration under reduced pressure and purification with preparative TLC (hexane/EtOAc) give intermediate 15.4 (36.6 mg); ESI-MS (M+H): 642, HPLC: $_B$t$_{Ret}$=2.39 min.

Intermediate 15.5

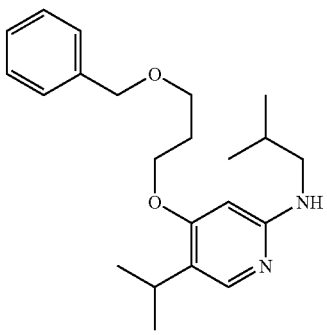 [SMILES: CC(C)CNc1cc(OCCCOCc2ccccc2)c(C(C)C)cn1]

To a solution of intermediate 15.6 (801.1 mg, 2.15 mmol) in CH$_2$Cl$_2$ (3.5 mL) is added triethylsilane (3.4 mL, 21.1 mmol) and TFA (3.3 mL, 43.0 mmol) at 0° C. then the mixture is stirred at 40° C. for 3 hrs. After the bulk of the solvent is concentrated in vacuo, the residue was diluted with EtOAc, neutralized with 1 N NaOH aq. and the mixture is extracted with EtOAc. The organic layer is dried over Na$_2$SO$_4$, concentrated in vacuo. The residue is purified by silica gel column chromatography (hexane/EtOAc) to give intermediate 15.5 (651 mg, 1.83 mmol, 85%). $^1$H NMR (400 MHz, CDCl$_3$) δ 7.76 (s, 1H), 7.35-7.27 (m, 5H), 5.81 (s, 1H), 4.53 (s, 2H), 4.41 (brs, 1H), 4.08 (dd, J=6.6, 6.0 Hz, 2H), 3.67 (dd, J=6.1, 6.0 Hz, 2H), 3.04 (dd, J=6.6, 6.0 Hz, 2H), 3.02-2.97 (m, 1H), 2.11 (quint, J=6.0 Hz, 2H), 1.87 (quint, J=6.6 Hz, 1H), 1.18 (s, 3H), 1.16 (s, 3H), 0.99 (s, 3H), 0.97 (s, 3H); ESI-MS (M+H): 357, HPLC: $_C$t$_{Ret}$=3.60 min.

Intermediate 15.6

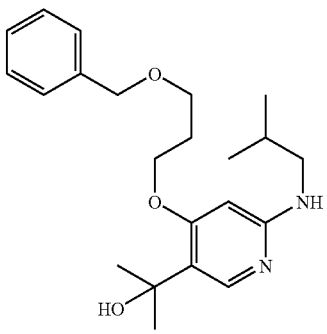 [SMILES: CC(C)CNc1cc(OCCCOCc2ccccc2)c(C(C)(C)O)cn1]

To a solution of intermediate 15.7 (1.28 g, 3.1 mmol) in THF (16 mL) is added 1 M MeMgBr in THF (15.9 mL, 15.4 mmol) at 0° C. After stirred at the same temperature for 1 hr, the mixture is warmed up to RT and stirred for overnight at RT. After adding water and sat NaHCO$_3$ aq., the mixture is extracted with EtOAc. The organic layer is washed with brine and dried over Na$_2$SO$_4$, concentrated in vacuo. The residue is purified by silica gel column chromatography (hexane/EtOAc) to give intermediate 15.6 (1.06 g, 2.8 mmol, 92%). $^1$H NMR (400 MHz, CDCl$_3$) δ 7.91 (s, 1H), 7.35-7.27 (m, 5H), 5.86 (s, 1H), 4.53 (s, 3H), 4.18 (dd, J=6.1, 6 Hz, 2H), 3.72 (brs, 1H), 3.66 (dd, J=6.1, 6 Hz, 2H), 3.05 (dd, J=6.5, 6 Hz, 2H), 2.14 (quint, J=6.0 Hz, 2H), 1.87 (quint, J=6.5 Hz, 1H), 1.56 (s, 6H), 0.99 (s, 3H), 0.97 (s, 3H); ESI-MS (M+): 372, HPLC: $_Ct_{Ret}$=3.12 min.
Intermediate 15.7

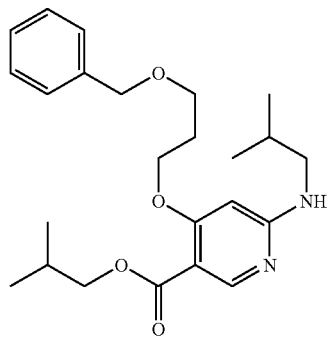 [SMILES: CC(C)CNc1cc(OCCCOCc2ccccc2)c(C(=O)OCC(C)C)cn1]

To a solution of intermediate 15.8 (1.56 g, 4.1 mmol) in NMP (42 mL) at RT is added K$_2$CO$_3$ (856 mg, 6.2 mmol) and isobutyl amine (604 µL, 6.2 mmol) and the mixture is stirred for overnight at 110° C. After adding water, the mixture is extracted with EtOAc. The organic layer is washed with brine and dried over Na$_2$SO$_4$, concentrated in vacuo. The residue is purified by silica gel column chromatography (hexane/EtOAc) to give intermediate 15.7 (1.3 g, 3.1 mmol, 75%). $^1$H NMR (400 MHz, CDCl$_3$) δ 8.60 (s, 1H), 7.38-7.22 (m, 5H), 5.77 (s, 1H), 4.95-4.86 (m, 1H), 4.52 (s, 2H), 4.15 (dd, J=6.1, 6.0 Hz, 2H), 4.00 (d, J=6.6 Hz, 2H), 3.71 (dd, J=6.1, 5.5 Hz, 2H), 3.09 (dd, J=6.6, 6.0 Hz, 2H), 2.19-2.10 (m, 2H), 2.06-1.95 (m, 1H), 1.94-1.83 (m, 1H), 1.00 (s, 3H), 0.99 (s, 3H), 0.98 (s, 3H), 0.97 (s, 3H); ESI-MS (M+): 414, HPLC: $_Ct_{Ret}$=3.59 min.
Intermediate 15.8

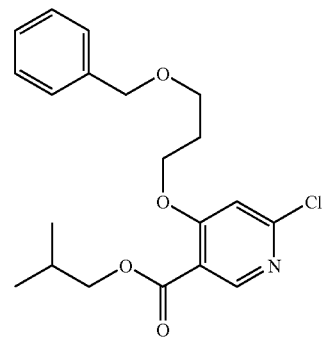 [SMILES: CC(C)COC(=O)c1cnc(Cl)cc1OCCCOCc1ccccc1]

The above crude Intermediate 15.9 (10.4 mmol) is dissolved in NMP (52 mL). To the solution is added K$_2$CO$_3$ (4.32 g, 31.2 mmol) and isobutyl iodide (1.8 mL, 15.6 mmol) and the mixture is stirred at 80° C. for 1 hr. After adding water, the mixture is extracted with EtOAc. The organic layer is washed with brine and dried over Na$_2$SO$_4$, concentrated in vacuo. The residue is purified by silica gel column chromatography (hexane/EtOAc) to give intermediate 15.8 (3.1 g, 8.2 mmol, 79%). $^1$H NMR (400 MHz, CDCl$_3$) δ 8.71 (S, 1H), 7.36-7.23 (m, 5H), 6.91 (s, 1H), 4.51 (s, 2H), 4.21 (t, J=6.0 Hz, 2H), 4.06 (d, J=7.0 Hz, 2H), 3.68 (t, J=6.0 Hz, 2H), 2.20-2.10 (m, 2H), 2.08-1.97 (m, 1H), 1.00 (s, 3H), 0.98 (s, 3H); ESI-MS (M+): 377, HPLC: $_Bt_{Ret}$=2.31 min.
Intermediate 15.9

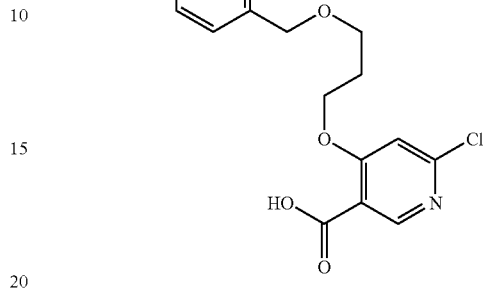

4,6-Dichloronicotinic acid (2 g, 10.4 mmol) is dissolved in THF (20 mL). The solution is added to a solution of NaH (1.04 g, 26.0 mmol) and 3-benzyloxy-1-propanol (4.1 mL, 26.0 mmol) in THF (80 mL) at 0° C. and the resulting mixture is stirred for 3 hrs at RT. After adding water, the mixture is acidified with 1 N HCl and then extracted with EtOAc. The organic extracts are dried over Na$_2$SO$_4$, concentrated in vacuo. The residue is purified by silica gel column chromatography (hexane/EtOAc) to give intermediate 15.9 as 3-benzyloxy-1-propanol mixture. ESI-MS (M+): 321, HPLC: $_Bt_{Ret}$=1.82 min.

EXAMPLE 16

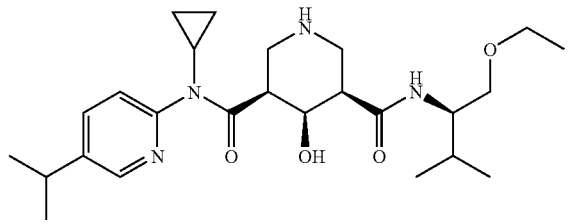 [SMILES: CCOC[C@H](NC(=O)[C@@H]1CNC[C@H](C(=O)N(c2ccc(C(C)C)cn2)C2CC2)[C@@H]1O)C(C)C]

A solution of Intermediate 16.1 (65 mg, 0.116 mmol) in 4 N HCl in dioxane (2 mL) under N$_2$ is stirred at RT for 2 h. Concentration under reduced pressure gives Example 16 as a white material: ES-MS: M+H=461: $_Ct_{Ret}$=3.80 min.
Intermediate 16.1

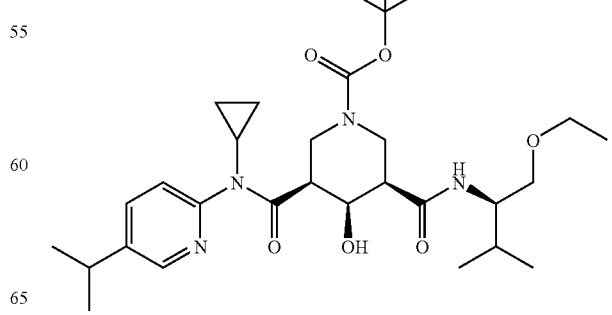

To a solution of intermediate 10.2 (80 mg, 0.179 mmol) and intermediate 7.2 (36 mg, 0.215 mmol) in CH$_2$Cl$_2$ (2 mL) are added EDCl.HCl (54 mg, 0.281 mmol), HOAt (38 mg, 0.281 mmol), and Et$_3$N (28 mg, 0.281 mmol) at room temperature, then the mixture is stirred at the same temperature for 2 h. The reaction is quenched by H$_2$O (10 mL) and extracted with EtOAc (50 mL). The organic extracts were washed with 5% NaHCO$_3$aq, H$_2$O, and brine, then dried over Na$_2$SO$_4$. The organic phase was concentrated in vacuo to give crude residue, which was purified by SiO$_2$ column chromatography to give the Boc intermediate (65 mg, 0.116 mmol, 65%) as a colorless amorphous; ES-MS: M+H=561, HPLC: $_c t_{Ret}$=4.64 min.

EXAMPLE 17

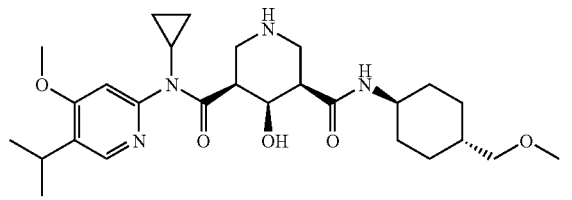 [SMILES: COC[C@H]1CC[C@H](NC(=O)[C@@H]2CNC[C@H](C(=O)N(c3cc(OC)c(C(C)C)cn3)C3CC3)[C@@H]2O)CC1]

Intermediate 17.1 (66 mg, 0.109 mmol) is dissolved in 4 N HCl-dioxane (0.5 mL) under N$_2$ at RT. After stirred for 15 min, concentration under the reduced pressure gives the crude salt. Then, sat. NaHCO$_3$ aq. is added. Organic phase is extracted with CH$_2$Cl$_2$, dried over Na$_2$SO$_4$. Filtration and concentration under the reduced pressure gives the crude. The crude is purified by silica gel chromatography to give Example 17 (free base) (23.45 mg, 0.0466 mmol) in 43%. ES-MS: M+H=503, $_A t_{ret}$=2.10 min.

Intermediate 17.1

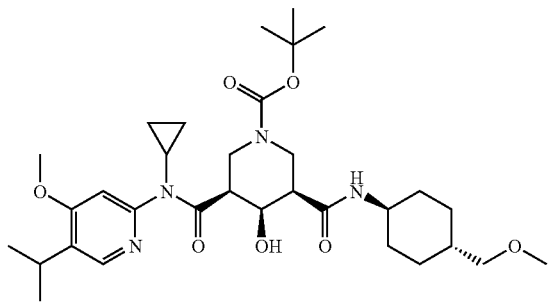 [SMILES: COC[C@H]1CC[C@H](NC(=O)[C@@H]2CN(C(=O)OC(C)(C)C)C[C@H](C(=O)N(c3cc(OC)c(C(C)C)cn3)C3CC3)[C@@H]2O)CC1]

To a solution of intermediate 13.2 (91.6 mg, 0.192 mmol) in CH$_2$Cl$_2$ (3 mL) under N$_2$, EDCl.HCl (60 mg, 0.26 mmol) and HOAt (49 mg, 0.36 mmol) are added at RT. After stirred at that temperature for a few minutes, intermediate 17.2 (34.3 mg, 0.19 mmol) and Et$_3$N (0.133 ml, 0.96 mmol), dissolved in CH$_2$Cl$_2$ (3 mL) are added. The resulting solution is stirred at that temperature for 1 hr. Concentration under the reduced pressure gives the crude. Purification by silica gel chromatography affords intermediate 17.1 (66.0 mg, 0.109 mmol) in 57% yield. ES-MS: M+H=603, $_c t_{ret}$=3.21 min.

Intermediate 17.2

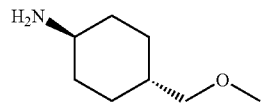

Intermediate 17.3 (46.8 mg, 0.192 mmol) is dissolved in 4 N HCl-dioxane (1 mL) under N$_2$. After stirred at RT for 30 min, concentration under the reduced pressure gives intermediate 17.2 (34.3 mg, 0.19 mmol) in 99%. ES-MS: M+H= 144, $_c t_{ret}$=1.21 min. $^1$H NMR (400 MHz, CDCl$_3$) δ 8.27 (br, 2H), 7.90-7.55 (br, 1H), 3.31 (s, 3H), 3.18 (brd, J=6.04 Hz, 2H), 3.13-3.00 (br, 1H), 2.40-2.00 (br, 3H), 1.88 (brd, J=13.12 Hz, 2H), 1.70-1,40 (br, 2H), 1.18-0.99 (br, 2H).

Intermediate 17.3

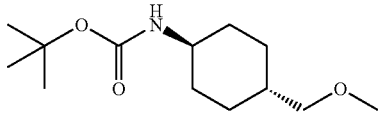 [SMILES: COC[C@H]1CC[C@H](NC(=O)OC(C)(C)C)CC1]

To a solution of intermediate 17.4 (112.1 mg, 0.488 mmol) in THF (3 mL) under N$_2$, sodium hydride (19.5 mg in 60 wt % mineral oil, 0.488 mmol) and methyl iodine (30.3 uL, 0.488 mmol) are added at 0° C. The solution is warmed to RT. After stirred at that temperature overnight, H$_2$O and sat. KHSO$_4$ aq. are added. Organic phase is extracted with ethyl acetate, dried over Na$_2$SO$_4$. Filtration and concentration under the reduced pressure gives the crude. Purification by silica gel chromatography provides the desired intermediate 17.3 (46.8 mg, 0.19 mmol) in 39% yield. ES-MS: M+H=244, $_c t_{ret}$=1.92 min. $^1$H NMR (400 MHz, CDCl$_3$) δ 4.40-4.30 (m, 1H), 3.37 (br, 1H), 3.32 (s, 3H), 3.17 (d, J=6.56 Hz, 2H), 2.02 (d, J=9.56 Hz, 2H), 1.81 (d, J=11.6 Hz, 2H), 1.49 (m, 1H), 1.44 (s, 9H), 1.13-0.98 (m, 4H).

Intermediate 17.4

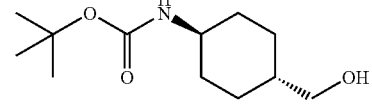

To a solution of commercially available cis-4-tert-butoxy-carbonylamino-cyclohexanecarboxylic acid (200 mg, 0.82 mmol) in THF (3 mL) under N$_2$, Et$_3$N (0.17 mL, 1.23 mmol) and isobutyl chlorofomate (0.106 mL, 0.82 mmol) are added at 0° C. After stirred at that temperature for 30 min, filtration and concentration under the reduced pressure give anhydride.

To a solution of the crude in MeOH (5 mL) under N$_2$, NaBH$_4$ (170 mg, 4.49 mmol) is added at 0° C. After stirred at that temperature for 40 min, sat. KHSO$_4$aq. is added to the solution. Organic phase is extracted with CH$_2$Cl$_2$, dried over $Na_2SO_4$. Filtration and concentration under the reduced pressure give the crude. Purification by silica gel chromatography affords intermediate 17.4 (185.3 mg, 0.808 mmol) in 99% yield. ES-MS: M+H=230, $_c t_{ret}$=1.62 min. $^1$H NMR (400 MHz, $CDCl_3$) δ 4.38 (br, 1H), 3.45 (br, 2H), 3.38 (br, 1H), 2.04 (d, J=9.12 Hz, 2H), 1.83 (d, J=10.8 Hz, 2H), 1.47 (s, 9H), 1.26 (dd, J=7.32, 7.08 Hz, 1H), 1.15-0.99 (m, 4H).

EXAMPLE 18

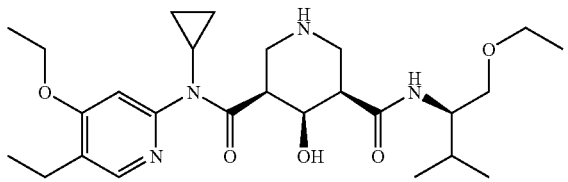 [SMILES: CCOC[C@H](NC(=O)[C@@H]1CNC[C@H](C(=O)N(c2cc(OCC)c(CC)cn2)C2CC2)[C@@H]1O)C(C)C]

A mixture of intermediate 18.1 form (180 mg, 0.305 mmol) and HCl in dioxane (4 M solution, 2 mL) is stirred at room temperature for 1 h. The reaction mixture is concentrated in vacuo to give example 18 (170 mg) as a colorless amorphous; ES-MS: M+H=491, HPLC: $_c t_{Ret}$=2.46 min.

Intermediate 18.1

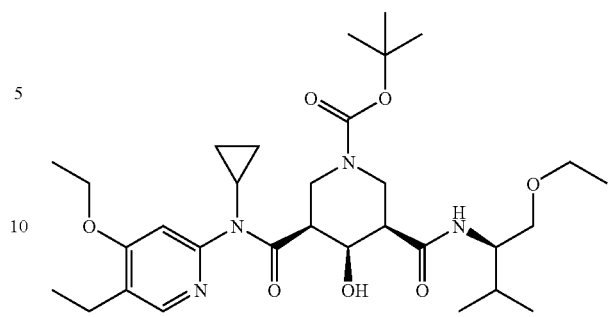

To a solution of intermediate 14.2 (200 mg, 0.419 mmol) and intermediate 7.2 (105 mg, 0.628 mmol) in $CH_2Cl_2$ (2 mL) are added EDCl.HCl (120 mg, 0.628 mmol), HOAt (85 mg, 0.628 mmol), and $Et_3N$ (64 mg, 0.628 mmol) at room temperature, then the mixture is stirred at the same temperature for 2 h. The reaction is quenched by $H_2O$ (50 mL) and extracted with EtOAc (100 mL). The organic extracts are washed with 5% $NaHCO_3$aq, $H_2O$, and brine, then dried over $Na_2SO_4$. The organic phase is concentrated in vacuo to give crude residue, which is purified by $SiO_2$ column chromatography to give intermediate 18.1 (180 mg, 0.305 mmol, 73%) as a colorless amorphous; ES-MS: M+H=591, HPLC: $_c t_{Ret}$=3.37 min.

Biological Tests

Renin inhibitory activity was assessed in vitro by the method as outlined above in item 2).

| Results for representative compounds of formula I | |
|---|---|
| Structure | IC50 (FRET) nM |
| | 0.9 |
| | 3 |

-continued

Results for representative compounds of formula I

| Structure | IC50 (FRET) nM |
|---|---|
| (structure) | 0.6 |
| (structure) | 0.4 |
| (structure) | 0.9 |
| (structure) | 2 |
| (structure) | 0.9 |

-continued

Results for representative compounds of formula I

| Structure | IC50 (FRET) nM |
|---|---|
| 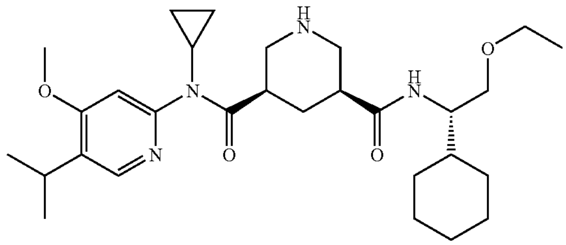 [SMILES: CCOC[C@@H](NC(=O)[C@@H]1CNC[C@H](C(=O)N(c2cc(OC)c(C(C)C)cn2)C2CC2)C1)C1CCCCC1] | 0.3 |
| 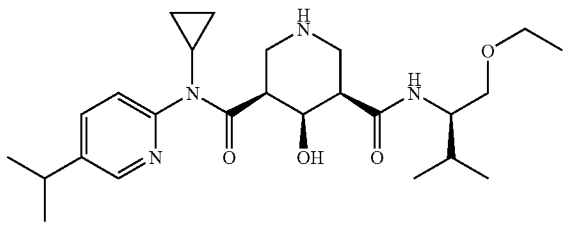 [SMILES: CCOC[C@H](NC(=O)[C@@H]1CNC[C@H](C(=O)N(c2ccc(C(C)C)cn2)C2CC2)[C@@H]1O)C(C)C] | 2.5 |
| | 0.8 |
| 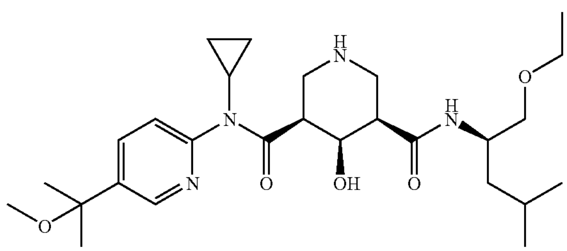 [SMILES: CCOC[C@@H](CC(C)C)NC(=O)[C@@H]1CNC[C@H](C(=O)N(c2ccc(C(C)(C)OC)cn2)C2CC2)[C@@H]1O] | 2 |
| 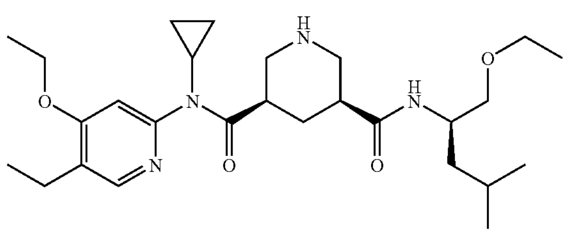 [SMILES: CCOC[C@@H](CC(C)C)NC(=O)[C@@H]1CNC[C@H](C(=O)N(c2cc(OCC)c(CC)cn2)C2CC2)C1] | 0.6 |
| | 0.8 |

Results for representative compounds of formula I

| Structure | IC50 (FRET) nM |
|---|---|
| (structure) | 0.3 |
| (structure) | 6.0 |
| (structure) | 2.5 |
| (structure) | 9.0 |
| (structure) | 0.6 |

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The appropriate components, processes, and methods of those patents, applications and other documents may be selected for the present invention and embodiments thereof.

We claim

1. The compound selected from the compounds of the formula:

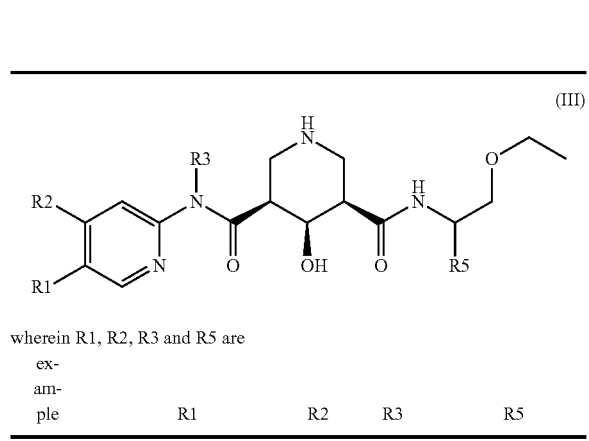

or a pharmaceutically acceptable salt thereof, respectively.

2. A pharmaceutical formulation, comprising:
   the compound according to claim 1, or a pharmaceutically acceptable salt thereof and at least one pharmaceutically acceptable carrier material.

3. A method of treatment of hypertension, comprising:
   administering to a warm-blooded animal in need of such treatment a pharmaceutically effective amount of the compound according to claim 1 or a pharmaceutically acceptable salt thereof.

4. A process for the manufacture of the compound according to claim 1, said process comprising:

reacting a compound of the formula IV,

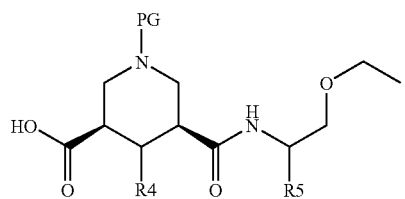

(IV)

wherein PG is a protecting group and R4 and R5 are as defined in claim 1, or an activated derivative thereof, with a compound of the formula V,

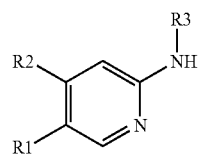

(V)

wherein R1, R2 and R3 are as defined in claim 1; or reacting a compound of the formula VI,

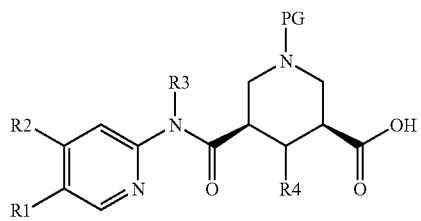

(VI)

wherein PG is a protecting group and R1, R2, R3 and R4 are as defined in claim 1, or an activated derivative thereof, with a compound of the formula VII,

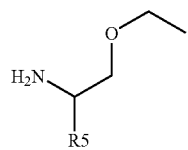

(VII)

wherein R5 is as defined in claim 1;

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups or bound resins are removed at an appropriate stage in order to obtain a corresponding compound of the formula I, or a salt thereof.

5. A process for the manufacture of the compound according to claim 1, said process comprising reacting a compound of formula (IXa)

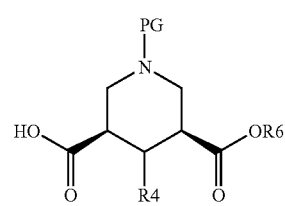

(IXa)

wherein PG is a protecting group, R4 is as defined in any one of the preceding claims and R6 is unsubstituted or substituted alkyl or alkenyl, or an activated derivative thereof, with a compound of the formula V,

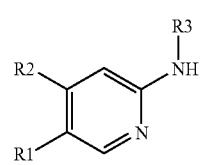

(V)

wherein R1, R2 and R3 are as defined in claim 1; to obtain the amide of formula Xa

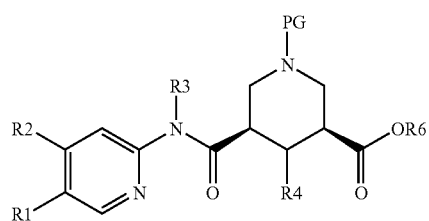

(Xa)

which is subjected to hydolysis of the ester moiety to obtain a compound of formula XIa

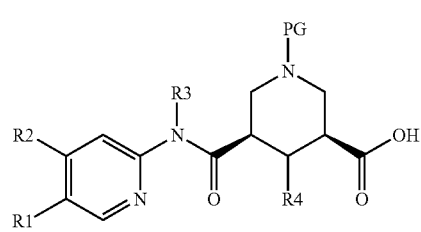

(XIa)

which compound or an activated derivative thereof, can be in turn reacted with a compound of the formula VII,

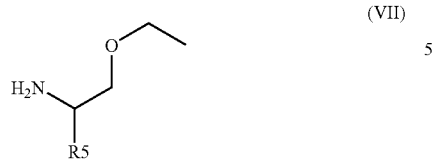

(VII)

wherein R5 is as defined in claim 1, to obtain a compound of formula XII

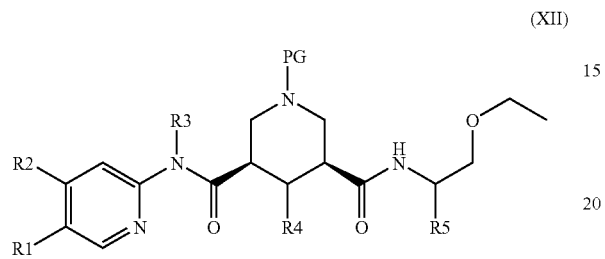

(XII)

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups or bound resins are removed at an appropriate stage in order to obtain a corresponding compound of the formula I, or a salt thereof.

6. A process for the manufacture of the compound according to claim 1, said process comprising reacting a compound of formula (IXb)

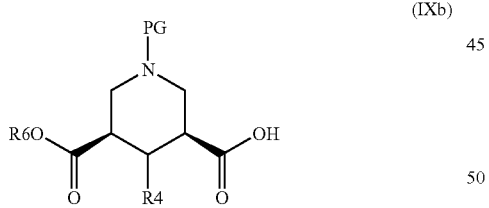

(IXb)

wherein PG is a protecting group, R4 is as defined in claim 1 and R6 is unsubstituted or substituted alkyl or alkenyl, or an activated derivative thereof, with a compound of the formula VII,

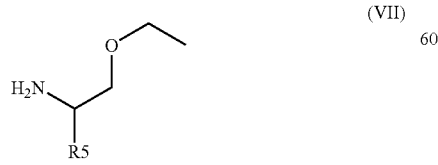

(VII)

wherein R5 is as defined in claim 1, to obtain the amide of formula Xb

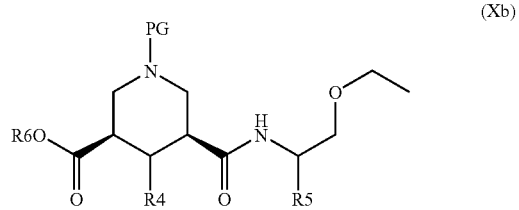

(Xb)

which is subjected to hydrolysis of the ester moiety to obtain a compound of formula XIb

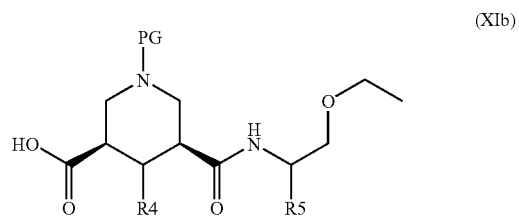

(XIb)

which compound or an activated derivative thereof, can be in turn reacted with a compound of the formula V,

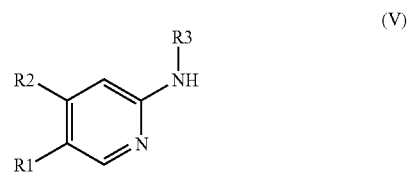

(V)

wherein R1, R2 and R3 are as defined in claim 1, to obtain a compound of formula XII

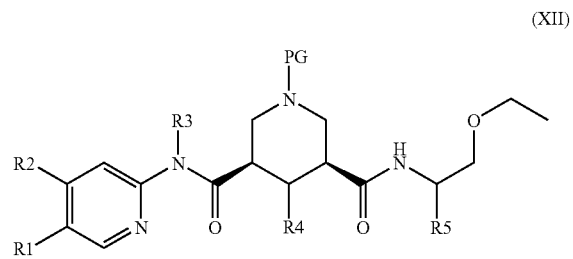

(XII)

and, if desired, subsequent to any one or more of the processes mentioned above converting an obtainable compound of the formula I or a protected form thereof into a different compound of the formula I, converting a salt of an obtainable compound of formula I into the free compound or a different salt, converting an obtainable free compound of formula I into a salt thereof, and/or separating an obtainable mixture of isomers of a compound of formula I into individual isomers;

where in any of the starting materials, in addition to specific protecting groups mentioned, further protecting groups may be present, and any protecting groups or bound resins are removed at an appropriate stage in order to obtain a corresponding compound of the formula I, or a salt thereof.

* * * * *